(12) United States Patent
Glenn, Jr. et al.

(10) Patent No.: US 6,495,125 B2
(45) Date of Patent: Dec. 17, 2002

(54) TOPICAL COMPOSITIONS COMPRISING PROTECTED FUNCTIONAL THIOLS

(75) Inventors: Robert Wayne Glenn, Jr., Surrey (GB); Alan Roy Katritzky, Gainesville, FL (US); Eric Block, Niskayuna, NY (US); Matthew David Shair, Boston, MA (US); Thomas Ehlis, Freiburg (DE); Joseph Anthony Lupia, Colfax, NC (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/755,817

(22) Filed: Jan. 5, 2001

(65) Prior Publication Data

US 2002/0012639 A1 Jan. 31, 2002

Related U.S. Application Data

(63) Continuation-in-part of application No. 09/478,855, filed on Jan. 7, 2000.
(60) Provisional application No. 60/115,278, filed on Jan. 8, 1999, and provisional application No. 60/129,453, filed on Apr. 15, 1999.

(51) Int. Cl.$^7$ .................................................. A61K 7/06
(52) U.S. Cl. ..................... 424/70.9; 424/70.1; 424/401; 424/544; 424/316
(58) Field of Search ..................... 424/401, 59, 70.1, 424/70.9; 544/316

(56) References Cited

U.S. PATENT DOCUMENTS 4,973,475 A  *  11/1990  Schnetzinger et al.  ........  424/62
5,087,733 A  *  2/1992  Deppert et al.  ..........  424/70.28
5,206,013 A  *  4/1993  Deppert et al.  ..........  424/70.15
5,211,942 A  *  5/1993  Deppert et al.  .............  132/202
5,523,080 A  *  6/1996  Gough et al.  ............  424/70.12
5,525,332 A  *  6/1996  Gough et al.  ............  424/70.12

FOREIGN PATENT DOCUMENTS

FR         2197887      *  6/1988      ............ A61K/7/09

* cited by examiner

Primary Examiner—Jose' G. Dees
Assistant Examiner—Konata M. George
(74) Attorney, Agent, or Firm—Stephen T. Murphy; Andrew A. Paul; Tara M. Rosnell

(57) ABSTRACT

This invention relates to a topical composition for treating amino acid based substrates comprising a protected thiol compound having the formula $$R-(S-Pr)_m$$

where R is a functional group, S is sulfur, and Pr is a heterocyclic protecting group, and m is an integer between 1 and 100. The invention further relates to systems which comprise this protected thiol compound and an activating mechanism. The protected thiol compounds of the present invention may be used in hair care compositions, textile care compositions, cosmetic compositions, oral care compositions, skin care, nail care, laundry care, acne care and animal care compositions. Preferred embodiments of the present invention provide a modified UV absorber and a modified antioxidant, methods for making them and compositions conprising them.

7 Claims, No Drawings

TOPICAL COMPOSITIONS COMPRISING PROTECTED FUNCTIONAL THIOLS

CROSS REFERENCE TO RELATED APPLICATION

This application is a continuation-in-part application of U.S. application Ser. No. 09/478,855, filed Jan. 7, 2000, which claimed the benefit of U.S. Provisional Application No. 60/115,278, filed Jan. 8, 1999, and U.S. Provisional Application No. 60/129,453, filed Apr. 15, 1999.

TECHNICAL FIELD

The present invention relates to topical compositions for treating amino acid based substrates. The topical compositions comprise cosmetic or therapeutic actives that have been bound to a protected thiol which acts as a molecular 'hook' to impart "permanent" benefits to the amino acid based substrates. The amino acid based substrates can include, for example, proteinaceous materials such as keratin, as found in human hair, animal fur, velus hair on skin, finger and toe nails; various animal body parts, such as horns, hooves and feathers; other naturally occurring protein containing materials, such as wool; and synthetic polymers. Of particular interest are compositions which deliver and attach cosmetic actives to human hair.

BACKGROUND OF THE INVENTION

It is well known in the art that amino-acid based fibers, particularly hair, can be treated with agents that deliver one or more cosmetic benefits, such as conditioning, styling or setting. The conventional cosmetic products which have been known and used commercially have relied upon two key factors: deposition and retention. The cosmetic actives must first be physically deposited onto the hair fiber where the active imparts a benefit to a sufficient degree. Secondly, it is essential that the cosmetic actives be retained on the hair beyond the completion of the treatment. For example, when hair is rinsed to remove unwanted excess composition (e.g., a conditioner) a sufficient amount of the cosmetic active (humectant, moisturizer, etc.) remains bonded to the hair so as to maintain the desired cosmetic benefits.

The bonding of the cosmetic active material to the hair is generally of the nature of physico-chemical intermolecular forces, e.g., physisorption. Such physical forces comprise, for example, hydrogen bonding, electrostatic interactions, van der Waals interactions and the like. As an example, cationic cosmetic agents, generally of the quaternary ammonium type, are known to bond to hair by virtue of the interaction of their cations with anionic amino acid residues within keratin, e.g., glutamic acid, aspartic acid, cysteic acid etc. A major problem, however, with physisorption is the inevitable short lived retention of the cosmetic agent on hair. This is due to the relatively weak physical forces which bind the cosmetic to hair and which are easily disrupted by other treatments, e.g. washing. And, given the frequent need for treating hair, performance retention is difficult to achieve and generally does not last in excess of the period between washes.

One approach that has been disclosed in the art to overcome the above problem to provide truly durable or "permanent" cosmetic benefits to hair that are retained through multiple washes is to utilize molecular "hooks" to chemically bond cosmetic actives to hair keratin, e.g., chemisorption. Chemisorption results in a permanent juncture that is essentially resistant to physical wear from subsequent washings or physical abrasion. Two conventional approaches to achieve chemisorption comprise the use of either electrophilic reactive moieties or thiol reactive moieties attached to the cosmetic active. Electrophilic reactive moieties are designed to react with thiol functional groups present in hair and thiol reactive moieties are designed to react with electrophilic functional groups within the hair to create a covalent bond.

U.S. Pat. No. 5,523,080 issued to Gough et al. on Jun. 4, 1996, U.S. Pat. No. 5,211,942 issued to Deppert et al. on May 18, 1993, and UK Patent Application GB2197887 published on Jun. 2, 1988, all disclose the use of electrophilic moieties. These electrophilic chemistries include the use of azlactone, (haloalkyl)trialkylammonium salts, and acyl halides. All of these molecular hooks have potential to react with hair via an electrophilic mechanism which necessitates sufficient nucleophilic functional groups present within the keratin structure with which to react to a sufficient degree to achieve the desired durable benefits. For hair, this poses a dilemma in that it is generally known that hair does not naturally possess a sufficient concentration of nucleophilic functional groups under consumer mild conditions to drive the reaction. However, it is also generally known that by chemically reducing the disulfide bonds present within the cystine amino acid residues of hair, in a manner analogous to cold waving, sufficient quantities of nucleophilic cystine residues can be produced. Pre-reduction of hair, to enable the chemical reaction with suitable electrophilic cosmetic actives, is illustrated below in reactions (a) and (b). Ker represents keratin protein, R—X represents an alkyl halide electrophilic cosmetic active, R represents a cosmetic agent and X⁻ is a halide anion such as bromide or chloride.

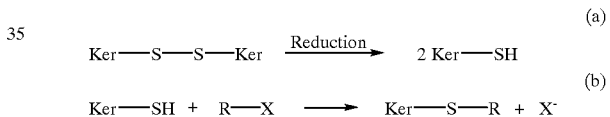

While electrophilic cosmetic actives have been demonstrated effective at providing durable cosmetic benefits to hair, the approach has disadvantages that arise from the required pre-to reduction step. First, the reduction step is known to be a very harsh chemical process that imparts considerable damage to hair. Second, the effective reducing agents are typically mercaptans of low molecular weight and are odiferous. The pre-reduction process generates unpleasant malodor that remains on the hair for greater than a week time in most instances. Thirdly, in addition to unpleasant malodor and resulting hair damage, the required pre-reduction imparts an additional step to the process with attendant added inconvenience to the user.

U.S. Pat. No. 5,087,733 and U.S. Pat. No. 5,206,013 both issued to Deppert et al. on Feb. 11, 1992 and Apr. 27, 1993 respectively, as well as U.S. Pat. No. 4,973,475 issued to Schnetzinger and Ciaudelli on Nov. 27, 1990, describe the use of quaternary ammonium thiols which fall under the general class of nucleophilic reactive actives. Such nucleophilic actives are generally intended to react with cystine amino acid residues present within hair via formation of a mixed disulfide covalent linkage as is demonstrated in the chemical equation (c).

$$R\text{—}SH + Ker\text{—}S\text{—}S\text{—}Ker \rightarrow Ker\text{—}S\text{—}S\text{—}R + Ker\text{—}SH \quad (c)$$

Ker represents keratin and R—SH represents a suitable nucleophilic active where R is a cosmetic agent and —SH representing a nucleophilic moiety. It is generally known that thiols are the preferred nucleophilic reactive moieties that possess enough reactive strength to chemically bond with the disulfide bond of cystine, Ker—S—S—Ker, under safe and mild consumer conditions (e.g., relatively non toxic, less than 120° F., pH 2 to 11). Most other prospective nucleophilic molecular handles are either highly toxic (e.g., selenols), or are unreactive under mild conditions (e.g., alkoxides with pKa~15).

There are two major drawbacks to the use of nucleophilic thiols as reactive moieties to form covalent bonds with keratin. First, thiol nucleophilic moieties are known to be unstable in the presence of air. Atmosphere induced oxidation of the thiols to the corresponding, and unreactive, disulfide as is shown in the following equation (d) where R—SH represents a suitable nucleophilic cosmetic active R being an alkyl cosmetic agent and —SH representing the nucleophilic moiety:

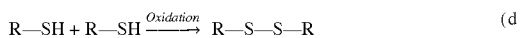  (d)

Such oxidative deactivation of the nucleophilic thiol moieties severely limits their mode of usage. Thus, nucleophilic thiols are generally not stable enough to be utilized as such in a large majority of current product forms, i.e., re-sealable hair care packages widely used for shampoos, rinse-off conditioners etc. Second, the nucleophilic thiol moiety has very little affinity for hair keratin and has very low aqueous solubility, both of which hinder its performance in generating durable cosmetic benefits, especially when attached to hydrophobic, insoluble cosmetic actives, i.e., hydrocarbon conditioners, in-soluble polymers etc.

Despite major efforts, however, the art has not yet provided molecular "hooks" that provide durable cosmetic benefits to hair that last beyond twenty shampoos and which do not necessitate the damaging cold waving of hair, i.e. hair reduction, while being oxidatively stable in solution for long term storage in a variety of currently used product forms, e.g., rinse of conditioners, two-in-one shampoos, etc.

The present invention is concerned with topical compositions comprising classes of compounds containing at least one thiol in a protected form, which can be released to provide a —SH or —S⁻ group prior or simultaneous to use. These protected thiols are referred to herein as "hooks". It is understood that within the scope of this invention that functional thiols as represented herein include both the protonated thiol, R—SH, and unprotonated thiolate, R—S⁻.

It has now been discovered that, surprisingly, such "hooks", R—(S—Pr)$_m$, provide durable cosmetic benefits, when applied to amino-acid based substrates without a damaging cold-waving process, that last beyond twenty shampoos. It has also been discovered that the molecular "hooks" of the present invention provide improved oxidative stability versus conventional thiols by virtue of the appended protecting moiety to the thiol group that reduces the oxidative susceptibility of the sulfur atom(s). Furthermore, it has been found that these molecular "hooks" significantly outperform conventional nucleophilic thiol hooks in providing durable cosmetic benefits. While not being bound by theory, the latter observed effect is believed to be due to the unexpected high affinity for keratin provided by certain polarizable electrophilic groups which offer improved solubility and possibly even electrostatic interaction with the charged keratinaceous substrate. Presumably, such greater affinity affords enhanced diffusion and adsorption to the fiber by the cosmetic active enabling greater opportunity for binding.

The 'hooks' of the present invention enable the achievement of durable cosmetic benefits that are resistant to cleansing or shampooing from essentially a non-damaging process that is void of cold waving. The binding of the cosmetic actives provided by these molecular 'hooks' is to such a degree of durability that the measured cosmetic benefits will remain in hair for multiple shampoo cycles, e.g. eight to twenty or more. While not being restricted by theory, it is believed that such a high degree of durability is due to the formation of covalent bonds between the cosmetic active and the keratinaceous substrate.

This bond formation may occur in either of two ways. First, the protected thiol compound can be mixed with a activating release agent to form the free functional thiol, reaction (e). The free thiol will then react with the substrate thereby attaching the functional group, reaction (f).

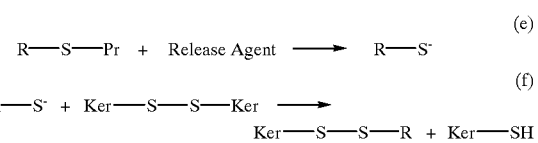

R represents the cosmetic active, Ker represents the keratin protein, S represents sulfur, —SH represents the thiol and Pr represents the protecting group. Based on theory, the above thiol-protecting group bond is broken via some form of activation yielding the reactive unprotected thiol which would then be capable of forming a mixed disulfide with keratin disulfides via nucleophilic displacement. Such activation could be accomplished via hydrolysis or by the action of a nucleophile other than water, either in the substrate itself or in a separate composition. Such hydrolysis or nucleophilic attack can itself be enhanced in several way such as by application of a source of energy or catalysis. This mixing may be done prior to use or simultaneously, during application to the substrate. Where the mixing occurs simultaneously to application, the release of the protecting group occurs in-situ on the substrate.

Surprisingly, it has been found that, alternatively, the formation of the covalent bonds may occur without mixing with a release agent. Direct reaction of certain protected thiol compounds with the hair occurs via the formation of a mixed disulfide with the existing disulfide bonds within keratin as is illustrated below, reaction (g):

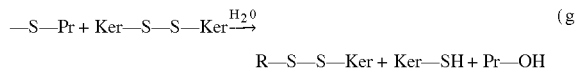

While not being bound to theory, it is believed that the keratin itself could be activating the thiol protecting group bond to enable the observed durable benefits. The resulting free protecting group may or may not undergo decomposition reactions. The byproducts of the activation of the sulfur-heterocyclic bond will usually be removed from the substrate by washing.

The cosmetic agent, R, of the present invention may be monofunctionalized, i.e. the cosmetic active moiety, R, carries a single molecular "hook" connected to the cosmetic agent via a sulfur-sp³ carbon bond, or it may be bis- or multi-functionalized, i.e. the cosmetic active, R, may carry two or more sp³ electrophiles connected to the cosmetic agent via separate sulfur-sp³ carbon bonds. The latter may be useful for example in achieving a greater degree of chemical bonding of the cosmetic agent to the substrate or for generating bonds between adjacent features of the substrate, e.g. producing a cross-linking effect. The latter may be employed to improve the strength or tensile properties of keratinaceous fibers or for enhancing the degree of hair setting compared with prior art hair methods.

It is understood that within the scope of this invention, numerous potentially and actually tautomeric compounds are involved. Thus, for example, 2-mercaptopyridine (I) exists under known conditions in the pyridine-2-thione tautomer form (II). It is to be understood that when this development refers to a particular structure, all of the reasonable additional tautomeric structures are included. In the art, tautomeric structures are frequently represented by one single structure and the present invention follows this general practice.

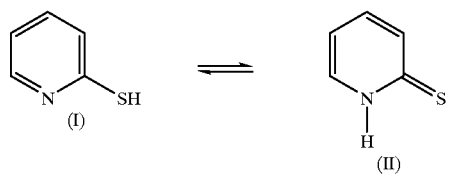

Preferred embodiments of the present invention are related to functional silicone compositions. More specifically, these embodiments are related to functional silicone compositions which are used in the cosmetics industry.

Silicones are widely used in hair care products due to the conditioning benefit that they impart to hair. By modern day technology, the silicone is deposited on hair during the application process but is held only by weak physical forces, such as hydrogen bonding or van der Waals interactions. Because the forces are weak, the benefits of silicone by deposition are short lived. Beneficial conditioning effect can also be caused by treating hair with silanol capped amino-functionalized silicones. These can undergo condensation cure reactions on hair to form somewhat durable films. Generally, conditioning benefits are attributed to the deposition of high molecular weight, high viscosity fluids and gums which can weight down the hair.

It is widely known by those skilled in the art that covalent bonding is the key to "permanent" hair treatment. Processes which alter the structure of the hair, such as permanent wave and color treatment methods, do provide longer lasting effects. These processes include glycolate reduction and peroxide reoxidation. However, the processes are very damaging to hair and can only be carried out every eight to ten weeks.

Gough et al. in U.S. Pat. Nos. 5,523,080 and 5,525,332 describe the synthesis of silicone-azlactone polymers which exhibit covalent bonding and "permanent" conditioning benefit. Gough et al. discuss incorporating an azlactone-functionalized copolymer which consists of vinylazlactone and methacryloyl polydimethylsiloxane monomers into a silicone-active group-hair structure. The hair treatment using the silicone-azlactone polymers did not consist of the steps of reduction with a glycolate or reoxidation with peroxide.

New compositions are constantly being sought which impart improved hair care benefits without a harsh, damaging chemical treatment.

SUMMARY OF THE INVENTION

This invention relates to a topical composition for treating amino acid based substrates comprising a protected thiol compound having the formula

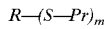

where R is a mono or multivalent cosmetically active functional group, S is sulfur, and Pr is a protecting group, and m is an integer between 1 and 100. The invention further relates to systems which comprise this protected thiol compound and an activating mechanism. The protected thiol compounds of the present invention may be used in hair care compositions, textile care compositions, cosmetic compositions, oral care compositions, skin care, nail care, laundry care, acne care and animal care compositions.

Preferred embodiments of the present invention provide modified UV absorbers and antioxidants, methods for making these compounds and compositions comprosing them.

DETAILED DESCRIPTION OF THE INVENTION

The present invention relates to topical compositions which provide attachment of functional groups to amino acid based substrates.

As used herein, "cystine containing, amino acid based substrates" are proteinaceous materials which contain the amino acid cystine in its amino acid sequence. The phrase "amino acid sequence" refers to a specific configuration of the amino acids comprising a protein. Cystine amino acid units are represented by Ker—S—S—Ker and cysteine amino acid units by Ker—SH. The compositions of the present invention can be used to attach functional groups to materials such as keratin, as found in human and animal hair, skin and nails; various animal body parts such as horns, hooves and feathers; and other naturally occurring protein containing materials, such as wool.

The topical compositions of the present invention can comprise, consist of, or consist essentially of the essential elements and limitations of the invention described herein, as well as any of the additional or optional ingredients, components, or limitations described herein.

All percentages, parts and ratios are by weight of the total composition, unless otherwise specified. All such weights as they pertain to listed ingredients are based on the specific ingredient level and, therefore, do not include solvents, carriers, by-products, filler or other minor ingredients that may be included in commercially available materials, unless otherwise specified.

PROTECTED THIOL COMPOUND

The compositions of the present invention comprise a protected thiol compound having the formula

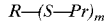

where R is a mono or multivalent cosmetically active functional group, S is sulfur, Pr is a protecting group, and m is an integer ranging from about 1 to about 100, preferably from about 1 to about 50, more preferably equal to 1 to about 20, and most preferably equal to 1 to about 5.

Typically, the protected thiol compounds of the present invention are present in the compositions of the invention in an amount from about 0.000001% to about 30%, preferably from about 0.0001% to about 25%, more preferably from 0.01 to about 20%, even more preferably from about 0.1% to about 10%, and most preferably from about 1% to about 5%, by weight of the composition. Suitable ranges of amounts will generally depend upon the functional group in question. For example, hair conditioners that are modified with the molecular 'hooks' of the present invention will normally be present from about 0.01% to 10% by weight of the composition, and hair styling agents that are modified such as cationic conditioning polymers or polyisobutylene will normally be present from about 0.01 to 10% by weight of the composition, perfluoropolyether materials that are modified may be present from about 0.000001 to 0.1% by weight of the composition, hair dye chromophoric materials may be present from 0.1% to 10% and other film forming polymers that are modified may be present from about 0.01 to 2% of the composition.

The protected thiol compound comprises from about 1 to about 100, preferably from about 1 to about 50, more preferably from about 1 to 20, and most preferably equal from 1 to about 5 sulfur atoms, each linked to one protective group.

Protecting Group

The protected thiol compounds of the present invention comprise 1 to about 100, preferably 1 to 50, more preferably 1 to 20 and most preferably 1 to 5 protecting groups. The protecting group may be selected from the range consisting of heterocyclic protecting groups, $sp^2$ aliphatic trigonal carbon protecting groups, $sp^3$ carbon protecting groups, metal based protecting groups, non-metal and metalloid based protecting groups, energy-sensitive protecting groups and mixtures thereof. The protecting group is preferably selected from the range consisting of heterocyclic protecting groups, $sp^2$ aliphatic trigonal carbon protecting groups, $sp^3$ carbon protecting groups and non-metal protecting groups. The protecting group is more preferably selected from heterocyclic protecting groups, $sp^2$ aliphatic trigonal carbon protecting groups and non-metal protecting groups.

Heterocyclic Protecting Groups

The cosmetic composition of the present invention comprises a protected thiol compound wherein the thiol protective group may be a heterocyclic ring or ring system. Heterocyclic groups that are suitable for use in the present invention include mono- or polyunsaturated or saturated heterocyclic rings, heterocyclic ring systems, fused heterocyclic ring systems, substituted heterocyclic rings, substituted heterocyclic ring systems or substituted fused heterocyclic ring systems. The heterocyclic rings contain from about three to about thirty members, and may contain electronegative heteroatoms including N, O, S, or P. The heterocyclic rings or ring systems also may contain exocyclic double bonds of the C=M type wherein M is O, S, $NA^1$ or $CA^1A^2$. $A^1$ and $A^2$ used here, and $A^3$ and $A^4$ used hereinafter, each represent, independently from one another, a monovalent group which can be the cosmetic active group, R, or H or any of the following: a straight, branched or mono- or polycyclic aliphatic, mono or polyunsaturated alkyl, aryl, heteroalkyl, heteroaliphatic or heteroolefinic system including 1 to 30 carbon atoms together with 0–15 heteroatoms, especially O, N, S, P, Si, and can incorporate one or more substituents including, but not limited to, poly or perfluoro substitution.

Optional substituents on the heterocyclic ring or ring system, $X^1, X^2, X^3, X^4, X^5 \ldots$, can be selected from electron withdrawing, electron neutral, or electron donating groups with Hammett sigma para values between —1.0 and +1.5 which can be non-ionic, zwitterionic, cationic or anionic comprising for example C-linked groups of the classes defined above as $A^1$, $A^2$, $A^3$, and $A^4$; S-linked groups including $SA^1$, SCN, $SO_2A^1$, $SO_3A^1$, $SSA^1$, $SOA^1$, $SO_2NA^1A^2$, $SNA^1A^2$, $S(NA^1)A^2$, $S(O)(NA^1)A^2$, $SA^1(NA^2)$, $SONA^1A^2$; O-linked groups including $OA^1$, $OOA^1$, OCN, $ONA^1A^2$; N-linked groups including $NA^1A^2$, $NA^1A^2A^{3+}$, NC, $NA^1OA^2$, $NA^1SA^2$, NCO, NCS, $NO_2$, $N=NA^1$, $N=NOA^1$, $NA^1CN$, $N=C=NA^1$, $NA^1NA^2A^3$, $NA^1NA^2NA^3A^4$, $NA^1N=NA^2$; other miscellaneous groups including COHal, $CON_3$, $CONA^1_2$, $CONA^1COA^2$, $C(=NA^1)NA^1A^2$, CHO, CHS, CN, NC, Hal, and derived groups that connect one or more of $X^1, X^2, X^3, X^4, X^5$ via a ring system;

Ak is $A^1, A^2, A^3$, and $A^4$ or $X^1, X^2, X^3, X^4, X^5 \ldots$

Hal is F, Cl, Br, or I.

H is hydrogen, O is oxygen, N is nitrogen, C is carbon, S is sulfur, Cl is chlorine, Br is bromine, I is iodine, F is fluorine, R is any cosmetically active, functional group or benefit agent as described herein below.

The invention includes the following preferred non-limiting heterocyclic exemplary classes and their $X^1, X^2, X^3, X^4, X^5 \ldots$ substituted derivatives [Herein referred to as Class I]:

Six membered heterocycles with a single heteroatom such as pyridine:

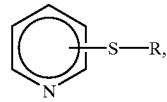

Six membered heterocycles with two heteroatoms such as pyrimidines, pyrazines and pyridazines:

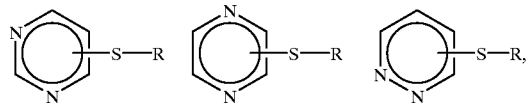

Six membered heterocycles with three and four heteroatoms such as triazines and tetrazines:

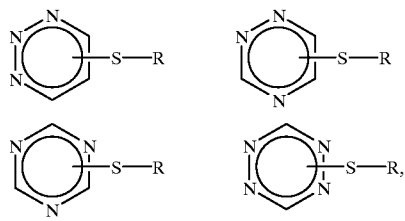

Six membered O, N, and/or S containing heterocycles with C=O, C=S or C=C exocyclic groups:

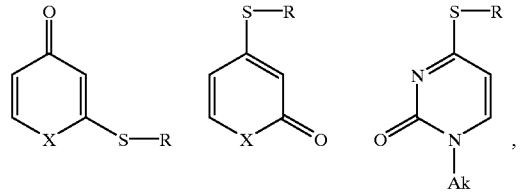

X = O, S, or NX

Cationic six membered heterocycles with one heteroatom such as pyridinium, pyrylium, and thiopyrylium salt derivatives:

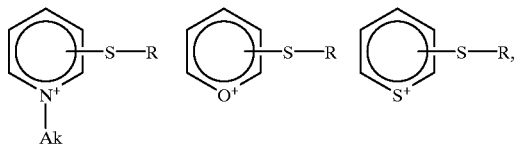

Cationic six membered heterocyclics with two heteroatoms such as pyrimidinium and pyrazinium salt derivatives:

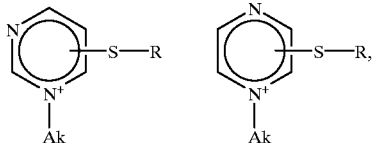

Five membered heterocycles with one heteroatom such as furans, pyrroles, and thiophenes:

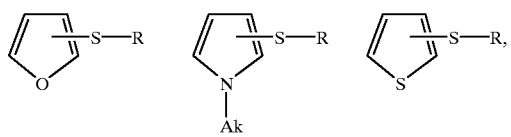

Five membered heterocycles with two heteroatoms such as pyrazoles, isoxazoles, and isothiazoles:

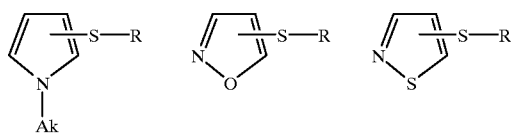

Five membered heterocyclics with three heteroatoms such as 1,2,4-triazoles, 1,2,3-triazoles, 1,2,4-oxadiazoles, and 1,2,4-thiadiazoles:

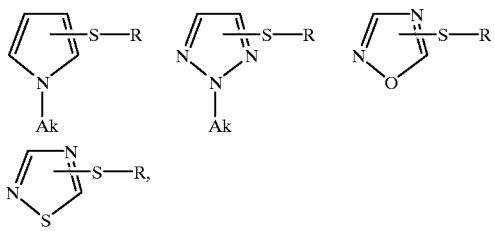

Five membered cationic heterocycles with two or more heteroatoms such as pyrazolium and triazolium:

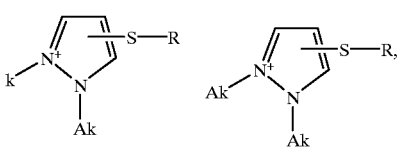

Seven membered heterocycles such as azepines, oxepins and thiepins:

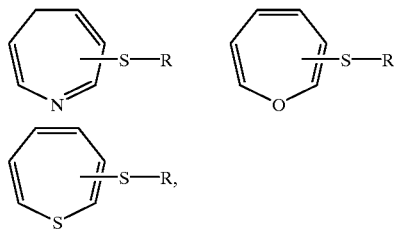

Seven membered cationic heterocycles such as thiepinium salts:

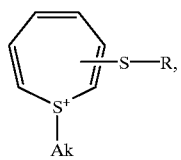

and related variations including combinations of the above heterocycles in a ring system and fused systems both of which may include carbocyclic rings without heteroatoms. The cationic heterocycles will also incorporate a Cl$^-$, Br$^-$, I$^-$ or other suitable negatively charged counterion.

The invention may also include heterocyclic compounds comprising the cosmetic active, R, that are capable of generating a thiol via a ring-opening mechanism. Such compounds are represented by the following structures:

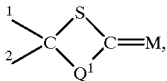

(II)

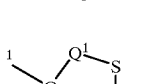

(III)

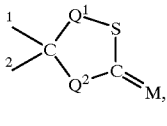

(IV)

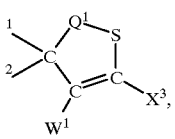

(V)

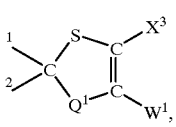

(VI)

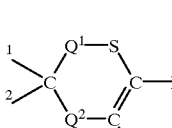

(VII)

-continued

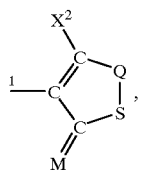
(VIII)

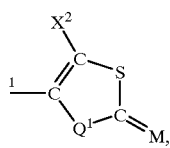
(IX)

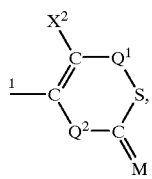
(X)

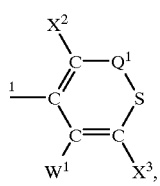
(XI)

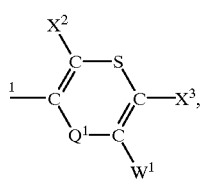
(XII)

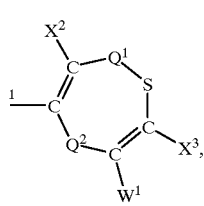
(XIII)

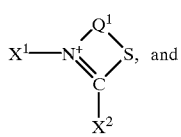
(XIV)

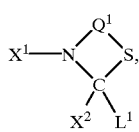
(XV)

wherein at least one cosmetic group, R, comprises or is attached to any of the $X^1$, $X^2$, $X^3$ groups.

$Q^1$ and $Q^2$ represent, independently from one another, a divalent group comparable to $A^1$ but with the open valencies separated by 0 to 4 atoms.

$W^1$ represents an electron withdrawing group with a Hammett sigma para value more positive than 0.10 comprising C-linked groups of the classes defined above as $A^1$, $A^2$, $A^3$; S-linked groups including $SA^1$, SCN, $SO_2A^1$, $SO_3A^1$, $SSA^1$, $SOA^1$, $SONA^1A^2$, $SO_2NA^1A^2$, $SNA^1A^2$, $S(NA^1)A^2$, $S(O)(NA^1)A^2$, $SA^1(NA^2)$; O-linked groups including $OA^1$, $OOA^1$, OCN, $ONA^1A^2$; N-linked groups including $NA^1A^2$ $NA^1A^2A^{3+}$, NC, $NA^1OA^2$, $NA^1SA^2$, NCO, NCS, $NO_2$, $N=NA^1$, $N=NOA^1$, $NA^1CN$, $N=C=NA^1$, $NA^1NA^2A^3$, $NA^1NA^2NA^3A^4$, $NA^1N=NA^2$; other miscellaneous groups including COHal, $CON_3$, $CONA^1_2$, $CONA^1COA^2$, $C(=NA^1)NA^1A^2$, CHO, CHS, CN, NC, Hal, and derived groups that connect one or more of $X^1$, $X^2$, $X^3$, $X^4$, $X^5$ via a ring system;

$L^1$ is a suitable leaving group including but not limited to $SA^1$, $OA^1$, or $NA^1A^2$.

Below are some non-limiting representative examples for each of the above heterocyclic structures (II through XV) that are capable of generating a thiol via a ring-opening mechanism: A thiolactone, thiophthalide, and thiazolidinone (classes II, III and IV),

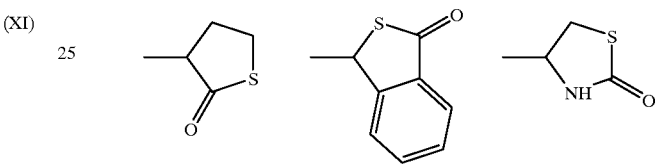

A dihydrothiophene, dihydrothiopyran, and dihydro-1,4-thiazine (classes V, VI and VII),

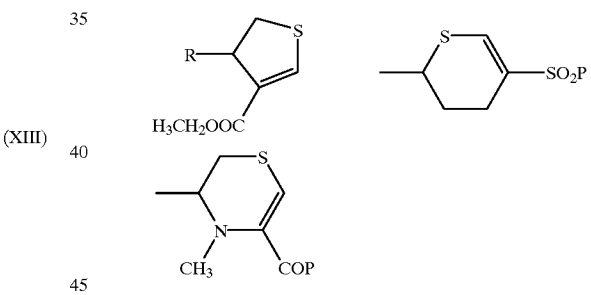

Unsaturated thiolactones and a dihydrothiapyrone (classes VIII, IX and X),

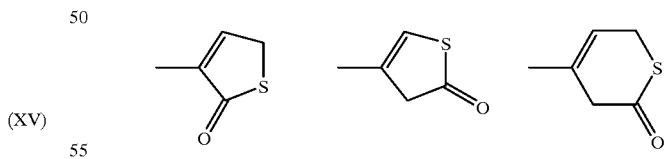

A dihydrothiepin, thiopyran and thiepinone (classes XI, XII and XIII),

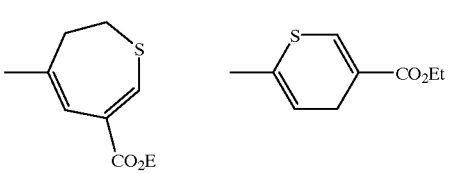

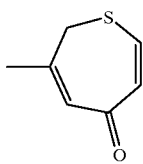

A dihydrothiazoline and 2-methoxythiazolidine (classes XIV and XV),

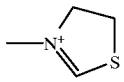 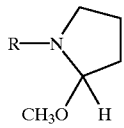

and other related derivatives.

Preferred protected thiol compounds of the heterocyclic thiol protective type include the following non-limiting examples:

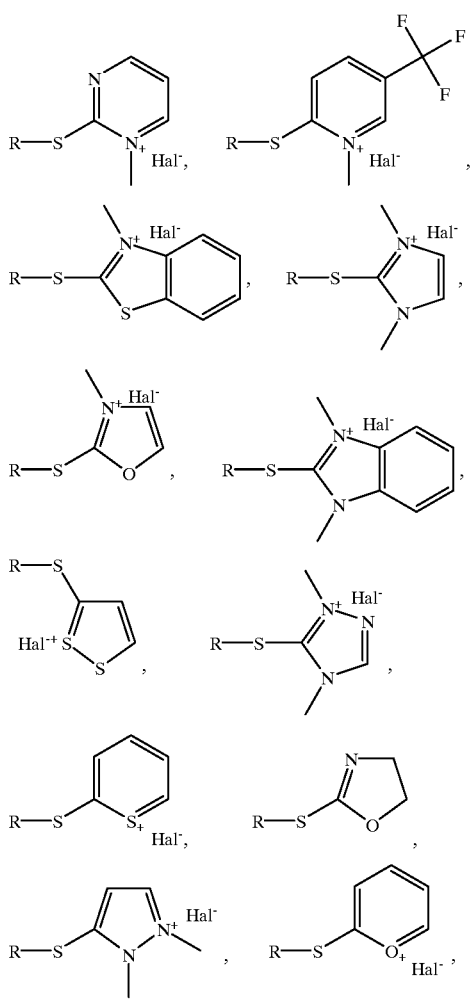

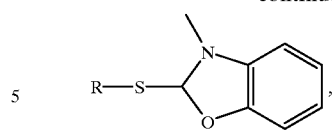

and mixtures thereof, wherein $Hal^-$ is $Cl^-$, $Br^-$, $I^-$ or any suitable negatively charged counterion.

$sp^2$ Aliphatic Trigonal Carbon Protecting Groups

The protecting groups of the present invention may comprise a $sp^2$ carbon moiety wherein the divalent sulfur atom is bonded on one side to the cosmetic active and on the other side to a $sp^2$ carbon atom. Protecting groups of the $sp^2$ aliphatic trigonal carbon type that are suitable for the present invention include (a) aliphatic trigonal carbon atoms double bonded to O, S, N, or C,

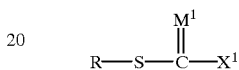

which includes derivatives of the following acids: thiocarboxylic (R—S—C(O)CH$_2$—A$^1$), carbonodithioic (R—S—C(O)S—A$^1$, R—S—C(S)O—A$^1$), carbonothioic (R—S—C(O)O—A$^1$), carbamothioic (R—S—C(O)N—A$^1$A$^2$), dithiocarboxylic (R—S—C(S)CH$_2$A$^1$), carbonotrithioic (R—S—C(S)S—A$^1$), carbamodithioic (R—S—C(S)N—A$^1$A$^2$), carboximidothioic (R—S—C(NA$^1$)CH$_2$—A$^1$), carbonimidodithioic (R—S—C(NA$^1$)S—A$^1$), and carbonimidothioic (R—S—C(NA$^1$)O—A$^1$) acids. Suitable $sp^2$ aliphatic trigonal carbon type protecting groups for use in the topical compositions of the present invention do not include carbamimidothioic acids.

The invention also includes (b) related $sp^2$ carbon derivatives that are capable of releasing a cosmetic thiol via an intramolecular nucleophilic attack and release mechanism,

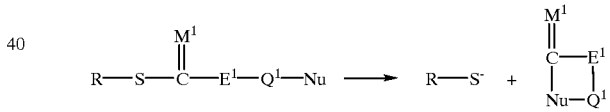

(c) $sp^2$ carbon derivatives that are capable of rearranging to produce a cosmetic containing thiol via an intramolecular nucleophilic attack and rearrangement mechanism,

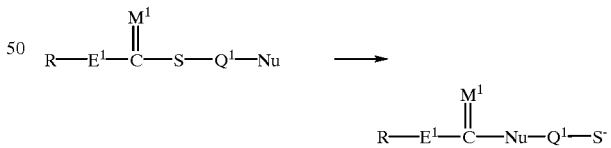

as well as (d) trigonal carbon electrophiles of the anhydride, thioanhydride, and secondary/tertiary amide type,

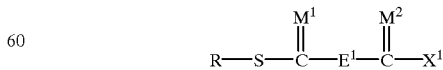

and related aliphatic trigonal carbon variations. The cationic protecting groups will also incorporate a $Cl^-$, $Br^-$, $I^-$ or other suitable negatively charged counterion.

$M^1$, $M^2$ are O, S, NA$^1$, NOA$^1$, NA$^1$A$^{2+}$, CA$^1$=CA$^2$Y$^1$, SA$^+$, OA$^+$.

$E^1$ is O, S, $NA^1$, $CA^1A^2$.

Nu is $NHA^1A^{2+}$, $NA^1A^2$, $OHA^{1+}$, $OA^1$.

$X^1$ represents an electron withdrawing or electron donating group with a Hammett sigma para value between −1.0 and +1.5 which can be non-ionic, zwitterionic, cationic or anionic comprising for example C-linked groups of the classes defined below as $A^1$, $A^2$, $A^3$; S-linked groups including $SA^1$, SCN, $SO_2A^1$, $SO_3A^1$, $SSA^1$, $SOA^1$, $SONA^1A^2$, $SO_2NA^1A^2$, $SNA^1A^2$, $S(NA^1)A^2$, $S(O)(NA^1)A^2$, $SA^1(NA^2)$; O-linked groups including $OA^1$, $OOA^1$, OCN, $ONA^1A^2$; N-linked groups including $NA^1A^2$, $NA^1A^2A^{3+}$, NC, $NA^1OA^2$, $NA^1SA^2$, NCO, NCS, $NO_2$, $N=NA^1$, $N=NOA^1$, $NA^1CN$, $N=C=NA^1$, $NA^1NA^2A^3$, $NA^1NA^2NA^3A^4$, $NA^1N=NA^2$; other miscellaneous groups including COHal, $CON_3$, $CONA^1_2$, $CONA^1COA^2$, $C(=NA^1)NA^1A^2$, CHO, CHS, CN, NC, Hal, and derived groups that connect one or more of $X^1$, $X^2$, $X^3$, $X^4$, $X^5$ via a ring system;

$A^1$, $A^2$ represent, independently from one another, a monovalent group which can be the cosmetic active group, R, or H or any of the following: a straight, branched or mono- or poly-cyclic aliphatic, mono or polyunsaturated alkyl, aryl, heteroalkyl, heteroaliphatic or heteroolefinic system including 1 to 30 carbon atoms together with 0–15 heteroatoms, especially O, N, S, P, Si, and can incorporate one or more substituents including, but not limited to, poly or per fluoro substitution.

Q is a divalent group comparable to $A^1$ but with the open valencies separated by 2 to 7 atoms.

Hal is F, Cl, Br, or I.

$Y^1$ represents electron an withdrawing substituent with a Hammett sigma para value more positive than 0.10. Such electron withdrawing substituents which can be nonionic, zwitterionic, cationic or anionic include the following non-limiting examples: $NO_2$, CN, $COOA^1$, $CONA^1A^2$, $C(O)A^1$, $SO_2A^1$, $SO_2OA^1$, NO, COHal, $CON_3$, $CONA^1A^2$, $CONA^1COA^2$, $C(=NA^1)NA^2A^3$, $C(S)A^1$, NC, SCN, $SO_2A^1$, $SO_3A^1$, $SOA^1$, $SO_2NA^1A^2$, $SNA^1A^2$, $S(NA^1)A^2$, $S(O)(NA^1)A^2$, $NA^1A^2A^{3+}$, $SA^1A^{2+}$.

H is hydrogen, O is oxygen, N is nitrogen, C is carbon, S is sulfur, Cl is chlorine, Br is bromine, I is iodine, F is fluorine, R is any cosmetically active functional group or benefit agent as described herein below.

Non-limiting examples of suitable $X^1$ groups are as follows:

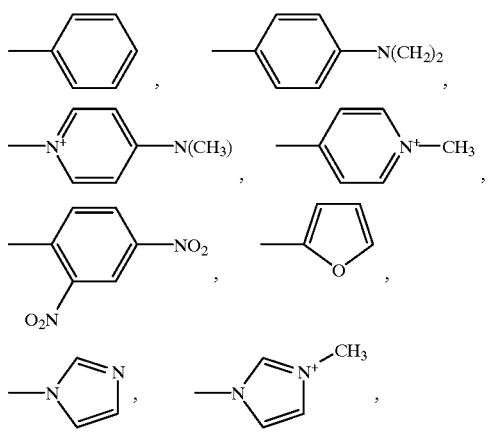

or related derivatives.

Preferred protected thiol compounds of the $sp^2$ carbon thiol protective type include the following non-limiting examples:

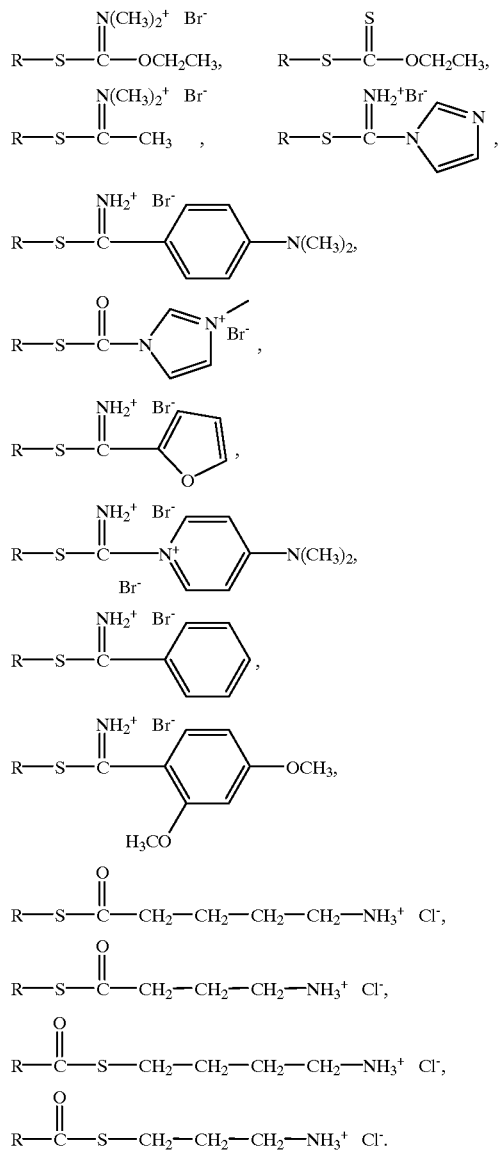

sp³ Carbon Protecting Groups

The protecting groups of the present invention may comprise an $sp^3$ carbon moiety wherein the divalent sulfur atom is bonded on one side to the cosmetic active and on the other side to a $sp^3$ carbon atom. Protecting groups of the $sp^3$ carbon type that are suitable for the present invention include those of the thioether type,

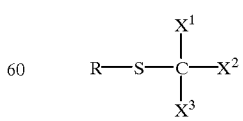

(I)

including the monothioacetal (II. $X^1$=H), monothioketal (II. $X^1$, $X^2$=H), monothioortho ester is (III) and monothioorthocarbonate (IV) type, (II)

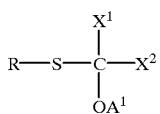

(III)

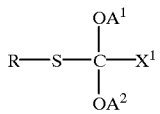

(IV)

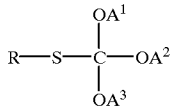

the dithioacetal (V. $X^1$=H), dithioketal (V. $X^1$, $X^2$=H), dithioorthoester (VI) and dithioorthocarbonate (VII) type, (V)

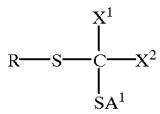

(VI)

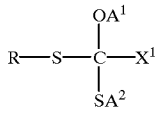

(VII)

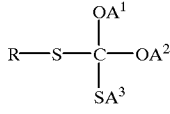

the trithioorthoester type (VIII), (VIII)

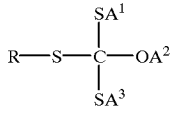

the thiohemiaminal (IX), monothioorthoamide (X) and dithioorthoamide (XI) type, (IX)

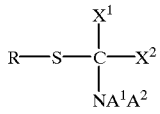

(X)

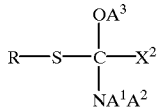

(XI)

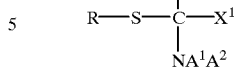

and related classes wherein $X^1$, $X^2$, $X^3$ represent, independently from one another, electron withdrawing, electron neutral, or electron donating groups with Hammett sigma para values between −1.0 and +1.5 which can be non-ionic, zwitterionic, cationic or anionic comprising for example C-linked groups of the classes defined below as $A^1$, $A^2$, $A^3$; S-linked groups including $SA^1$, SCN, $SO_2A^1$, $SO_3A^1$, $SSA^1$, $SOA^1$, $SONA^1A^2$, $SO_2NA^1A^2$, $SNA^1A^2$, $S(NA^1)A^2$, $S(O)(NA^1)A^2$, $SA^1(NA^2)$; O-linked groups including $OA^1$, $OOA^1$, OCN, $ONA^1A^2$; N-linked groups including $NA^1A^2$, $NA^1A^2A^{3+}$, NC, $NA^1OA^2$, $NA^1SA^2$, NCO, NCS, $NO_2$, $N=NA^1$, $N=NOA^1$, $NA^1CN$, $N=C=NA^1$, $NA^1NA^2A^3$, $NA^1NA^2NA^3A^4$, $NA^1N=NA^2$; other miscellaneous groups including COHal, $CON_3$, $CONA^1_2$, $CONA^1COA^2$, $C(=NA^1)NA^1A^2$, CHO, CHS, CN, NC, Hal, and derived groups that connect one or more of $X^1$, $X^2$, $X^3$, $X^4$, $X^5$ via a ring system. Hal is F, Cl, Br, or I.

For the thioether class, as defined above, at least one of $X^1$, $X^2$, or $X^3$ groups is electron donating such that the sum of the Hammett sigma para values for $X^1$, $X^2$, $X^3$ is negative for this class.

$A^1, A^2, A^3, A^4$ represent, independently from one another, a monovalent group which can be the cosmetic active group, R, or H or any of the following: a straight, branched or mono- or poly- cyclic aliphatic, mono or polyunsaturated alkyl, aryl, heteroalkyl, heteroaliphatic or heteroolefinic system including 1 to 30 carbon atoms together with 0–15 heteroatoms, especially O, N, S, P, Si, and can incorporate one or more substituents including, but not limited to, poly or per fluoro substitution.

H is hydrogen, O is oxygen, N is nitrogen, C is carbon, S is sulfur, Cl is chlorine, Br is bromine, I is iodine, F is fluorine, R is any cosmetic active, functional group or benefit agent as described herein below.

Preferred electron donating substituents for $X^1$, $X^2$, $X^3$ are aromatic or heteroaromatic derivatives which include the following non-limiting examples:

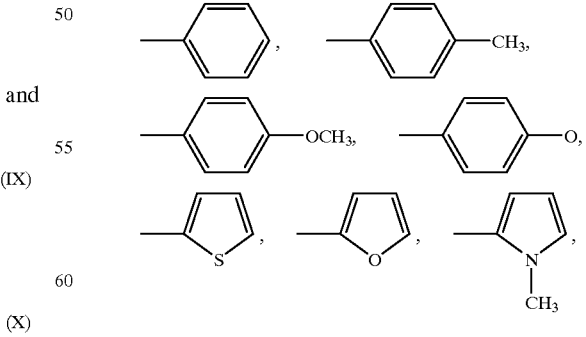

plus other related derivatives.

Preferred protected thiol compounds chosen from classes I through XI above include the following non-limiting examples:

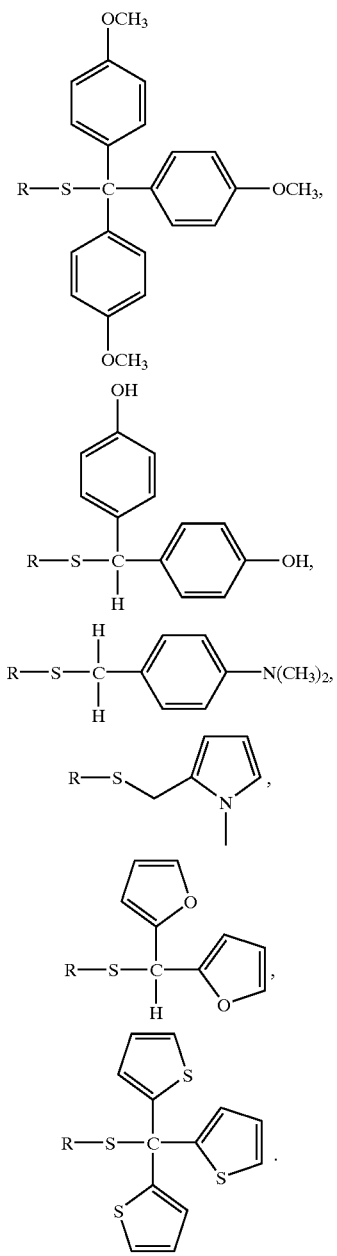

The present invention also includes organosulfur molecular "hooks" wherein the potential cosmetic thiol is bonded directly to an sp³ carbon atom that is part of a group capable of undergoing heterolytic β-elimination, the reversal of Michael Addition reactions, to liberate a thiol. Suitable sp³ carbon groups capable of undergoing heterolytic β-elimination are represented in the compounds, (V)

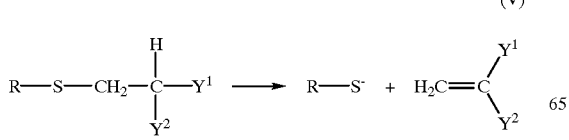

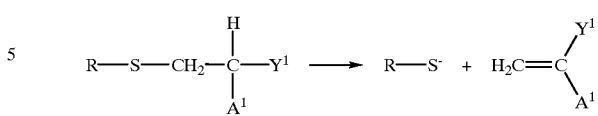

wherein $Y^1$ and $Y^2$ represent, independently from one another, electron withdrawing substituents with a combined Hammett sigma para value more positive than 0.10. Such electron withdrawing substituents include the following non-limiting examples: $NO_2$, CN, $COOA^1$, $CONA^1A^2$, $C(O)A^1$, $SO_2A^1$, $SO_2OA^1$, NO, COHal, $CON_3$, $CONA^1A^2$, $CONA^1COA^2$, $C(=NA^1)NA^2A^3$, $C(S)A^1$, NC, SCN, $SO_2A^1$, $SO_3A^1$, $SOA^1$, $SONA^1A^2$, $SO_2NA^1A^2$, $SNA^1A^2$, $S(NA^1)A^2$, $S(O)(NA^1)A^2$, $NA^1A^2A^{3+}$, $SA^1A^2+$ and aromatic and heteroaromatic derivatives.

Some non-limiting examples of aromatic and heteroaromatic electron withdrawing groups for $Y^1$ and $Y^2$ include the following:

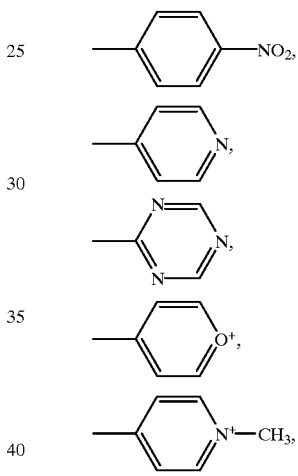

plus other related derivatives.

Preferred hook compounds that are capable of undergoing heterolytic β-elimination, the reversal of Michael Addition reactions, to liberate a thiol include the following non-limiting examples:

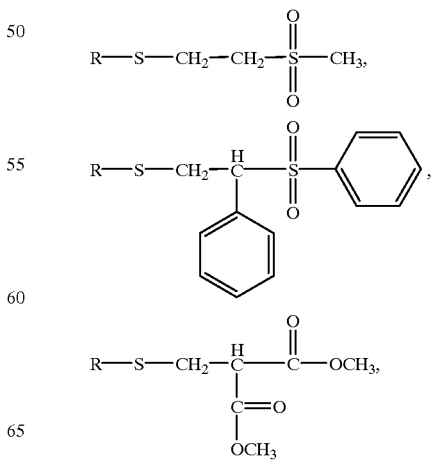

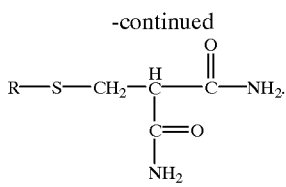

The present invention also includes cases wherein the cosmetic thiol is protected by being bonded directly to an $sp^3$ carbon atom that is incorporated within a ring structure. Suitable $sp^3$ carbon ring systems are represented by the following,

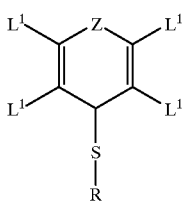

(VII)

wherein Z is O, NAk, S, $(CH_2)_{0-2}$ or

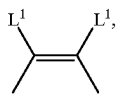

$L^1$ is $A^1$ or part of a 5 to 7 membered fused ring system. The above ring system(s) can carry any substituents. Specific examples of $sp^3$ carbon ring compounds covered by the present invention include the following non-limiting examples:

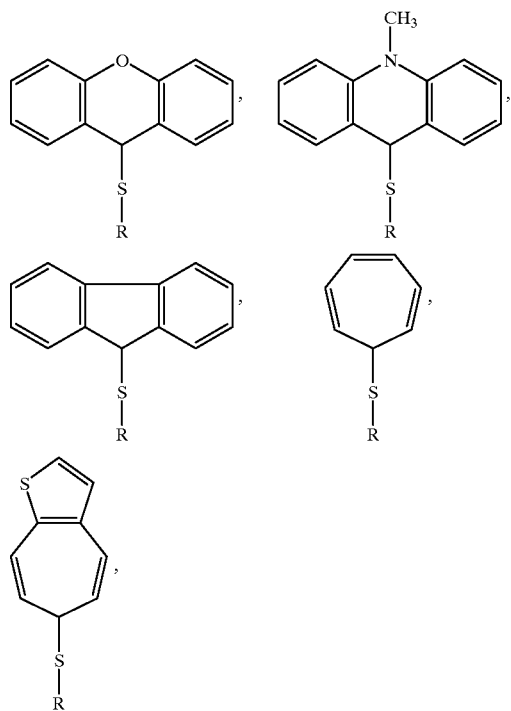

and other related derivatives.

$A^1, A^2, A^3$, represent, independently from one another, a monovalent group which can be the cosmetic active group, R, or H or any of the following: a straight, branched or mono- or poly- cyclic aliphatic, mono or polyunsaturated alkyl, aryl, heteroalkyl, heteroaliphatic or heteroolefinic system including 1 to 30 carbon atoms together with 0–15 heteroatoms, especially O, N, S, P, Si, and can incorporate one or more substituents including, but not limited to, poly or per fluoro substitution.

H is hydrogen, O is oxygen, N is nitrogen, C is carbon, S is sulfur, Cl is chlorine, Br is bromine, I is iodine, F is fluorine, R is any cosmetically active functional group or benefit agent as described herein below.

Metal Based Protecting Groups

The molecular "hooks" of the present invention comprise a divalent sulfur atom that is bonded on one side to the cosmetic active and on the other side to an alkaline earth metal, transition metal or a representative metal in groups IIA, IIIA, IVA, VA, VIA, VIIA, VIII, IB, IIB, IIIB, IVB, VB, VIB, and VIIB of the periodic table of the elements including Mg, Ca, Sr, Ba, La, Ti, Zr, V, Cr, Mo, W, Mn, Fe, Co, Rh, Ni, Pd, Pt, Cu, Ag, Au, Zn, In, Sn, and Bi. Protected thiol compounds comprising such heavy metal mercaptides are represented by the following:

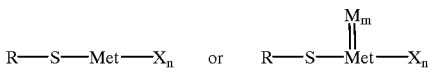

wherein Met is an alkaline earth metal, transition metal or a representative metal in groups IIA, IIIA, IVA, VA, VIA, VIIA, VIII, IB, IIB, IIIB, IVB, VB, VIB, and VIIB of the periodic table of the elements including Mg, Ca, Sr, Ba, La, Ti, Zr, V, Cr, Mo, W, Mn, Fe, Co, Rh, Ni, Pd, Pt, Cu, Ag, Au, Zn, In, Sn, and Bi. Also, wherein n and m are zero or integers such that 1+2m+n equals the valency of Met.

X represents independent electron withdrawing, electron neutral or electron donating groups with Hammett sigma para values between −1.0 and +1.5 which can be non-ionic, zwitterionic, cationic or anionic comprising for example C-linked groups of the classes defined below as $A^1, A^2, A^3$; S-linked groups including $SA^1$, SCN, $SO_2A^1$, $SO_3A^1$, $SSA^1$, $SOA^1$, $SONA^1A^2$, $SO_2NA^1A^2$, $SNA^1A^2$, $S(NA^1)A^2$, $S(O)(NA^1)A^2$, $SA^1(NA^2)$; O-linked groups including $OA^1$, $OOA^1$, OCN, $ONA^1A^2$; N-linked groups including $NA^1A^2$, $NA^1A^2A^{3+}$, NC, $NA^1OA^2$, $NA^1SA^2$, NCO, NCS, $NO_2$, $N=NA^1$, $N=NOA^1$, $NA^1CN$, $N=C=NA^1$, $NA^1NA^2A^3$, $NA^1NA^2NA^3A^4$, $NA^1N=NA^2$; other miscellaneous groups including COHal, $CON_3$, $CONA^1{}_2$, $CONA^1COA^2$, $C(=NA^1)NA^1A^2$, CHO, CHS, CN, NC, Hal, and derived groups that connect one or more of $X^1, X^2, X^3, X^4, X^5$ via a ring system. Hal is F, Cl, Br, or I.

$A^1, A^2, A^3, A^4$ represent, independently from one another, a monovalent group which can be the cosmetic active group, R, or H or any of the following: a straight, branched or mono- or poly- cyclic aliphatic, mono or polyunsaturated alkyl, aryl, heteroalkyl, heteroaliphatic or heteroolefinic system including 1 to 30 carbon atoms together with 0–15 heteroatoms, especially O, N, S, P, Si, and can incorporate one or more substituents including, but not limited to, poly or per fluoro substitution.

M is a divalent group such as O, S, $NA^1$ or $CA^1A^2$.

H is hydrogen, O is oxygen, N is nitrogen, C is carbon, S is sulfur, Cl is chlorine, Br is bromine, I is iodine, F is fluorine, B is boron, Al is aluminum, Si is silicon, N is nitrogen, Mg is magnesium, Ca is calcium, Sr is strontium, Ba is barium, La is lanthanum, Ti is titanium, Zr is zirconium, V is vanadium, Cr is chromium, Mo is molybdenum, W is tungsten, Mn is manganese, Fe is iron, Co is cobalt, Rh is rhodium, Ni is nickel, Pd is palladium, Pt is platinum, Cu is copper, Ag is silver, Au is gold, Zn is zinc, In is indium, Sn is tin, Bi is bismuth, and R is any cosmetic active, functional group or benefit agent as described herein below.

Also wherein at least one substituent, X, or the cosmetic active, R, contains salt forming or water solubilizing groups including, but not limited to, COO—, $SO_3$—, $NH_3^+$, OH, $COOA^1$, $(CH_2CH_2O)_nA^1$, $CONA^1A^2$, $OSO_3$—, $OPO_3H^-$, $NA^1A^2A^{3+}$, and the like.

Preferred metal based protecting groups of the present invention include, but are not limited to, the following examples,

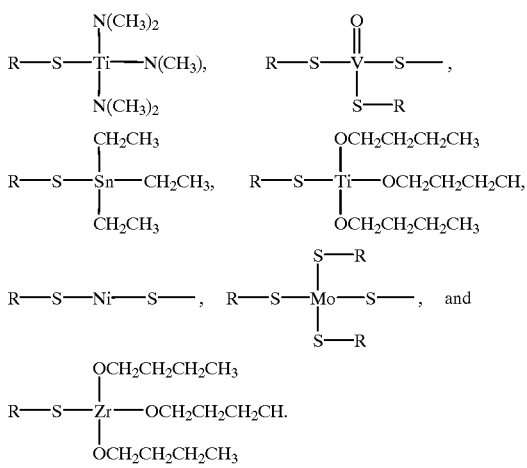

Non-metal and metalloid based Protecting Groups

The molecular "hooks" of the present invention comprise a divalent sulfur atom that is bonded on one side to the cosmetic active and on the other side to a representative non-metal or metalloid atom including boron, aluminum, silicon, germanium, nitrogen, phosphorus, sulfur, selenium, antimony, and tellurium. Molecular "hooks" whereby a divalent sulfur atom of a potential cosmetic thiol is bonded directly to these representative non-metals and metalloids are represented by the following:

or

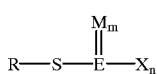

wherein E is a representative non-metal or metalloid element including B, Al, Si, Ge, N, P, S, Se, Sb, and Te. Also, wherein n and m are zero or integers such that 1+2m+n equals the valency of E.

X represents independent electron withdrawing, electron neutral or electron donating groups with Hammett sigma para values between −1.0 and +1.5 which can be non-ionic, zwitterionic, cationic or anionic comprising for example C-linked groups of the classes defined below as $A^1, A^2, A^3$; S-linked groups including $SA^1$, SCN, $SO_2A^1$, $SO_3A^1$, $SSA^1$, $SOA^1$, $SONA^1A^2$, $SO_2NA^1A^2$, $SNA^1A^2$, $S(NA^1)A^2$, $S(O)(NA^1)A^2$, $SA^1(NA^2)$; O-linked groups including $OA^1$, $OOA^1$, OCN, $ONA^1A^2$; N-linked groups including $NA^1A^2$, $NA^1A^2A^{3+}$, NC, $NA^1OA^2$, $NA^1SA^2$, NCO, NCS, $NO_2$, $N=NA^1$, $N=NOA^1$, $NA^1CN$, $N=C=NA^1$, $NA^1NA^2A^3$, $NA^1NA^2NA^3A^4$, $NA^1N=NA^2$; other miscellaneous groups including COHal, $CON_3$, $CONA^1_2$, $CONA^1COA^2$, $C(=NA^1)NA^1A^2$, CHO, CHS, CN, NC, Hal, and derived groups that connect one or more of $X^1, X^2, X^3, X^4, X^5$ via a ring system. Hal is F, Cl, Br, or I.

M is a divalent group such as O, S, $NA^1$ or $CA^1A^2$.

$A^1, A^2, A^3, A^4$ represent, independently from one another, a monovalent group which can be the cosmetic active group, R, or H or any of the following: a straight, branched or mono- or poly- cyclic aliphatic, mono or polyunsaturated alkyl, aryl, heteroalkyl, heteroaliphatic or heteroolefinic system including 1 to 30 carbon atoms together with 0–15 heteroatoms, especially O, N, S, P, Si, and can incorporate one or more substituents including, but not limited to, poly or per fluoro substitution.

H is hydrogen, O is oxygen, N is nitrogen, C is carbon, S is sulfur, Cl is chlorine, Br is bromine, I is iodine, F is fluorine, B is boron, Al is aluminum, Si is silicon, Ge is germanium, N is nitrogen, P is phosphorus, Te is tellurium, and R is any cosmetic active, functional group or benefit agent as described herein below.

Preferred thiol protective systems utilizing non-metals and metalloids of the present invention include, but are not limited to, the following examples,

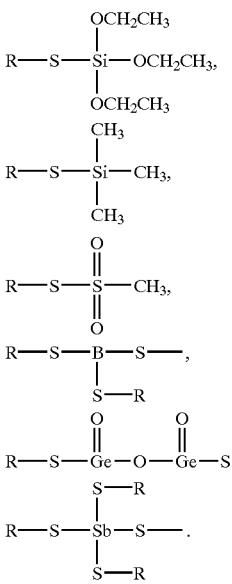

Energy-sensitive Protecting Groups

The topical compositions of the present invention may also comprise a protected thiol compound wherein the protecting group is energy-sensitive. Protected thiol compounds comprising energy-sensitive protecting groups are chemically stable in solution. Such potential thiols are protected until a suitable source of energy is applied to the composition. Upon application of a suitable energy source, the energy-sensitive protecting groups become labile, thereby releasing the reactive thiol. Typically, the energy source will be light. Once the thiols are released, they are capable of reacting with amino acid residues present in keratinaceous substrates to enable durable cosmetic benefits.

As mentioned above, the protected thiols are activated by applying a suitable energy source to the composition, i.e., irradiation, which converts the photoactivatable protected thiol compounds to fully reactive thiol compounds. The byproducts of the energy activation of the protecting group will usually be removed from the substrate by washing.

Many different energy-sensitive groups can be employed for protecting thiols used in the topical compositions of the present invention. Typically, the thiol groups are protected with a photoactivatable protecting group that is capable of liberating or releasing the reactive thiol by irradiation. The properties and uses of photoreactive compounds have been reviewed. See McCray et al, 1989, *Ann. Rev. Biophys. Chem.* 18:239–270, which is incorporated herein by reference. The photosensitive groups will preferably be activatable by low energy ultraviolet or visible light. Many, although not all, of the energy-sensitive protecting groups are aromatic compounds. Suitable photoremovable protecting groups are also described in, for example, Patchornik, 1970, *J. Am. Chem. Soc.* 92:6333, and Amit et al, 1974, *J. Org. Chem.* 39:192, which are incorporated herein by reference. More preferably, the energy-sensitive protecting group will be a nitrobenzylic compound, such as o-nitrobenzyl or benzylsulfonyl groups. Suitable examples include 6-nitroveratryloxycarbonyl (NVOC); 6-nitropiperonyloxycarbonyl (NPOC); alpha, alpha-dimethyldimethoxybenzyloxycarbonyl (DDZ), methyl 6-nitroveratryloxycarbonyl (MenVOC), methyl-6-nitropiperonyloxycarbonyl (MeNPOC), or 1-pyrenylmethyl. The energy-sensitive protecting group may also be of the silyl type as described in Pirrung and Lee, 1993, *J. Org. Chem.* 58:6961–6963 and Pirrung and U.S. Pat. No. 5,486,633, issued to Lee, both incorporated by reference herein. Suitable examples include (hydroxystyryl)dimethylsilyl (HSDMS) and (hydroxystyryl)diisopropylsilyl (HSDIS).

Clearly, many energy-sensitive protecting groups are suitable for use in the present method. Some examples of acceptable energy-sensitive protecting groups are presented in Table 1, below, together with their corresponding wavelengths for deprotection.

TABLE 1

Energy-sensitive Protecting Groups

| Group | Deprotection Wavelength |
|---|---|
| 6-nitroveratryloxycarbonyl (NVOC) | UV (300–350 nm) |
| dimethyldimethoxybenzyloxycarbonyl (DDZ) | UV (280–300 nm) |
| nitrobenzyloxycarbonyl (NBOC) | UV (300–350 nm) |
| 5-bromo-7-nitroindolinyl (BNI) | UV (420 nm) |
| O-hydroxy-alpha-methyl-cinnamoyl (HMC) | UV (300–350 nm) |
| 2-oxymethylene anthraquinone (OMA) | UV (350 nm) |

The composition containing the cosmetic active protected with the energy-sensitive group may be activated with energy both prior or during usage. For instance, the energy source may be applied to the composition for a sufficient time period to activate the energy sensitive protecting group either before, during or after the composition is applied to the substrate. The energy source may include various types of electromagnetic radiation including ultraviolet, visible, near infrared, infrared, far infrared or microwave. In a preferred embodiment, the radiation is UV, near IR or visible light.

Examples of suitable protecting groups that are capable of undergoing photochemical or thermal thiol deprotection include, but are not limited to, the following:

I. 2-Nitrobenzyl derivatives

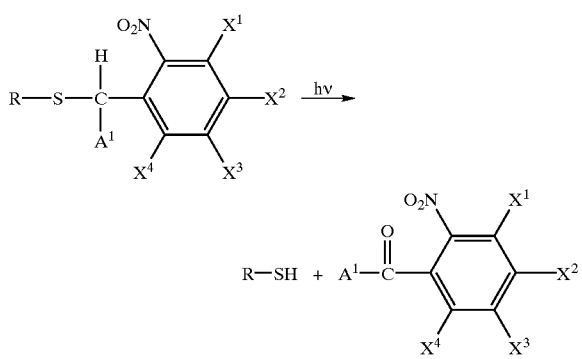

Examples:

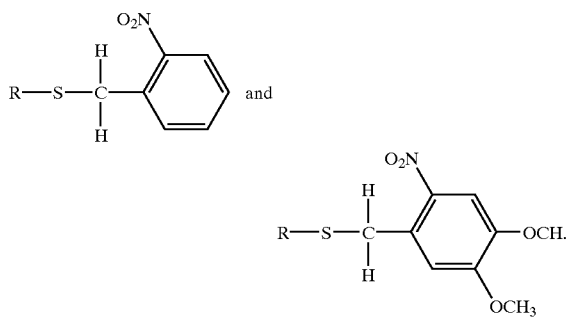

II. 2-Nitrobenzyloxycarbonyl Derivatives

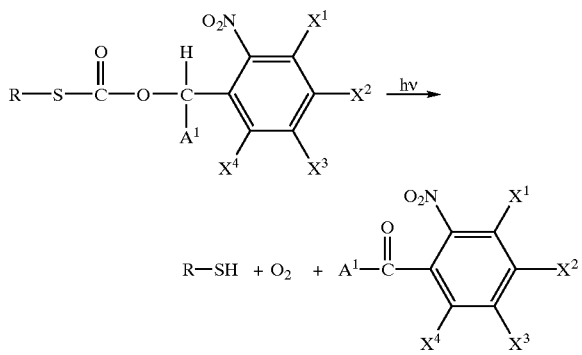

Examples:

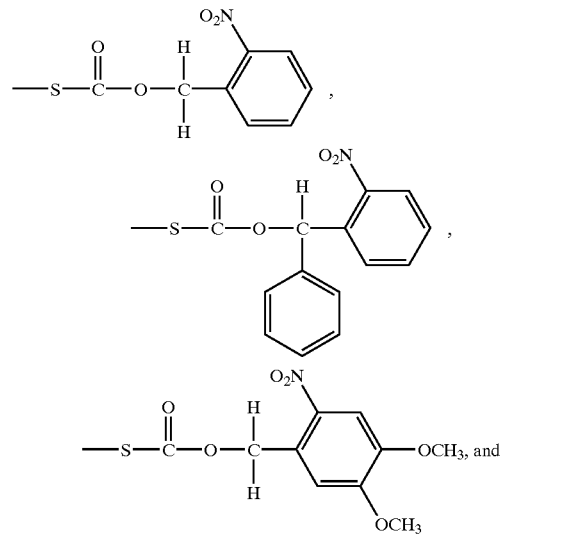

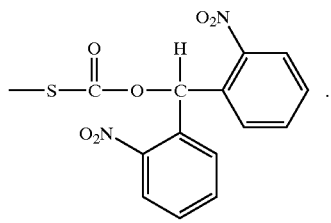

III. Benzyloxycarbonyl Derivatives

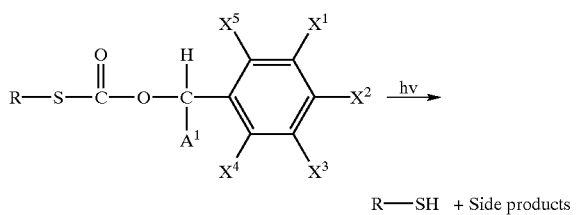

$$R\text{---}SH + \text{Side products}$$

Examples:

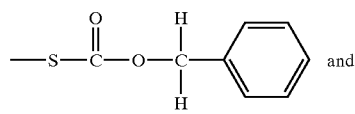

and

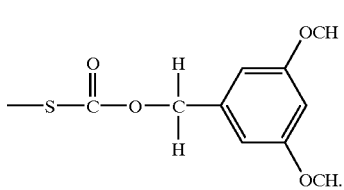

IV. α,α-Dimethylbenzyloxycarbonyl Derivatives

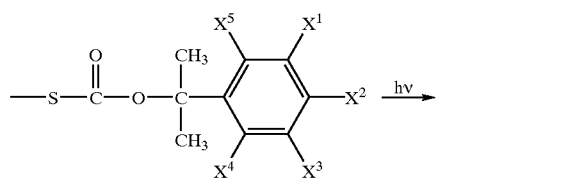

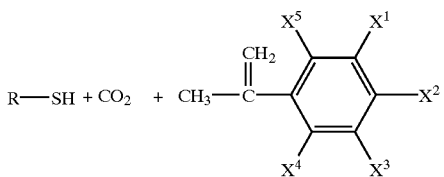

Example:

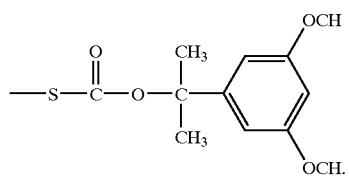

V. 3-Nitrophenyloxycarbonyl Derivatives

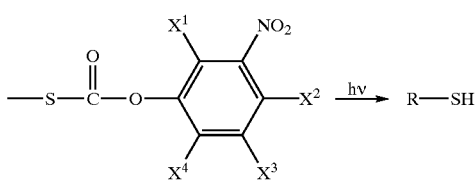

Example:

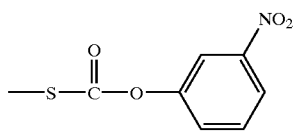

VI. Phenacyl Derivatives

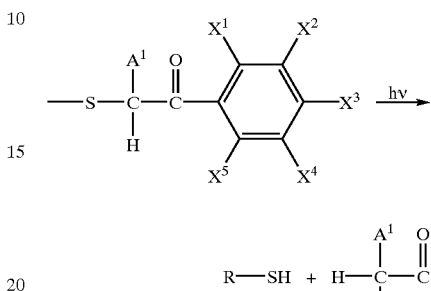

Examples:

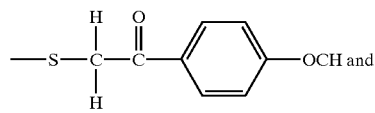

and

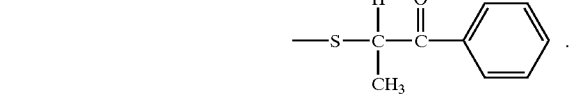

VII. tert-Butyloxycarbonyl Derivatives

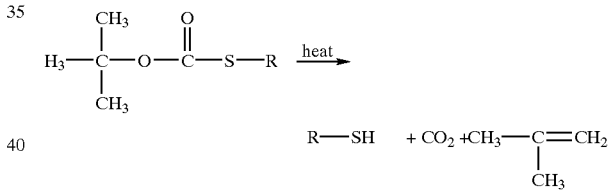

$X^1$, $X^2$, $X^3$, $X^4$, and $X^5$ can be selected from electron withdrawing, electron neutral, or electron donating groups with Hammett sigma para values between −1.0 and +1.5 which can be non-ionic, zwitterionic, cationic or anionic comprising for example C-linked groups of the classes defined below as $A^1$, $A^2$, $A^3$; S-linked groups including $SA^1$, SCN, $SO_2A^1$, $SO_3A^1$, $SSA^1$, $SOA^1$, $SONA^1A^2$, $SO_2NA^1A^2$, $SNA^1A^2$, $S(NA^1)A^2$, $S(O)(NA^1)A^2$, $SA^1(NA^2)$; O-linked groups including $OA^1$, $OOA^1$, OCN, $ONA^1A^2$; N-linked groups including $NA^1A^2$, $NA^1A^2A^{3+}$, NC, $NA^1OA^2$, $NA^1SA^2$, NCO, NCS, $NO_2$, $N\text{=}NA^1$, $N\text{=}NOA^1$, $NA^1CN$, $N\text{=}C\text{=}NA^1$, $NA^1NA^2A^3$, $NA^1NA^2NA^3A^4$, $NA^1N\text{=}NA^2$; other miscellaneous groups including COHal, $CON_3$, $CONA^1_2$, $CONA^1COA^2$, $C(\text{=}NA^1)NA^1A^2$, CHO, CHS, CN, NC, Hal, and derived groups that connect one or more of $X^1$, $X^2$, $X^3$, $X^4$, $X^5$ via a ring system;

$A^1$, $A^2$ represent, independently from one another, a monovalent group which can be the cosmetic active group, R, or H or any of the following: a straight, branched or mono- or poly-cyclic aliphatic, mono or polyunsaturated alkyl, aryl, heteroalkyl, heteroaliphatic or heteroolefinic system including 1 to 30 carbon atoms together with 0–15 heteroatoms, especially O, N, S, P, Si, and can incorporate one or more substituents including, but not limited to, poly or per fluoro substitution.

Mono or Multivalent Cosmetically Active Functional Group

The mono or multivalent cosmetically active functional, R, suitable for inclusion in the present invention may be any compound that imparts one or more visual, tactile or other cosmetic beneficial effects on proteinaceous materials such as keratin, i.e., hair, animal fur or wool. Any cosmetic compound may be included as a functional group in the compositions of the present invention as long as the compound can be modified to contain at least one divalent sulfur atom linked to a suitable protecting group as described herein.

Suitable functional groups that can be protected as thiol derivatives include but are not limited to antimicrobial compounds, UV-absorbing compounds, skin conditioning agents, hair conditioning agents, hair repair agents, hair styling agents, hair dyes, scalp treatment agents, anti-inflammatory compounds, antioxidants, dyes and coloring agents, perfumes, oral care actives, skin moisturizers, pharmaceutical agents, antidandruff agents, insect repellents, moisturizers, humectants, pearlescent and/or opacifying materials, fabric care actives, pet grooming actives, fabric anti-wrinkling agents, shrink-resistant actives, laundry care actives, hard surfaces actives, textile actives, textile dyes, water-proofing agents, cationic polymers, cationic surface modifiers, hydrophobic surface modifiers, anionic surface modifiers, absorbents, antifungal agents, insecticidal agents, textile color guards, nail actives such as enamel and polish, eyelash actives and mascara, antiperspirant and deodorant actives, anti-acne actives, odor control actives, fluorescent actives, bleaching agents, enzymes, antibodies, dispersing aids, emollients, stabilizers, anti-static agents, anti-seborrhea agents, optical brighteners, fluorescent dyes, softeners, cross-linking agents, photobleaches, bactericides, and mixtures thereof.

Examples of suitable antimicrobials which can be protected as thiol derivatives include but are not limited to derivatives of phenol, cresol, hydroxybenzoates, Triclosan®, Tricarban®, chlorhexidine, metal salts (e.g. zinc citrate, sodium zinc citrate, zinc pyridinethione, and stannous pyrophosphate) sanguinarine extract, metronidazole, quaternary ammonium compounds (chlorhexidine digluconate, hexetidione, octenidine, alexidine), halogenated bisphenolic compounds such as 2,2'-methylenebis-(4-chloro-6-bromophenol), and salicylanilide.

Examples of suitable UV-absorbing materials which can be protected as thiol derivatives include but are not limited to derivatives of benzoates, oxybenzones, cinnamic acid, PARSOL MCX esters, benzotriazoles, and benzophenones.

Examples of suitable skin conditioners or moisturizers which can be protected as thiol derivatives, include but are not limited to derivatives of alpha-hydroxy acids, polyols, hyaluronic acid, petrolatum, vegetable oils, esters of fatty acids, and mineral oil. Such skin conditioners or moisturizers are bound to the velus hairs present on the skin, and not the skin directly, to achieve the long lasting skin benefits.

Examples of suitable anti-inflammatory agents which can be protected as thiol derivatives include but are not limited to corticosteroids or salicylates.

Examples of suitable antioxidants which can be protected as thiol derivatives include but are not limited to ascorbates and gallates.

Examples of suitable hair conditioners which can be protected as thiol derivatives include but are not limited to intact or modified proteins, such as hydrolyzed keratin, collagen, elastin, hemoglobin, silk, rice, soy, wheat protein, corn, fibronectin, reticulum, serum protein, wheat gluten, peptides and peptide derivatives; amino acids; hydroxylated fats; glycinates; silicone polymers, such as siloxane gums and resins, volatile or non-volatile silicone oils, amino- (or other) functional silicones, and other silicone-containing polymers; hydrocarbon based conditioners including $C_8$–$C_{30}$ alkyl, alkenyl, modified alkyl or modified alkenyl, branched alkyl and branched alkenyl groups as well as long chain alkyl groups that are ethoxylated or substituted with various non-ionic, cationic or anionic functional groups including quats, amines, amides, esters, hydroxyls, carboxylates, and the like; polysaccharides or monosaccharides, and alkyl cationic conditioning polymers such as cationic derivatives of guar gum and cellulose ether derivatives; poly(ethyleneoxides) and alkyl capped poly (ethyleneoxides) of molecular weights ranging from 100 to 10,000,000; and herb or other plant extracts, essential oils etc.

Examples of suitable hair styling agents which can be protected as thiol derivatives include but are not limited to film-forming polymers such as polyvinylpyrrolidone/vinyl acetate copolymer; styling copolymers comprising silicone macromonomers, U.S. Pat. Nos. 5,618,524 and 5,658,557, cationic polymers, such as those disclosed in GB-A-2161172 (Beecham), GB-A-2122214 (Unilever) and GB-A-2050166 (L'Oreal); and hydrocarbon polymers, such as polyisobutylene; perfluoro-aliphatic and perfluoro-aromatic compounds.

Examples of suitable dyes and coloring agents which can be protected as thiol derivatives include but are not limited to phenol, naphthols, acid dyes, azo derivatives; vegetable dyes, metallized dyes, nitrobenzene dyes, quinone-imine dyes, basic dyes, quaternary dyes, and oxidation dyes.

Examples of suitable fragrances that can be protected as thiol derivatives include but are not limited to phenols such as menthyl salicylate, thymol, and vanillin.

Examples of suitable cationic polymers that can be protected as thiol derivatives include but are not limited to derivatives of quaternary ammonium salts of hydroxyethylcellulose, cationic copolymers of acrylic acid and acrylamide, cationic guar polymers, copolymers of vinylimidazolium methochloride and vinylpyrrolidone, polyethylenimines, and other cationic polymers and resins known to those skilled in the art.

Examples of suitable oral care active agents that can be protected as thiol derivatives include but are not limited to anti-caries agents such as amine fluorides, monosodium fluorophosphate, casein; plaque buffers such as urea, calcium lactate, calcium glycerophosphate; anti-plaque agents; agents for alleviating sensitive teeth, e.g. potassium and strontium salts, particularly those of carboxylic acids; materials that form films and block pores; oral pharmaceutical actives, (e.g. ibuprofen, flurbiprofen, aspirin and indomethacin); biomolecules such as peptides, antibodies and enzymes; anti-tartar agents; agents for treating bad breath such as zinc salts; and anti-calculus agents (e.g. alkali metal pyrophosphates, hypophosphite-containing polymers, organic phosphonates, and phosphocitrates).

Examples of suitable pharmaceutical agents that can be protected as thiol derivatives include but are not limited to medicinal agents, metabolic agents and other therapeutic agents of benefit in treating the human body.

Examples of antidandruff agents that can be protected as thiol derivatives include but are not limited to zinc pyridinethione, Octopirox®, climbazole and itroconazole.

An example of odor control actives that can be protected as thiol derivatives include the class of cyclodextrins. In addition to trapping odors on the substrate, the cyclodextrins can plausibly be utilized to deliver cosmetic actives molecules to the substrate such as perfumes that can be liberated slowly.

Other non-limiting classes of beneficial cosmetic actives include sealants, binders, resins, adhesives, waxes, drying oils, varnishes, and latex finishes which comprise urethanes, polysulfides, acrylics, butyl polymers, maleated oils, cellulosics, starches etc.

The mono or multivalent cosmetically active functional preferably used in the present compositions is dependent on the product form desired. Hair care compositions preferably use hair conditioners, hair styling agents, dyes and coloring agents, sunscreens, fragrances, antidandruff agents, or mixtures thereof as the functional group. Preferable functional groups in textile care compositions include dyes and coloring agents, odor control actives, sealants, fragrances, and mixtures thereof. Cosmetic compositions preferably comprise dyes and coloring agents, sealants, resins, varnishes, latex finishes, and mixtures thereof. Oral care compositions preferably comprise anti-caries agents, plaque buffers, anti-plaque agents, agents for alleviating sensitive teeth, materials that form films and block pores, oral pharmaceutical actives, biomolecules, anti-tartar agents, agents for treating bad breath, anti-calculus agents, and mixtures thereof as functional groups. Pharmaceutical composition preferably select mono or multivalent cosmetically active functional groups from the group consisting of medicinal agents, metabolic agents, therapeutic agents, anti-inflammatory compounds, and mixtures thereof. Animal care composition preferably comprise antimicrobial agents, insect repellents, grooming actives, and mixtures thereof as functional groups.

OPTIONAL ACTIVATING MECHANISMS

As explained above, the molecular 'hooks' of the present invention may be activated via a number of mechanisms either before, during or after the application of the topical compositions containing the protected thiol to the substrate. Various embodiments of the present invention are systems which comprise both the topical composition herein with an activating mechanism.

Such activation could be achieved via hydrolysis by the use of a mechanism to manipulate the pH of the environment surrounding the compound. Such pH adjusting mechanisms may include acidic or alkaline solutions. Whether acidic or alkaline mechanisms are required is dependent on the protecting group used. Hydrolysis may also be achieved via simply mixing the compound, delivered in its purified form or from a non-aqueous solution, with water.

Furthermore, the molecular 'hook' could be activated by coming in contact with a suitable nucleophile. Such nucleophiles include, but are not limited to, nitrogen-containing functional groups, for example amines, oxygen-containing functional groups, for example hydroxyl groups, phosphorus-containing functional groups, for example phosphines, and sulfur-containing functional groups, for example thiol groups and sulfites. For instance, the solution containing the 'hook' compound could be inter-mixed with a separate solution containing a nucleophile including reducing agents such as ammonium thioglycolate or sodium bisulfite, either before, during or after application of the compound to the substrate.

Conversely, the 'hook' compound could be activated by nucleophilic groups present in the substrate itself as in the case of hair that has been reduced or cold waved, i.e. hair that has been treated with a reducing agent either prior to or simultaneous to the application of the 'hook' compound. The resulting activated thiol 'hook' could then react directly as a nucleophile with keratinaceous disulfides or oxidatively with the nucleophilic groups present in the substrate, e.g. with free thiol groups that were formed during cold waving or reduction. Of course, the latter process could be accelerated or enhanced via the addition of oxidation reagents, i.e. peroxide as in the neutralization step of cold waving of hair.

The activation could also be accented via heat or a suitable energy source. For instance, the energy source could be applied to the composition for a sufficient time period to activate the protecting group either before, during or after the composition is applied to the substrate. The energy source may include various types of electromagnetic radiation including ultraviolet, visible, near infrared, infrared, far infrared or microwave radiation.

Other various adjuncts that could possibly influence the activation and/or the performance of the "hook" compounds of the present invention include, but are not limited to, (i) Lewis acids such as zinc acetate, tin chloride, zinc chloride, zinc stearate, titanium ethoxide, and aluminum tosylate, metal salts such as zinc sulfate, and magnesium sulfate, (ii) chelators such as tetrasodium EDTA, disodium EDTA, (iii) ionic species capable of ion-pairing including anions, cations, quats, amphoterics zwitterions etc, (iv) dispersing aids such as anionic surfactants, non-ionic surfactants, anionic surfactants, amphoteric surfactants, and zwitterionic surfactants, (v) keratin swelling aids such as ammonia, amines, urea, phosphoric acid, acetic acid and other swelling aids known to those skilled in the art, and (vi) solvent systems wherein the individual solvent molecules are nucleophiles themselves as defined above.

Another embodiment of the present invention comprises a kit comprising the system comprising the topical compositions of the present invention and either a pH manipulating mechanism or a nucleophile mechanism, and a package comprising a first and second chamber; wherein the topical composition is packaged in and delivered out of one chamber and the activation mechanism is packaged in and delivered out of the second chamber.

OTHER OPTIONAL INGREDIENTS

The topical composition according to the invention can also typically include an acceptable vehicle to act as a dilutant, dispersant, or carrier for the protected thiol compounds in the composition, so as to facilitate the distribution of the protected thiol compounds when the composition is applied to the keratinaceous substrate, i.e., hair, nails, wool, skin etc.

Vehicles other than water can include liquid or solid emollients, solvents, humectants, thickeners and powders. Examples of each of these types of vehicle, which can be used singly or as a mixture of one or more vehicles, are as follows:

Emollients, such as stearyl alcohol, glyceryl monoricinoleate, glyceryl monostearate, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isododecane, isocetyl alcohol, eicosanyl alcohol, behenyl alcohol, cetyl palmitate, silicone oils such as polydimethylsiloxane, cyclomethicone, di-n-butyl sebacate, isopropyl myristate, isopropyl palmitate, isopropyl stearate, butyl stearate, dimethyl malonate, polyethylene glycol, triethylene glycol, lanolin, cocoa butter, corn oil, cotton seed oil, tallow lard, olive oil, palm kernel oil, rapeseed oil, safflower seed oil, evening primrose oil, soybean oil, sunflower seed oil, avocado oil, olive oil, sesame seed oil, coconut oil, arachis oil, castor oil, acetylated lanolin alcohols, petroleum jelly, mineral oil, butyl myristate, isostearic acid, palmitic acid, isopropyl linoleate, lauryl lactate, myristyl lactate, decyl oleate, myristyl myristate;

Propellants, such as trichlorofluoromethane, dichlorodifluoromethane, dichlorotetrafluoroethane, monochlorodifluoromethane, trichlorotrifluoroethane, propane, butane, isobutane, dimethyl ether, carbon dioxide, nitrous oxide;

Solvents include, but are not limited to, ethyl alcohol, n-propanol, n-butanol, tert-butanol, ethylene glycol dimethyl ether, hexane, tetramethylurea, sulfolane, low molecular weight poly(ethylene oxide), glycerol, propylene glycol, 2-butoxyethanol, amyl alcohol, n-octanol, n-decanol, acetone, acetic acid, butyl acetate, methylene chloride, isopropanol, acetone, ethylene glycol monoethyl ether, diethylene glycol monobutyl ether, diethylene glycol monoethyl ether, dimethyl sulphoxide, dimethylformamide, tetrahydrofuran;

Powders, such as chalk, talc, fullers earth, kaolin, starch, gums, colloidal silica, sodium polyacrylate, tetraalkyl- and/ or trialkyl-arylammonium smectites, chemically modified magnesium aluminum silicate, organically modified montmorillonite clay, aluminum silicate, fumed silica, carboxyvinyl polymer, sodium carboxymethylcellulose, ethylene glycol monostearate.

The cosmetically acceptable vehicle will usually form from 10 to 99.9%, preferably from 50 to 99% by weight of the composition and can, in the absence of other cosmetic adjuncts, form the balance of the composition.

The topical compositions according to the invention may be provided in any suitable physical form, for example as low to moderate viscosity liquids, lotions, milks, mousses, dispersions, sprays, gels, foams, aerosols, and creams. These compositions may be produced by procedures well known to the skilled artisan. The cosmetic compositions can be used in various manners as other known compositions in the art including but not limited to various rinse-off and leave-on applications such as hair shampoos, skin cleansers, skin lotions, hair conditioners, styling sprays, hair mousses, two-in-one shampoos, fabric softeners, lotions, nail polishes, hair serums, hair dyes, hair waving, etc. The contact time between the cosmetic composition of the present invention and the substrate varies between 10 seconds and about 1 hour, preferably between 20 seconds and 30 minutes, more preferably between 30 seconds and 15 minutes.

The cosmetic composition of the present invention can be formulated as a fluid, lotion, fluid cream or cream having a viscosity from 500 to 100,000 mPas or above. The composition can be packaged in a suitable container to suit its viscosity and intended use by the consumer. For example, a lotion or fluid cream can be packaged in a bottle or a roll-ball applicator or a propellant-driven aerosol device or a container fitted with a pump suitable for hand or finger operation. When the composition is a cream, it can simply be stored in a non-deformable bottle or squeeze container, such as a tube or a lidded jar.

The topical product or composition of the present invention may include an activator as described above. In such a case, the inventive composition must be designed to prevent pre-mature activation of the protected thiol compound prior to use. For instance, the protected thiol compound and the activator may be placed in separate chambers in a dual chamber package, or either of the 'hook' compound or the activator can be placed within shear sensitive (or other induced release) capsules which rupture prior or during use. Alternatively, the protected thiol compound and the activator can be placed in separate packages to enable pre-mixing or sequential application by the consumer. For examples of typical dual chamber packages see PCT Application WO 96/02230, by Unilever PLC, published Feb. 1, 1996. (Herein incorporated by reference.)

Conversely, the cosmetic active of the present invention can be supplied in the purified form, i.e., as a powder, crystal, wax, gum or liquid. The purified cosmetic active could be intermixed with any of the above suitable carriers either prior to or simultaneous to the usage by the consumer. For instance, the purified cosmetic active could be placed within a compartment that is separated from the carrier by a barrier wall. Upon usage, the barrier wall could be broken, disrupted or even removed to enable the purified cosmetic active to come in contact with and inter-mix with the carrier.

The topical composition of the present invention comprises at least one of the above described protected thiol compounds, together with any additional ingredients which are normally to be found in cosmetic treatment compositions for use on hair, skin, or other substrates such as other fibers, textiles, fabrics, or the like. One or more of the protected thiol compounds may be used, the use of two or more being beneficial for example where a combination of cosmetic benefits is wanted, each derivable from a different cosmetic agent species.

While aqueous or aqueous/alcoholic solution based compositions, or possibly organic-based compositions, in which one or more protected thiol compounds are dissolved by solution are preferred, the compositions if desired or appropriate may comprise stable emulsions or dispersions of the one or more functionalized cosmetic agents which are designed to be water insoluble. In both of these cases, conventional means for achieving successful deposition and activation of the active(s) may be required. for instance, an emulsion or a dispersion could be intermixed with a separate solvent solution via a dual phase package to enable solubilization and subsequent activation during usage.

The topical composition according to the invention may include optional benefit materials and cosmetic adjuncts, as long as the benefit materials or the adjuncts do not eliminate or substantially reduce the performance of the organosulfur functionalized cosmetic agent. The additional ingredients may include, for example dyes and coloring agents, fragrances; anionic, cationic, non-ionic, amphoteric or zwitterionic surfactants; buffers, masking fragrances, dispersing agents, stabilizers, cationic polymers, perfumes, non-ionic polymers, anionic polymers, complex coacervates, complex coacervate capsules, metal salts, Lewis acids, buffering agents, particulate thickeners, polymeric thickeners, wax thickeners, oils, emollients, humectants, moisturizers, dyes, dyes and coloring agents, enzymes, antibodies, preservatives, viscosity enhancers, gelling agents, chelators, silicones or other emulsifying agents, and other common adjuvants well known to those skilled in the art.

Nonlimiting examples of anionic lathering surfactants useful in the compositions of the present invention are disclosed in McCutcheon's, *Detergents and Emulsifiers,* North American edition (1990), published by The Manufacturing Confectioner Publishing Co.; McCutcheon's, *Functional Materials*, North American Edition (1992); and U.S. Pat. No. 3,929,678, to Laughlin et al., issued Dec. 30, 1975, all of which are incorporated by reference.

A wide variety of anionic surfactants are potentially useful herein. Nonlimiting examples of anionic lathering surfactants include those selected from the group consisting of alkyl and alkyl ether sulfates, sulfated monoglycerides, sulfonated olefins, alkylaryl sulfonates, primary or secondary alkanesulfonates, alkyl sulfosuccinates, acyltaurates, acylisethionates, alkyl glyceryl ether sulfonates, sulfonated methyl esters, sulfonated fatty acids, alkyl phosphates, acylglutamates, acylsarcosinates, alkyl sulfoacetates, acylated peptides, alkyl ether carboxylates, acyllactylates, anionic fluorosurfactants, and mixtures thereof. Mixtures of anionic surfactants can be used effectively in the present invention.

Suitable nonionic surfactants include polyoxyalkylene alcohol surfactants, especially alkyl polyethyleneglycol ethers, alkyl polypropyleneglycol ethers, alkyl polyethyleneglycol esters, and alkyl polypropyleneglycol esters and mixtures thereof.

Suitable amphoteric surfactant components for use in the shampoo composition herein include those which are known for use in shampoo compositions or other personal care cleansing composition, and which contain a group that is anionic at the pH of the shampoo composition. Concentration of such surfactant components in the shampoo composition preferably ranges from about 0.5% to about 20%, preferably from about 1% to about 10%, more preferably from about 2% to about 5% by weight of the composition. Examples of amphoteric surfactants suitable for use in the shampoo composition herein are described in U.S. Pat. No. 5,104,646 (Bolich Jr. et al.), U.S. Pat. No. 5,106,609 (Bolich Jr. et al.), which descriptions are incorporated herein by reference. Examples of amphoteric detersive surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecylaminopropionate, sodium 3-dodecylaminopropanesulfonate, sodium laurylsarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "MIRANOL"™ and described in U.S. Pat. No. 2,528,378.

Other amphoteric surfactants, sometimes classified as zwitterionic surfactants, such as betaines can also be useful in the present invention. Such zwitterionics are considered as amphoterics in the present invention where the zwitterionic has an attached group that is anionic at the pH of the composition. Examples of betaines useful herein include the high alkylbetaines, such as cocodimethylcarboxymethylbetaine, cocoamidopropylbetaine, cocobetaine, laurylamidopropylbetaine, oleylbetaine, lauryldimethylcarboxymethylbetaine, lauryldimethyl-alpha-carboxyethylbetaine, cetyldimethylcarboxymethylbetaine, lauryl-bis-(2-hydroxyethyl) carboxymethylbetaine, stearyl-bis-(2-hydroxypropyl)carboxymethyl betaine, oleyldimethyl-gamma-carboxypropylbetaine, and lauryl-bis-(2-hydroxypropyl)-alpha-carboxyethylbetaine. The sulfobetaines may be represented by cocodimethyl sulfopropylbetaine, stearyldimethylsulfopropylbetaine, lauryldimethylsulfoethylbetaine, lauryl-bis-(2-hydroxyethyl)sulfopropylbetaine and the like; amidobetaines and amidosulfobetaines, wherein the $RCON(CH_2)_3$ radical is attached to the nitrogen atom of the betaine are also useful in this invention. Most preferred for use herein is cocoamidopropylbetaine.

If desired or as necessary, one or more additional benefit agents may also be included in the compositions of the invention, for example to modify the overall cosmetic benefit or combination of benefits imparted to the substrate treated with the composition. Suitable additional cosmetic benefit agents include the following:

(i) conditioning agents, i.e., materials which impart one or more visual or tactile benefits such as softness, smoothness, shine, non-flyaway, anti-static, ease of dry and/or wet combing, e.g., cationic surfactants, cationic polymers, volatile and/or non-volatile silicones or derivatives thereof, quaternary ammonium salts having at least one long chain alkyl or alkenyl group, protein hydrolysates, quaternized protein hydrolysates, perfluoropolyether materials, fatty alcohols, and mixtures thereof;

(ii) styling/setting/bodying agents, i.e., materials which give enhanced body and fell to the hair or other fibers or enable them to hold a given shape or style, e.g., various polymers, gums and resins, for example adhesive and/or resinous hydrocarbon materials such as per-alk(en)ylhydrocarbon materials, silicone/siloxane gums or resins, waxes, chitosan and derivatives, salts and complexes thereof, and mixtures thereof;

(iii) fiber straightening agents;

(iv) colourants and dyeing agents;

(v) antidandruff agents, e.g., zinc pyridinethione, Octopirox®, climbazole;

(vi) sun-protective materials, e.g. sunscreens, especially UV absorbers;

(vii) hair growth promoters or regulators, e.g. diacylglycerols, glucarolactams, glucarolactones, Minoxidol®;

(viii) moisturizers, e.g. 2-hydroxyalkanoic acids, acid soap and complexes thereof, and other emollients, occlusives, humectants;

(iX) pearlescent and/or opacifying materials;

(x) oils, e.g. silicone oils, oleic acid, hydrocarbons, isopropyl myristate, oleyl alcohol, oleates, squalene, sunflower seed oil, rapeseed oil, other plant derived oils, mineral oil;

(xi) proteins, vitamins, nutrients, stimulants, antiradicals, astringents;

(xii) herb or other plant extracts, essential oils etc.

(xiii) antimicrobial agents, e.g. antibacterial or anti-infestive agents;

(xiv) other adjunct materials commonly used in cosmetic compositions, e.g., buffering and/or pH adjusting agents, perfumes, colorings, preservatives, proteins etc.

(xv) anti-malodor agents as those disclosed to treat post-perm odors in U.S. Pat. No. 5,554,364 and EP 0610892.

(xvi) highly substantive polymers and other moieties including polyethylenimines (PEI's) such as those included within the Polymin® series supplied by BASF.

(xvii) metal salts comprising alkaline earth metals such as magnesium and calcium, transition metals such as zinc, manganese and copper, and the group IIIA metals such as Al. The use of these metal salts for hair treatment is disclosed in WO9609030 and WO9703640 where they are claimed to form metal-sulfur bonds with the hair for use in hair styling and restyling. Such metal salts could conceivably be employed to complex and interact with the cosmetic active of the present invention. Such interactions should not interfere too greatly with the performance of the cosmetic actives and could potentially positively influence the performance, i.e., metals could complex with the sulfur atom within cosmetic active and facilitate or induce activation in the form of thiol release.

(xviii) chelating agents including disodium EDTA and tetrasodium EDTA. Chelators could enhance the diffusion and adsorption by binding to and removing metals present in hard water such as calcium and magnesium. Such hard water ions could conceivably complex with certain ionized "hooks" of the present invention electrostatically and inhibit their solubility.

(xix) hydrotropes such as ammonium xylene sulfate. For instance, if the "hooks" of the present invention are incorporated within a surfactant matrix, hydrotropes could improve performance by freeing up the "hook" compounds during dilution to facilitate improved binding to the substrate.

(xx) dispersing aids which may encompass, but are not limited to, non-ionic surfactants, amphoteric surfactants, and ionic surfactants. If the "hooks" of the present invention are incorporated within a non-aqueous matrix of as an insoluble dispersion, dispersing aids could be utilized to enhance solubilization and subsequent activation.

(xxi) Ion-pair ingredients. For certain ionic "hooks" of the present invention, compounds could be employed that ion-pair with the "hooks" including, but not limited to cations, anions, quaternized ammonium compounds, amphoteric compounds, and metals. Such charged species could be utilized to manipulate the diffusion, adsorption and the binding of the "hook" compounds of the present invention.

(xxii) Drying agents designed to minimize residual levels of water in non-aqueous solvent, including, but not limited to molecular sieves.

The pH of the compositions of the present invention is frequently important in achieving optimized chemisorption of the protected thiol compound. The most suitable pH for a given composition may depend principally on the type and structure of the protecting group as it pertains to activation. For instance, many of the protecting group can be activated for improved performance via pH catalyzed hydrolysis. In these cases, the pH of the composition would need to be such that the molecular 'hook' is not activated prior to usage. As described above, during usage the pH of the composition containing the molecular 'hook' can be manipulated, i.e., via inter-mixing with separate pH activating composition, such that the molecular 'hook' is activated during or immediately prior to usage.

The protecting groups of the present invention are to be used within a pH range from about 1 to about 12, preferably from about 3 to about 11, more preferably from about 4 to about 10. In the cases wherein the protecting group are activated at any of the above pH's, the composition would need to be non-aqueous and essentially free of water or moisture to such a degree that prohibits significant hydrolysis induced activation prior to usage. As such, the water imparted to the composition during usage from the shower, bath or from the wetted substrate could provide the activation required to optimize the resulting chemisorption.

As mentioned above, it has surprisingly been found that certain protecting groups are not activated hydrolytically at pH's within the above ascribed relevant range while still providing durable benefits on hair. For these compounds, the pH of the composition is irrelevant in as much as the composition pH suits the cosmetically active group, R.

Preferred embodiments of the present invention comprise a modified UV absorber which includes at least one UV absorbing moiety, at least one linker, and at least one molecular hook.

For example, said modified UV absorber typically imparts improved hair protection benefits when added to hair care compositions.

Modified UV absorbers include those of the formula

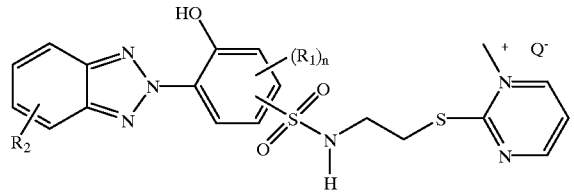

(XVI)

wherein $R_1$ is $C_1$–$C_{12}$alkyl, $C_5$–$C_7$cycloalkyl orphenyl-$C_1$–$C_3$alkyl, $R_2$ is hydrogen or halogen, n is 0, 1 or 2 and $Q^-$ is a counterion.

$C_1$–$C_{12}$Alkyl includes straight or branched alkyl radicals such as methyl, ethyl, n-propyl, isopropyl, n-butyl, sec-butyl, isobutyl, tert-butyl, amyl, isoamyl or tert-amyl, heptyl, octyl, isooctyl, nonyl, decyl, undecyl and dodecyl. $R_1$ is preferably a $C_1$–$C_6$alkyl group, for example methyl, ethyl, n-propyl, isopropyl, n-butyl, sec-butyl, isobutyl, t-butyl or isoamyl, especially a $C_3$–$C_5$alkyl group, for example isopropyl, isobutyl, sec-butyl, t-butyl or isoamyl.

$C_5$–$C_7$Cycloalkyl includes cyclopentyl, cycloheptyl and, preferably, cyclohexyl.

The subscript n is preferably 1 or 2, especially 1.

$R_2$ as halogen includes chlorine, fluorine and bromine and is preferably chlorine.

The counterion, $Q^-$, can include halides, borates, phosphates, tosylates, mesylates, triflates and other counterions known to those skilled in the art, with halides, for example bromide being preferred.

The compound of the formula

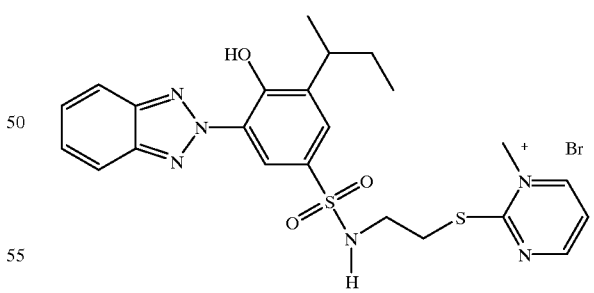

is especially preferred.

Other preferred embodiments of the present invention comprise a modified antioxidant which includes at least one antioxidant moiety, at least one linker, and at least one molecular hook. Modified anti oxidants include those of the formula

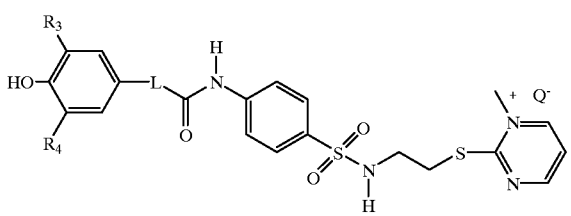
(XVII)

wherein
$R_3$ and $R_4$ are each independently of the other $C_1$–$C_{12}$alkyl, $C_5$–$C_7$cycloalkyl, phenyl, or $C_7$–$C_9$phenylalkyl,
L is a linking group and
$Q^-$ is a counterion.

$C_1$–$C_{12}$Alkyl includes straight or branched alkyl radicals such as methyl, ethyl, n-propyl, isopropyl, n-butyl, sec-butyl, isobutyl, tert-butyl, amyl, isoamyl or tert-amyl, heptyl, octyl, isooctyl, nonyl, decyl, undecyl and dodecyl. $R_3$ and $R_4$ are each independently of the other preferably a $C_1$–$C_6$alkyl group, for example methyl, ethyl, n-propyl, isopropyl, n-butyl, sec-butyl, isobutyl, t-butyl or isoamyl, especially a $C_3$–$C_5$alkyl group, for example isopropyl, isobutyl, sec-butyl, t-butyl or isoamyl.

$C_5$–$C_7$Cycloalkyl includes cyclopentyl, cycloheptyl and, preferably, cyclohexyl.

L as a linking group is preferably a direct bond, —$C_mH_{2m}$— or

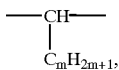

where m is an integer from 1 to 3.

The counter ion, $Q^-$, can include halides, borates, phosphates, tosylates, mesylates, triflates and other counterions known to those skilled in the art, with halides, for example bromide being preferred.

The compound of the formula

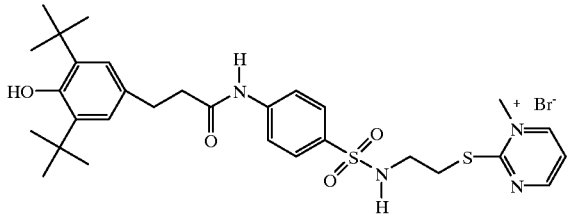

is especially preferred.

The modified UV absorbers of the formula (XVI) and modified antioxidants of the formula (XVII) can be incorporated into compositions for human and animal hair, such as wool and fur, to improve the color fastness of the hair and in general to stabilize the hair against degradation.

Compositions containing these modified UV absorbers and/or antioxidants typically impart cosmetic and other benefits in applications such as hair care (for example durable hair care benefit), textile care, cosmetics, oral care, and animal care.

CHARACTERISTICS

The protected thiol compounds of the present invention, when applied to a amino acid based substrate, have improved uptake levels and reduced levels of fade or removal. That is the thiol functional groups demonstrate improved attachment of the functional group, R, to the amino acid based substrate and longer lasting attachment than alternative reactive technologies. These benefits are demonstrated without requiring addition steps of reducing or oxidizing the substrate which typically are required in the art to achieve durable cosmetic benefits.

Reduction as defined herein comprises chemical compositions and treatments that induce the nucleophilic cleavage of disulfide bonds in keratin substrates resulting in the formation of free thiol groups in the form of cysteinyl amino acid residues. Reduction is employed in several commercial products and processes including the permanent-waving of human hair, human hair straightening, human hair depilation, and in the dyeing of wool with fiber reactive dyes. Several compounds and processes known to induce keratin reduction include (i) low molecular weight thiols such as thioglycolic acid, thiolactic acid, cysteine, thioglycerol, thioglycolic hydrazide, thioglycolamide, and glycerol monothioglycolate, (ii) sulfides such as salts of hydrogen sulfide, (iii) high temperature and alkali wherein the keratin is heated to around 100° C. or above by a heating source or steam and wherein the keratin can be contacted with an alkaline solution, (iv) cyanide such as the salts of hydrogen cyanide, (v) phosphines such as trihydroxymethyl phosphine or its precursor, tetrahydroxymethyl phosphonium chloride, (vi) other miscellaneous reducing agents such as borohydride, dithionite, hydrosulfite, and sulfoxylate and (vii) combinations thereof. Reduction as defined herein generally refers to the above processes and compositions which reduce greater than 10% of the disulfide bonds in the keratinaceous substrate. The relative quantities of reduced versus unreduced keratin fiber depend on the type of reducing agent, its concentration (or degree of application in the case of heat), the solution-to-hair ratio, pH of the reaction medium, time of reaction, fiber diameter, and the condition of the hair. A more detailed discussion on disulfide reduction can be found in the article by Gershon et al. (Gershon, S. D.; Goldberg, M. A.; Rieger, M. In Cosmetics Science and Technology, Sagarin. E. , eds., pp. 583–627. Interscience, New York (1963)).

Oxidation as defined herein comprises chemical compositions and treatments that induce the oxidative cleavage of disulfide bonds in keratin substrates resulting in the formation of sulfonic acid groups in the form of cysteic acid amino acid residues. Oxidation is employed in several commercial products and processes including the bleaching of human hair, permanent dyeing of human hair with oxidation dyes, and in the dyeing of wool with fiber reactive dyes. Hydrogen peroxide is the principle oxidizing agent used in most oxidizing compositions and is delivered liberally to the substrate as a 3 to 12% solution which may be alkaline. Persulfates, in the form of their sodium potassium and ammonium salts, may also be used to be mixed with the hydrogen peroxide just before use. Other ingredients that may be additionally included in the composition include sodium percarbonate, sodium perborate, magnesium perborate, magnesium dioxide and barium binoxide. Oxidation as defined herein generally refers to the above processes and compositions which degrade greater than 10% of the disulfide bonds in the keratinaceous substrate. A more detailed discussion on disulfide oxidation can be found in the articles by Zahn and Robbins (Zahn, H. J. Soc. Cosmet. Chem. 17:687 (1966); Robbins, C.; Kelly, C. J. Soc. Cosmet. Chem. 20:555 (1969)).

Both reduction and oxidation of amino acid based substrates lead to irreparable damage to the substrate by virtue of their destructive chemical reactions. For instance, both reduction and oxidation result in disulfide bond cleavage which has been shown to significantly reduce the wet tensile properties of human hair through 30% extension (Clarence Robbins book: Chemical and Physical Behaviour of Human Hair). Also, reduced hair has been shown to be less rigid in the wet state than unreduced hair (Bogaty, H. J. Soc. Cosmet. Chem. 18:575 (1967)) and the wet bending stiffness and wet stretching stiffness were demonstrated to decrease on oxidized hair (Robbins Book). Furthermore, reduced hair has been shown to exhibit increased frictional resistance (Schwartz, A.; Knowles, D. J. Soc. Cosmet. Chem. 14:455 (1963)) which is evidence of imparted damage to the hair. These demonstrated destructive chemical interactions with keratin have been shown to translate into keratin that is drier, more brittle to the touch, more porous, weaker and which tangles more easily (The Science of Hair Care, by Charles Zviak).

PROCESSES FOR PREPARING THE PROTECTED THIOL COMPOUNDS

The compounds of the invention can be prepared by any of a number of procedures known to those skilled in the art. Several nonlimiting examples are described herein below.

HETEROCYCLIC PROTECTING GROUPS

Alkylthio substituted pyridines can be prepared by reaction of halopyridines with a variety of thiols in the form of metal salts [Takahashi, Saikachi, Akai, *J. Pharm. Soc. Japan,* 1943, 63, 153; Adams, Ferreti, *J. Am. Chem. Soc.,* 1959, 81, 4927]. Another method of preparation involves alkylation of pyridinethiols [Marckwald, Klemm, Trabert, Ber., 1900, B33, 1156; Forrest, Walker, *J. Chem. Soc.,* 1948, 1939].

Alkylthio substituted pyrimidines can be prepared by alkylation of mercaptopyrimidines [Southon, Pfeiderer, *Chem. Ber.,* 1978, 111, 982; A. G. Geigy, *Chem. Abstr.,* 1969, 70, 68418] or directly from halogenopyrimidines [Semga, Ichiba, Kanazawa, Nishigaki, *J. Heterocyclic. Chem.,* 1982, 30, 610].

Alkylthio substituted pyrazines can be prepared from halogenopyrazines and appropriate sodium (or potassium) alkyl thiolate at elevated temperatures [Konakahara, Y. Takagi, *Bull. Chem. Soc. Japan,* 1960, 80, 349]. The alternative method is alkylation of mercaptopyrazines [A. Albert, G. B. Barlin, *J. Chem. Soc.,* 1962, 3129].

Alkylthio substituted pyridazines can be prepared by treatment of halopyridazines with a thiol in the form of its alkali salt or with a thiol in the presence of base [Druey, K. Meier, K. Eichenberger, *Helv. Chim. Acta,* 1954, 37, 121; M. Fujisaka, Y. Neno, H. Shinobara, E. Imoto, *Bull. Chem. Soc. Japan,* 1964, 37, 1107; T. Horie, K. Kinjo, T. Ueda, *Chem. Pharm. Bull.,* 1962, 10, 580]. Alkylation of pyridazinethiones and pyridazinethiols as well as some other methodologies are also published. [M. Tisler and B. Stanovnik *"Pyridazines and their Benzo Derivatives"*, in *"Comprehensive Heterocyclic Chemistry",* 1984, Pergamon Press, Ltd.; M. Tisler and B. Stanovnik *"Sulfur Compounds of Pyridazines"*, in *"The Chemistry of Heterocyclic Compounds",* 1973, John Wiley&Sons, Inc.]

For the alkylthiol substituted triazines and tetrazines, a comprehensive review on the synthesis of these compounds is found in the literature. [M. Tisler and B. Stanovnik, *J.Het. Chem.,* 1971, 785; Reissert and Grube, *Chem. Ber.,* 42, 1909, 3720; Gompper and Schoenafinger, *Chem. Ber.,* 112, 1979, 1529; Arndt, Eistert, *Chem. Ber.,* 60, 2602, 1927; Grundmann et al, *J. Org. Chem.,* 23, 1958, 1522; Cristescu, Panaitescu, Pharmazie, 17, 1962, 209; H. Neunhoeffer, H. Hammann, *Tet. Lett.,* 24, 1983, 1767; J. L. Johnson, B. Whitney, L. M. Leslie, *J. Het. Chem.,* 17, 1980, 501; S. C. Fields, M. H. Parker, W. R. Erickson, *J. Org. Chem.,* 1994, 8284.]

The six membered O, N, and/or S containing heterocyclics with C=O, C=S or C=C exocyclic groups can be prepared from halogen derivatives of corresponding heterocycles and thiols. [Tominaga, A. Ushirogochi, Y. Matsuda, *J. Het. Chem.,* 24, 1987, 1557; Y. Tominaga, et al, *Chem Pharm, Bull.,* 32, 3384, 1981; L. Adelfang, *J. Org. Chem.,* 31, 2389, 1966; L. W. Singh, H. Junjappa, Synthesis, 5, 531, 1985; W. D. Rudorf, R. Schawrz, *Tet. Lett.,* 28 4267, 1987; B. Deb, H. Ila, et al, *Synthesis,* 10, 893, 1987.]

Alkylthio substituted pyridinium derivatives can be prepared by quaternization of the corresponding pyridine alkyl thioethers and other methods. [Yamada, et al, *J. Org. Chem.,* 42, 2180, 1977; M. Yamada, et al, *J. Chem. Soc., Chem. Comm.,* 179, 1979; T. Sakakibara, Y. Watabe, M. Yamada, R. Sudoh, *Bull. Chem. Soc. Jpn,* 61, 247, 1988.]

Alkylthio substituted xanthenes can be prepared from thiols and xanthene with a suitable leaving group [K. J. Divakar, C. B. Reese, et. al., *J. Chem. Soc., Perkin Trans.* 1, 1990 (6), 1753]

Alkylthio substituted pyrimidinium derivatives can be prepared by quaternization of the corresponding pyrimidine alkylthioethers and other methods. [Deichmeister, Platoshkiin, *Khim. Geterosicl. Soedin.,* 1, 1961, 333; Brown, England, *J. Chem. Soc. C,* 1971, 2507; Ueda, Ohtsuka, *Chem. Pharm. Bull.,* 21, 1973, 1451.]

Alkylthio substituted pyrazinium derivatives can be prepared by quaternization of the corresponding pyrimidine alkyl thioethers and other methods. [Barlin, Benbow, *J Chem. Soc., Perkin Trans.* 2, 1975, 1385; Honz, et al, Tetrahedron, 26, 1970, 2305; B. Geutsen et al, *Tetrahedron,* 1989, 6519; S. Batori, A. Messmer, *J. Het. Chem.,* 1990, 1673.]

Alkylthio substituted furans can be prepared from the corresponding furan thiols and alkyl halides. [Gorzynski, D. Rewicki, *Liebigs Ann. Chem.,* 1986, 625; P.G. McDougal, Y-I Oh, *Tet. Lett.,* 27, 139, 1986; R. Tanikaga, et al, *J. Chem. Soc., Chem. Com.,* 1106, 1981; H. Gotthatdt, C. M. Weisshuhn, K. Dorhofer, *Chem. Ber.,* 111, 3336, 1978; R. Adams, A. Ferretti, *J. Am. Chem. Soc.,* 81, 4927, 1959; A. Ferretti, G. Tesi, Chem Ind., p. 1987, 1964; L. M. Yagupolskii, N. V. Kondratenko, V. P. Sambur, *Synthesis,* 721, 1975; B. L. Feringa, et al, *Synthesis,* 316, 1988; S. P. Tanis, D. B. Head, *Tet. Lett.,* 25, 4451, 1984.]

Alkylthio substituted pyrroles can be prepared by S-alkylation of 2- and 3-pyrrolethiols under standard base-catalyzed conditions. [K. Olsen, H. R. Snyder, *J. Org. Chem.,* 30, 184, 1965; S. Apparao; H. Ila, H. Junjappa, *Synthesis,* 65, 1981; M. Cardellini et al, *Synthesis,* 1980, 886; A. K. Gupta, H. Ila, et al, *Synthesis,* 141, 1989; S. Gronowitz, R. Kada, J. Het. Chem., 1041, 1984; M. Colonna, M. Polni, *Gazz. Chim. Ital.,* 116, 449, 1986; H. Kojima, H. Inoue, et al, *Chem. Lett.,* 1499, 1989; Y. Tominaga, et al, *J. Het. Chem.,* 26, 477, 1989.]

Alkylthio substituted thiophenes can be prepared by reacting the alkali salts of thiophene thiols with aliphatic halogen compounds. [Thomas, G. Singh, H. Ila, H. Junjappa, *Tet. Lett.,* 30, 3093, 1989; W.-D. Rudorf, A. Schierhorn, M. Augustin, *J. Prakt. Chem.,* 321, 1021, 1979; J. Cymerman-Craig, J. W. Loder, *Org. Synth.* 667, 1963; J. Cymennan-Craig, J. W. Loder, *J. Chem. Soc.,* 237, 1954; E. J. Smutny, *J. Am. Chem. Soc.,* 91, 208, 1969.]

Alkylthio substituted pyrazoles, the 3- and 5- derivatives, can be prepared by the akylation of the corresponding pyrazolethiones [Michaelis, Lachwitz, *Chem. Ber.,* 1910, 43, 2106; Michaelis, *Ann.,* 1908, 283].

Alkylthio substituted isoxazoles can be prepared by alkylating the thio group at the 3 position of isoxazoles [A. Thuiller and J. Vialle, *Bull. Soc. Chim. Fr.,* 1959, 1398; W. D. Rudrorf and M. Augustin, *J Prakt. Chem.,* 1978, 320, 585;: K. Tomita, S. Sugai and M. Saito, *Chem. Pharm. Bull.,* 1979, 27, 2415; S. Sugai and K. Tomita, *Chem. Pharm. Bull.,* 1980, 28, 552].

Alkylthio substituted isothiazoles can be prepared by alkylating both 3- and 5-mercaptoisothiazoles [K. R. H. Wooldridge, *Adv. Heterocycl. Chem.,* 1972, 14, 1; B. Torretta, G. Ronsisvalle, E. Bousquet, F. Guerrera and M. A. Siracusa, *Gazz. Chim. Ital.,* 1980, 133;: K. Gewald, W. Radke and U. Hain, *J. Prakt. Chem.,* 1980, 322, 1021].

Alkylthio substituted triazoles can be prepared from the corresponding thiotriazoles by S-alkylation with various alkyl bromides [M. A. Weaver, R. R. Giles, Ger. Pat., 1970, 1,919,045; J. Heindl, E. Schroeder, H. W. Kelm, *Eur. J. Med. Chem.-Chim. Ther.,* 1975,10, 121.].

Alkylthio substituted 1,2,4-oxadiazoles can be prepared from the corresponding halogen oxadiazoles and thiols. [M. Paton, D. G. Hamilton, *Tet. Lett.,* 24, 5141, 1983; D. J. Greig, et al, *J. Chem. Soc., Perkin Trans.,* 607, 1987; Sumitomo Chem Ind KK, Japan Patent, 1005072 (J6-1005072), 86-05143, 1986.]

Alkylthio substituted 1,2,4-thiadiazoles can be prepared via dipotassium cyanodithioiminocabonate followed by alkylation [W. A. Thaler and J. R. McDivitt, *J. Org. Chem.,* 1971, 36, 10;: Badische Anilin und Soda-Fabrik A.-G., Br. Pat. 1 116198 (1968), (*Chem. Abstr.,* 1968, 69, 86995)].

Alkylthio substituted pyrazolium derivatives can be prepared by reaction of the corresponding alkylthiopyrazoles with alkyl halides. [Michaelis, *Justus Lieb. Ann. Chem.,* 331, 1904, 230; v. Auwers, Bergmann, *Justus Lieb. Ann. Chem.,* 472, 1929, 310; Michaelis, *Justus Lieb. Ann. Chem.,* 361, 1908, 270; K. Hartke, X.-P. Popp, *Arch. Pharm,* 1994, 385.]

Alkylthio substituted triazolium derivatives can be prepared from halogen derivatives of the corresponding triazoles and lithium thiolates [M. Begtnup, *Bull. Soc. Chim. Belg.,* 1988, 573].

Alkylthio substituted azepines can be obtained from the corresponding halogen derivatives [W. Steglich, H. Bauek, B. M. Grosse, R. Leschke, T. Josten, J. Klein, *J. Heterocycl. Chem.,* 1990, 107].

Alkylthio substituted thiepinium derivatives can be prepared from the corresponding thiepins and an alkylation agent [H. Hofmann, A. Molnar, *Tetrahedron Lett.,* 1977, 1985; H. Hofmann, A. Molnar, C. Gottfent, *Liebigs Ann. Chem.,* 1983, 425; H. Hofmann, H. Fisher, M. De Vries, *Z. Naturforsch, Teil B,* 1990, 1573].

Synthesis routes for heterocyclic protected thiol compounds are exemplified by the following non-limiting examples:

EXAMPLE 1

Pyrimidinium, 2-[[3-[[[4-[(2-hydroxy-1-naphthalenyl)-azo]phenyl]sulfonyl]amino]propyl]thio]-1-methyl-, bromide

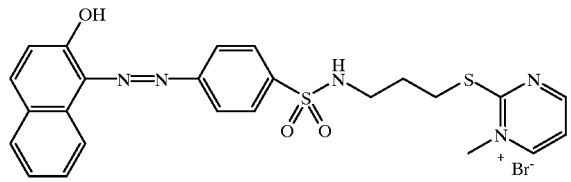

3-(4-Acetamidophenylsulfonamido)propyl bromide

To a stirred solution of N-acetylsulfanilyl chloride (57.15 g, 0.244 mol) in acetone (500 mL) and H$_2$O (187.5 mL) at 0° C. was added 3-bromopropylamine hydrobromide (25.0 g, 0.114 mol). When a clear solution was obtained, a solution of sodium hydrogencarbonate (44.15 g, 0.526 mol) in H$_2$O (550 mL) was added dropwise, maintaining the internal temperature at 0–5° C. When the addition was completed, the reaction mixture was heated at 50° C. for 5 h, then cooled to room temperature and poured into ice H$_2$O with stirring. After stirring at 5° C. for 4 h, the suspension was filtered and the filter cake was washed with H$_2$O and dried in vacuo to give 34.6 g (90%). An additional reaction was performed to give an additional 63.7 g of similar material.

3-(4-Aminophenylsulfonamido)propyl bromide

A mixture of 3-(4-acetamidophenylsulfonamido)propyl bromide (34.5 g, 0.103 mol), conc. HCl (43 mL) and EtOH (86 mL) was heated at reflux for 0.5 h, and the suspension was poured into a solution of H$_2$O (200 mL) and EtOH (150 mL). The suspension was neutralized with 30% NaHCO$_3$ (aq) to pH 7–8, then filtered. The filter cake was washed with H$_2$O and dried in vacuo to give 27.2 g (90%). An additional reaction was performed to give an additional 48.8 g of similar material.

2-Hydroxynaphthalene, 1-[4-[[[3-(bromopropyl)]amino]-sulfonyl]phenyl]azo]-

A solution of 3-(4-aminophenylsulfonamido)propyl bromide (25.0 g, 0.085 mol) in H$_2$O (300 mL) and conc. HCl (35.5 mL, 0.426 mol) was cooled to 5–10° C. then a solution of sodium nitrite (6.70 g, 0.094 mol) in H$_2$O (50 mL) was added portionwise, maintaining the internal temperature below 10° C. When the addition was completed, the solution was stirred for 5 min at 5–10° C., and then the solution was added in three portions (maintaining the internal temperature below 10° C.) to a solution of 2-naphthol (12.3 g, 0.085 mol) and sodium hydroxide (22.2 g, 0.554 mol) in H$_2$O (150 mL). Additional sodium hydroxide was added during the addition of the diazonium salt to maintain the pH above pH 7. When the addition was completed, the red-orange suspension was stirred at 5–10° C. for 10 min then allowed to stand at room temperature for 20 h. The suspension was acidified with conc. HCl (45 mL) (pH <5), stirred for 2 h and filtered. The filter cake was triturated with H$_2$O (4×500 mL), then filtered and dried in vacuo at 60° C. to give 37.1 g (97%).

2(1H)-Pyrimidinethione, 1-methyl-

To a stirred mixture of 1-methyl-2-thiourea (76.6 g, 0.85 mol) and malonaldehyde bis(dimethyl acetal) (126.8 g, 0.77 mol) in EtOH (1.5 L) was added 10 M HCl (76.6 mL, 0.77 mol) in one portion. The resulting mixture was stirred at 25° C. for 18 h, then spin-evaporated in vacuo. The residue was dissolved in H$_2$O (1.25 L). The solution was made alkaline by the portionwise addition of K$_2$CO$_3$ and extracted with CH$_2$Cl$_2$ (4×500 mL). The combined extracts were dried over MgSO$_4$ and spin-evaporated in vacuo to a solid. The crude product was recrystallized from EtOH (600 mL) then dried to constant weight in vacuo at room temperature to give 22.9 g (23%) of product; mp 186–188° C. (uncorrected). An additional reaction was performed to give a total of 40.7 g.

Pyrimidinium, 2-[[3-[[[4-[(2-hydroxy-1-naphthalenyl)azo]-phenyl]sulfonyl]amino]propyl]thio]-1-methyl-, bromide A solution of 2-hydroxynaphthalene, 1-[4-[[[3-(bromopropyl)]amino]sulfonyl)phenyl]azo]- (22.4 g, 0.05 mol) and 2(1H)-pyrimidinethione, 1-methyl-(6.30 g, 0.05 mol) in N,N-dimethylformamide (100 mL) was heated at 80° C. for 4 h. The reaction mixture was cooled to room temperature and diluted with Et$_2$O (400 mL) to give a gummy red suspension. The solvent was decanted, and the residue was dissolved in MeOH:acetone (1:1, 300 mL). The solution was concentrated to dryness to a foam. The foam was triturated with acetone (2.5 L) for 5 h at room temperature. The resulting suspension was filtered and the filter cake was washed with acetone and dried in vacuo at 45° C. to constant weight to give 16.1 g (56%) of solid; mp (uncorrected) 169–172° C. The proton NMR spectrum was consistent with the proposed structure.

| Elemental analysis: | C | H | N | S | Br |
|---|---|---|---|---|---|
| Calc. | 50.44 | 4.21 | 12.19 | 11.16 | 13.91 |
| Obs. | 50.27 | 4.47 | 12.02 | 11.13 | 13.97 |

EXAMPLE 2

Pyrimidinium,1-methyl-2-[2-[[[[5-(dimethylamino)-1 naphthalenyl]sulfonyl]amino]ethyl]thio]-, bromide

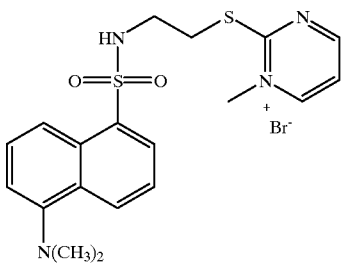

Pyrimidine, 1,2-dihydro-1-methyl-2-thio-

To a stirred mixture of 1-methyl-2-thiourea (76.6 g, 0.850 mol) and malonaldehyde bis(dimethyl acetal) (126.8 g, 0.7722 mol) in EtOH (1.5 L) was added 10 M HCl (76.6 mL, 0.766 mol) in one portion. The resulting mixture was stirred at 25° C. for 18 h, then spin-evaporated in vacuo. The residue was dissolved in H₂O (1.5 L). The solution was made alkaline by the portionwise addition of K₂CO₃ (60 g), then extracted with CH₂Cl₂ (3×1.0 L). The combined extracts were dried over MgSO₄ (20 g) and spin-evaporated in vacuo to give 100.6 g (103.3%) of crude product as a solid. This was combined with 24.5 g of previously obtained material and dissolved in refluxing EtOH (900 mL). The solution was stored at 3° C. for 18 h. The resulting precipitate was collected by filtration and dried to constant weight in vacuo to give 30.0 g (24.0% recovery) of purified product.
Pyrimidinium, 1-methyl-2-[2-[[[[-5-(dimethylamino)-1-naphthalenyl]sulfonyl]amino]ethyl]thio]-, bromide A stirred mixture of the preceding intermediate (10.0 g, 79.3 mmol) and naphthalenesulfonamide, 5-(dimethylamino)-N-(2-bromoethyl)- (28.3 g, 79.3 mmol) in 1-propanol (150 mL) was heated at reflux for 2 h. The mixture was spin-evaporated in vacuo to a solid residue. The residue was triturated with acetone (200 mL), then collected by filtration and dried to constant weight in vacuo at 25° C. to give 32.0 g (83.6%) of the target compound, mp 196–198° C. (d) (uncorrected). Proton NMR and IR spectra were consistent with the proposed structure.

| Elemental analysis: | C | H | N | S | Br |
|---|---|---|---|---|---|
| Calc. | 47.20 | 4.79 | 11.59 | 13.27 | 16.53 |
| Obs. | 47.25 | 4.73 | 11.60 | 13.19 | 16.68 |

EXAMPLE 3

Pyridinium, 1-methyl-5-(trifluoromethyl)-2-[2-[[[[5-(dimethylamino)-1 naphthalenyl]sulfonyl]amino]ethyl]-thio], bromide

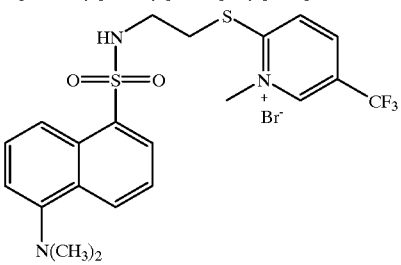

Pyridinium, 1-methyl-5-(trifluoromethyl)-2-[2-[[[[5-(dimethylamino)-1-naphthalenyl]sulfonyl]amino]ethyl]-thio], bromide

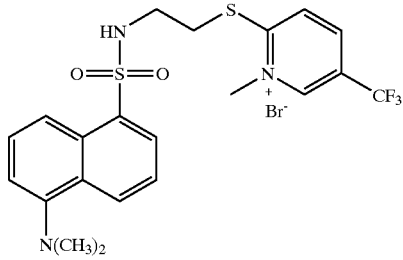

N-Methyl-5-trifluoromethylpyridone

A stirred mixture of 5-(trifluoromethyl)-2-pyridinol (34.8 g, 0.213 mmol), potassium carbonate (101 g, 0.730 mol) and iodomethane (48.7 mL, 0.783 mol) in dry acetone (750 mL) in a sealed bottle was heated at 59° C. for 7 h then cooled to ambient temperature. The reaction mixture was filtered and concentrated to dryness to give a yellow solid. The crude product was purified by column chromatography (1 kg silica gel) eluted with hexanes:EtOAc (1:1) to give a white solid. The solid was dried in vacuo at room temperature for 2 h to give 34.3 g (90% yield). Additional reactions were performed to give a total of 86.9 g of similar product.
2(1H)-Pyridinethione, 1-methyl-5-(trifluoromethyl)-

A stirred mixture of the preceding intermediate (34.3 g, 0.194 mol) and Lawesson's Reagent (39.2 g, 0.097 mol) in dry toluene (195 mL) was heated at reflux for 10 min, then the toluene was removed by evaporation. The residue was distilled in vacuo (Kugelrohr apparatus) at 120-140° C./3 mm Hg to give pure product as a yellow solid (36.2 g, 96%). Additional reactions were performed to give a total of 89.9 g of similar material.
Pyridinium, 1-methyl-5-(trifluoromethyl)-2-[2- [[[[5-(dimethylamino)-1-naphthalenyl]sulfonyl]amino]ethyl]-thio]-, bromide.

A stirred mixture of the preceding intermediate (46.7 g, 0.242 mol) and naphthalenylsulfonamide, 5-(dimethylamino)-N-(2-bromoethyl)- (86.3 g, 0.242 mol) in dry 1-propanol (270 mL) was refluxed for 4.5 h. The reaction mixture was concentrated to give the crude product as a yellow foam. This foam was dissolved in acetone (450 mL) and slowly added to a stirring solution of hexanes:isopropyl ether (2:1, 12 L) to give a yellow precipitate. The precipitate was collected by filtration, washed with hexanes (500 mL) and dried in vacuo at 40° C. This solid was reprecipitated twice more in a similar fashion to give 92.4 g (69%) of pure target. An additional reaction was performed to give a total of 119.9 g of the target compound; m.p. 125–129 degrees C (uncorrected). Proton NMR and IR spectra were consistent with the proposed structure.

| Elemental analysis: | C | H | N | S | Br |
|---|---|---|---|---|---|
| Calc. | 45.82 | 4.21 | 7.63 | 11.65 | 14.52 |
| Calc.* | 45.87 | 4.61 | 7.23 | 11.03 | 13.75 |
| Obs. | 45.91 | 4.62 | 7.01 | 10.78 | 14.15 |

*Calc. for $C_{21}H_{23}BrF_3N_3O_2S_2 \cdot 0.1$ i-$Pr_2O \cdot 0.2$ acetone$\cdot 0.5$ $H_2O$

EXAMPLE 4

Pyrimidinium, 2-[(3,3,4,4,5,5,6,6,7,7,8,8,9,9,10,10,10-heptadecafluorodecyl)thio]-1-methyl-, iodide

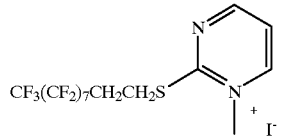

2(1H)-Pyrimidinethione, 1-methyl

To a stirred mixture of 1-methyl-2-thiourea (76.6 g, 0.85 mol) and malonaldehyde bis(dimethyl acetal) (126.8 g, 0.77 mol) in EtOH (1.5 L) was added 10 M HCl (76.6 mL, 0.77 mol) in one portion. The resulting mixture was stirred at 25° C. for 18 h, then spin-evaporated in vacuo. The residue was dissolved in $H_2O$ (1.25 L). The solution was made alkaline by the portionwise addition of $K_2CO_3$ and extracted with $CH_2Cl_2$ (4×500 mL). The combined extracts were dried over $MgSO_4$ and spin-evaporated in vacuo to a solid. The crude product was recrystallized from EtOH (600 mL) then dried to constant weight in vacuo at room temperature to give 22.9 g (23%) of product; mp 186–188° C. (uncorrected). An additional reaction was performed to give a total of 40.7 g.

Pyrimidinium, 2-[(3,3,4,4,5,5,6,6,7,7,8,8,9,9,10,10,10-heptadecafluorodecyl)thio]-1-methyl-, iodide A solution of the preceding intermediate (22.9 g, 0.181 mol) and 1-iodo-1H,1H,2H,2H-perfluorodecane (100.5 g, 0.175 mol) in acetone (1.2 L) was heated at reflux for 20 h, cooled to 15° C. and filtered. The filter cake was washed with hexanes (500 mL) and dried in vacuo at room temperature to give 48.6 g (40% yield); mp 196–196.5° C. (uncorrected). A second reaction was performed to give 11.1 g (38% yield); mp 206–206.5° C. (uncorrected). The proton NMR spectrum was consistent with the proposed structure.

| Elemental analysis: | C | H | N | S |
|---|---|---|---|---|
| Calc. | 25.73 | 1.44 | 4.00 | 4.58 |
| Obs. | 25.68 | 1.47 | 4.05 | 4.56 |

EXAMPLE 5

Benzothiazolium, 2-[[2-[[[5-(dimethylamino)-1-naphthalenyl]-sulfonyl]amino ethyl]thio]-3-methyl-, bromide

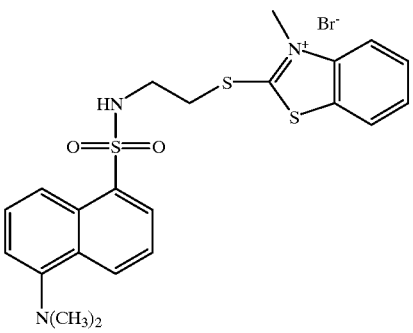

Naphthalenesulfonamide, 5-(dimethylamino)-N-(2-bromoethyl)-

A suspension of 5-dimethylaminonaphthalene-1-sulfonyl chloride (52.5 g, 0.194 mol) and 2-bromoethylamine hydrobromide (42.3 g, 0.206 mol) in THF (550 mL) was cooled to 2° C. A solution of triethylamine (40.3 g, 0.398 mol) in THF (230 mL) was added dropwise over a 2 h period while maintaining the internal temperature below 6° C. After complete addition the mixture was stirred at ambient temperature for 72 h. The mixture was clarified then concentrated to an orange oil which was chromatographed over silica (2.2 kg) packed and eluted with hexanes-EtOAc (3:1). Fractions (500 mL) containing the purified product were combined, clarified then concentrated to a damp solid. This material was triturated in hexanes (250 mL), collected on a filter, washed with hexanes (50 mL) then dried to constant weight in vacuo at room temperature to give 61.7 g (89% yield) of product as off-white crystalline solid.

Benzothiazolium, 2-[[2-[[[5-(dimethylamino)-1-naphthalenyl]sulfonyl]amino]ethyl]thio]-3-methyl-, bromide A solution of naphthalenylsulfonamide, 5-(dimethylamino)-N-(2-bromoethyl)- (15.0 g, 42.0 mmol) and 3-methyl-benzothiazole-2-thione (11.0 g, 60.7 mmol) in acetone (25 mL) was heated at reflux for 4 days (Note 1). After cooling to 5° C., the mixture was diluted with $Et_2O$ (150 mL) and suction filtered. The filter cake was washed with $Et_2O$ (200 mL) and sucked dry to give the crude product. The crude product was dissolved in a mixture of $CH_2Cl_2$ (140 mL) and MeOH (30 mL) then diluted with EtOAc:hexanes (1:2, 750 mL). The suspension was suction filtered and the filter cake was washed with $Et_2O$ (200 mL), then dried in vacuo at room temperature for 4 h to give the target compound (9.0 g, 40%) as a yellow solid. An additional reaction was performed to give a total of 22.9 g of target compound, mp(uncorrected) 156 –159° C. Proton NMR and IR spectra were consistent with the proposed structure.

| Elemental analysis: | C | H | N | S | Br |
|---|---|---|---|---|---|
| Calc. | 49.06 | 4.49 | 7.80 | 17.86 | 14.84 |
| Obs. | 49.01 | 4.33 | 7.69 | 17.68 | 15.02 |

EXAMPLE 6

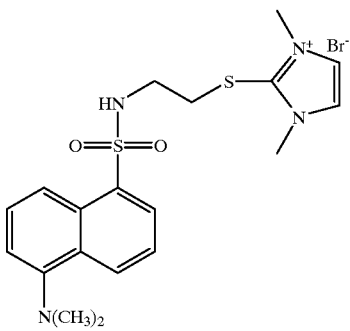

1H-Imidazolium,1,3-dimethyl-2-[2-[[[[5-(dimethylamino)-1-naphthalenyl]sulfonyl]amino]ethyl]thio]-, iodide Naphthalenesulfonamide, 5-(dimethylamino)-N-(2-bromoethyl)-

A suspension of 5-dimethylaminonaphthalene-1-sulfonyl chloride (50.0 g, 0.185 mol) and 2-bromoethylamine hydrobromide (40.4 g, 0.197 mol) in THF (500 mL) was cooled to 2° C. A solution of triethylamine (38.5 g, 0.380 mol) in THF (250 mL) was added dropwise over a 2 h period while maintaining the internal temperature below 6° C. After complete addition the mixture was stirred at ambient temperature for 17 h. The mixture was clarified, and the filter cake rinsed with THF to remove all of the product. The combined filtrates were concentrated to an orange oil which was chromatographed over silica (2.2 kg) packed and eluted with hexanes-EtOAc (3:1). Fractions (500 mL) containing the purified product were combined, clarified, then concentrated to a damp solid. This material was triturated in hexanes (250 mL), collected on a filter, washed with hexanes (50 mL) then dried to constant weight in vacuo at 40° C. to give 56.9 g (86.1% yield) of product as an off-white crystalline solid.

1H-Imidazole, 1-methyl-2-[2-[[[[5-(dimethylamino)-1-naphthalenyl]sulfonyl]amino]ethyl]thio]-

A suspension of sodium hydride (2.1 g of 60%, 52 mmol) in DMF (25 mL) was cooled to 10° C. A solution of 2-mercapto-1-methylimidazole (6.0 g, 52 mmol) in DMF (50 mL) was added dropwise over a 30 min period while maintaining the internal temperature below 15° C. After complete addition, the reaction mixture was stirred at ambient temperature for 1.5 h. A solution of the preceding intermediate (18.7 g, 52.3 mmol) in DMF (75 mL) was added in one portion and the resulting solution was stirred at 50° C. for 1.5 h then cooled to ambient temperature. The reaction solution was poured over cold $H_2O$ (3 L) then extracted with $CH_2Cl_2$ (1×1 L and 1×500 mL). The combined extracts were washed with $H_2O$ (750 mL) and saturated brine (750 mL), dried over $Na_2SO_4$, clarified, then concentrated in vacuo to a green oil. This material was combined with similar material from a smaller reaction and passed through a pad of silica (750 g) packed with EtOAc-hexanes (1:1) then eluted with 1:1, 6 L; 2:1, 3 L; 3:1, 4 L and finally EtOAc, 3 L. Fractions containing the purified product were combined, clarified then concentrated to a green glass which was triturated in THF (50 mL). The resulting solid was dried to constant weight in vacuo to give 23.6 g (93% yield) of material as a light green solid.

1H-Imidazolium, 1,3-dimethyl-2-[2-[[[[5-(dimethylamino)-1-naphthalenyl]sulfonyl]amino]ethyl]thio]-, iodide A solution of the preceding intermediate (23.6 g, 60.4 mmol), DMF (51 mL) and iodomethane (3.76 mL, 60.4 mmol) was stirred in a flask sealed with a rubber septum for 18 h at ambient temperature. The reaction solution was diluted with $Et_2O$ (1.5 L) and vigorously stirred for 30 min. The resulting solid was collected on a filter, washed with $Et_2O$ (2×50 mL) then dried in situ. This material was dissolved in $CH_2Cl_2$ (300 mL) and MeOH (15 mL), clarified, diluted with EtOAc (300 mL), then concentrated to a thick slurry. The resulting solid was collected on a filter, washed with EtOAc (2×75 mL), then dried to constant weight in vacuo to give 27.0 g (71% yield) of product, mp(uncorrected) 184–186 degrees C. Proton NMR and IR spectra were consistent with the proposed structure.

| Elemental analysis: | C | H | N | S |
|---|---|---|---|---|
| Calc. | 42.86 | 4.73 | 10.52 | 12.04 |
| Obs. | 42.89 | 4.73 | 10.54 | 12.20 |

EXAMPLE 7

Pyrimidinium, 1-methyl-2-[[8-[3,4,5-trihydroxybenzoyl)-oxy]octyl]thio]-, bromide

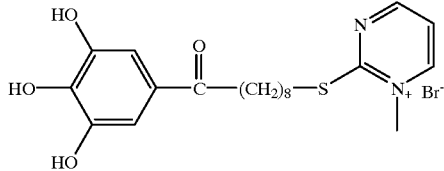

Pyrimidinium, 1-methyl-2-[[8-[3,4,5-trihydroxybenzoyl)-oxy]octyl]thio]-, bromide

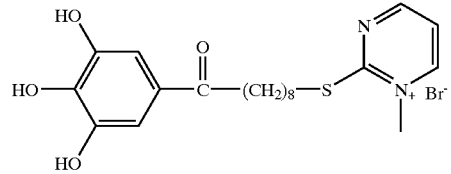

8-Bromooctyl gallate

A suspension of gallic acid (23.5 g, 0.138 mol), 8-bromo-1-octanol (90.0 g, 0.430 mol), and conc. sulfuric acid (3.0 mL) was stirred and heated at 120–130° C. for 0.5 h, then cooled to 100° C. and stirred at 100° C. for 1 h. Cooled to room temperature, diluted with EtOAc (300 mL), and washed with $H_2O$ (2×200 mL) and brine (200 mL). The organic layer was dried ($MgSO_4$), filtered, and concentrated to give the crude product (111 g). The crude material was purified by column chromatography (2.2 kg silica gel eluted with EtOAc:hexanes (2:3)) to give 33.3 g (67%) as a white pasty solid.

2(1H)-Pyrimidinethione, 1-methyl-

To a stirred mixture of 1-methyl-2-thiourea (76.6 g, 0.85 mol) and malonaldehyde bis(dimethyl acetal) (126.8 g, 0.77 mol) in EtOH (1.5 L) was added 10 M HCl (76.6 mL, 0.77 mol) in one portion. The resulting mixture was stirred at 25° C. for 18 h, then spin-evaporated in vacuo. The residue was dissolved in $H_2O$ (1.25 L). The solution was made alkaline by the portionwise addition of $K_2CO_3$ and extracted with $CH_2Cl_2$ (4×500 mL). The combined extracts were dried over $MgSO_4$ and spin-evaporated in vacuo to a solid. The crude product was recrystallized from EtOH (600 mL) then dried to constant weight in vacuo at room temperature to give 22.9 g (23%) of product; mp 186–188° C. (uncorrected). An additional reaction was performed to give a total of 40.7 g.

Pyrimidinium, 1-methyl-2-[[8-[(3,4,5-trihydroxybenzoyl)-oxy]octyl]thio]-, bromide To a solution of 8-bromooctyl gallate (33.3 g, 0.092 mol) in 1-propanol (170 mL) was added the above intermediate (11.7 g, 0.093 mol), and the resulting suspension was heated at reflux (97° C.) for 1.5 h (a solution was obtained at 90° C.). The hot solution was cooled to 20° C. to give a suspension. The suspension was diluted with EtOAc (1.0 L) and suction filtered. The filter cake was washed with EtOAc (400 mL) and air dried. The crude product (42.4 g of yellow solid) was triturated in acetone (3.0 L) at room temperature for 20 h. The suspension was suction filtered; the filter cake was washed with acetone (50 mL) and dried to constant weight in vacuo at 35° C. to give 25.4 g (57%) as a light yellow solid; mp 141–143° C. (dec) (uncorrected). The proton NMR spectrum was consistent with the proposed structure.

| Elemental analysis: | C | H | N | S | Br |
|---|---|---|---|---|---|
| Calc. | 49.28 | 5.58 | 5.75 | 6.58 | 16.39 |
| Obs. | 49.21 | 5.53 | 5.79 | 6.50 | 16.32 |

EXAMPLE 8

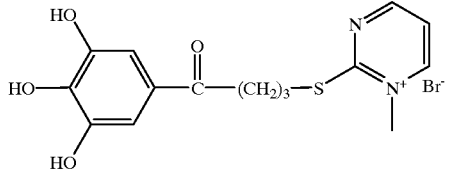

Pyrimidinium,1-methyl-2-[[3-[(3,4,5-trihydroxybenzoyl)-oxy]propyl]thio]-,bromide 3-Bromopropyl gallate A suspension of gallic acid (40.0 g, 0.235 mol), 3-bromo-1-propanol (100 g, 0.719 mol), and conc. sulfuric acid (3.0 mL) was stirred and heated at 115–120° C. until a solution was obtained (10–20 min), then cooled to 100° C. and stirred at 100° C. for 3 h. Cooled to room temperature, diluted with EtOAc (500 mL), and washed with H$_2$O (250 mL), 20% NaHCO$_3$ (2×250 mL), and brine (250 mL). The organic layer was dried (MgSO$_4$), filtered, and concentrated to give the crude product (137 g). The crude material was purified by column chromatography (2.2 kg silica gel eluted with EtOAc:hexanes (1:1)) to give 65.1 g (95%)as a cream-colored pasty solid.

2(1H)-Pyrimidinethione, 1-methyl-

To a stirred mixture of 1-methyl-2-thiourea (573.8 g, 6.365 mol) and malonaldehyde bis(dimethylacetal) (949.6 g, 5.783 mol) in EtOH (11.3 L) was added 10 M HCl (575 mL, 5.75 mol) in one portion. The resulting mixture was stirred at 25° C. for 18 h then concentrated in vacuo. The residue was dissolved in H$_2$O (11.1 L) and the solution was made alkaline by portionwise addition of K$_2$CO$_3$ (448 g). The alkaline solution was extracted with CH$_2$Cl$_2$ (3×7.2 L) and the combined extracts were dried (MgSO$_4$), filtered, and concentrated to give the crude product. The crude product was dissolved in refluxing EtOH (4.0 L) and stored at 3° C. for 18 h. The resulting precipitate was collected by suction filtration and dried to constant weight in vacuo at 40° C. to give 94.1 g (12.9%) as a yellow solid.

Pyrimidinium, 1-methyl-2-[[3-[(3,4,5-trihydroxybenzoyl)-oxy]propyl]thio]-, bromide To a solution of 3-bromopropyl gallate (54.9 g, 0.19 mol) in 1-propanol (350 mL) was added the preceding intermediate (23.8 g, 0.19 mol), and the resulting suspension was heated at reflux (97° C.) for 0.5 h (a solution was obtained at 90° C., then after a few minutes at reflux a precipitate began to fall out of solution). The hot suspension was suction filtered, and the filter cake was washed with 1-propanol (4×75 mL) and dried to constant weight in vacuo at 35° C. to give 33.5 g (42%) as a light yellow solid; mp 223–225° C. (dec) (uncorrected). The proton NMR spectrum was consistent with the proposed structure.

| Elemental analysis: | C | H | N | S | Br |
|---|---|---|---|---|---|
| Calc. | 43.18 | 4.11 | 6.71 | 7.68 | 19.15 |
| Obs. | 42.91 | 4.14 | 6.68 | 7.63 | 19.15 |

EXAMPLE 9

Pyridinium, 1-methyl-2-[(hexadecyl)thio]-, bromide

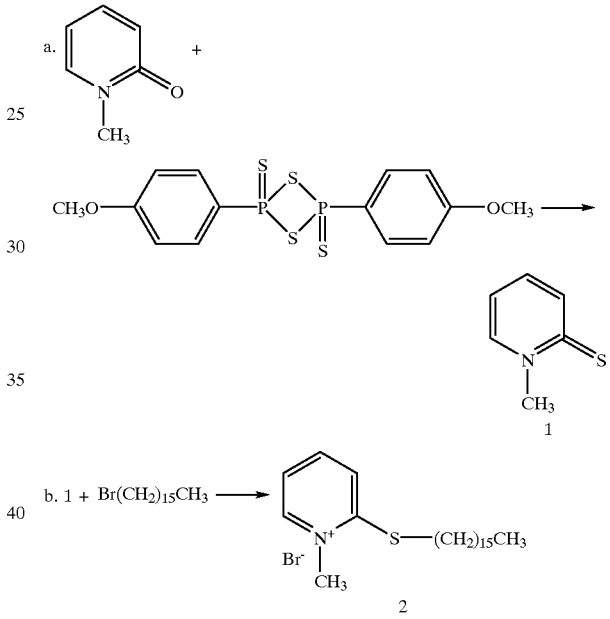

Methyl-2-thiopyridone (1)

A stirred mixture of 1-methyl-2-pyridone (20.0 g, 183 mmol) and Lawesson's Reagent (37.0 g, 91.5 mmol) in dry toluene (100 mL) was heated at reflux for 15 min. then the toluene was removed by evaporation in vacuo at 60° C. The residue was distilled in vacuo to give crude product; bp, 175–177° C. (13 torr). This yellow liquid was dissolved in MeOH (15 mL), and the solution was cooled to 0° C. with stirring. The precipitated solid was collected by filtration, rinsed with hexanes (2×40 mL) and dried to constant weight in vacuo to give 14.0 g (61%) of material is suitable for further transformation. One additional reaction was performed to furnish another 27.7 g lot of similarly pure intermediate.

Pyridinium, 1-methyl-2-[(hexadecyl)thio]-, bromide (2)

A stirred mixture of the preceding intermediate (11.1 g, 88.7 mmol) and 1-bromohexadecane (27.1 g, 88.8 mmol) in 1-PrOH (100 mL) was heated at reflux for 3.5 h then clarified by filtration and stored at 3° C. for 18 h. The resulting crystalline precipitate was collected by filtration, rinsed with EtOH (3×15 mL) followed by Et$_2$O (2×50 mL), then dried to constant weight in vacuo at 60° C. to give 31.1 g (81%) of purified product. One additional reaction was performed to give another 66.7 g lot of purified material. The two lots were thoroughly blended to give a total of 97.8 g of product as a white solid; mp(uncorrected) 111–114 degrees C. Proton NMR and IR spectra were consistent with the proposed structure.

| Elemental analysis: | C | H | N | S | Br |
|---|---|---|---|---|---|
| Calc. | 61.37 | 9.37 | 3.25 | 7.45 | 18.56 |
| Obs. | 61.46 | 9.32 | 3.23 | 7.40 | 18.65 |

EXAMPLE 10

1H-Imidazolium, 1,3-dimethyl-2-(hexadecylthio)-, iodide
Reaction sequence:

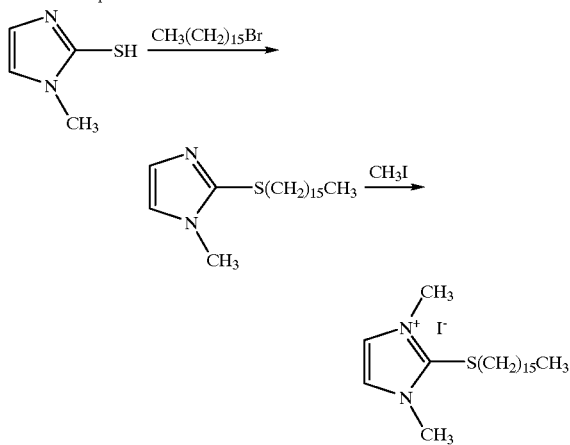

To a stirred solution of 2-mercapto-1-methylimidazole (36.3 g, 318 mmol) in dry DMF (250 ml) was added NaH (12.7 g, 60% in mineral oil, 318 mmol) in portions over 0.5 h. The resulting solution was stirred for an additional 1 h, then hexadecyl bromide (10 g, 97%, 318 mmol) was added in one portion. The reaction mixture was heated for 1 h with stirring at 50° C., then cooled and added to stirred ice-$H_2O$ (1.5 L). The resulting biphasic mixture was extracted with hexanes (2×500 mL). The combined hexane extracts were dried over $Na_2SO_4$ (25 g), then clarified and treated, in one portion, with MeI (100 g, 705 mmol). The stirred mixture was heated at reflux for 1.0 h then cooled to room temperature. The precipitated solid was collected by filtration and dissolved in $CHCl_3$ (1.0 L). The resulting solution was clarified, diluted with hexanes (1.0 L) then concentrated in vacuo at 40° C. to a volume of approximately 1.0 L. The resulting precipitate was collected by filtration and dried to constant weight in vacuo at 40° C. to give 80.9 g (53%) of purified product; mp, 124–126° C. (corrected).

| Elemental analysis: | C | H | N | S | I |
|---|---|---|---|---|---|
| Calc. | 52.49 | 8.60 | 5.83 | 6.67 | 26.41 |
| Obs. | 52.63 | 8.60 | 5.75 | 6.59 | 26.28 |

$sp^2$ Carbon Protecting Groups

The $sp^2$ protected thiol compounds of the present invention can be prepared by any of a number of procedures known to those skilled in the art.

For example, the thiocarboxylic acid derivatives can be prepared by reacting acyl chlorides with $H_2S$ or alkylthiols. The carbamothioic acid derivatives can be prepared via hydrolysis of thiocyanates. The dithiocarboxylic acid derivatives can be prepared by treating carboxylic acids with $P_4S_{10}$ and a primary alcohol. The carbonodithioic acid derivatives can be prepared by the addition of alcohols to carbon disulfide in the presence of base to form a salt of the acid and by imparting an alkyl halide to the reaction mixture to form the ester. The carbamodithioic acid derivatives can be prepared by the addition of primary or secondary amines to carbon disulfide.

The following non-limiting examples illustrate exemplary methods of preparing a few compounds of the invention.

EXAMPLE 11

1-Naphthalenesulfonamide, 5-(dimethylamino)-N-[2-[[(2-(ethoxy)thioxomethyl]thio] ethyl]

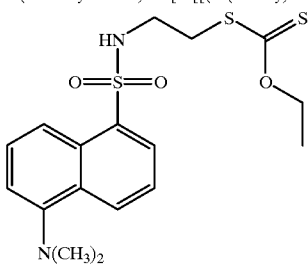

Naphthalenesulfonamide, 5-(dimethylamino)-N-(2-bromoethyl)

A suspension of 5-dimethylaminonaphthalene-1-sulfonyl chloride (50.0 g, 0.185 mol) and 2-bromoethylamine hydrobromide (40.4 g, 0.197 mol) in THF (500 mL) was cooled to 2° C. A solution of triethylamine (38.5 g, 0.380 mol) in THF (250 mL) was added dropwise over a 2 h period while maintaining the internal temperature below 6° C. After complete addition the mixture was stirred at ambient temperature for 17 h. The mixture was clarified then concentrated to an orange oil which was chromatographed over silica (2.2 kg) packed and eluted with hexanes-EtOAc (3:1). Fractions (500 mL) containing the purified product were combined, clarified, then concentrated to a damp solid. This material was triturated in hexanes (250 mL), collected on a filter, washed with hexanes (50 mL) then dried to constant weight in vacuo at 40° C. to give 56.9 g (86.1% yield) of product as a off-white crystalline solid.

1-Naphthalenesulfonamide, 5-(dimethylamino)-N-[2-[[(ethoxy)-thioxomethyl]thio]ethyl]-

A mixture of the preceding intermediate (43.3 g, 121 mmol) and O-ethylxanthic acid, potassium salt (19.7 g, 123 mmol) in anhydrous acetone (430 mL) was heated at reflux for 18 h. The mixture was cooled to ambient temperature, clarified, and the filtrate was concentrated in vacuo to an oil. This material was chromatographed over silica gel (1 kg) packed and eluted with hexanes-EtOAc (3:1). Fractions containing the purified product were combined, clarified, then concentrated to a thick slurry which was diluted with hexanes (200 mL). The resulting solid was collected on a filter, rinsed with hexanes (2×75 mL), then dried to constant weight in vacuo to give 19.1 g of product. The mixed fractions from this column were combined, concentrated, then rechromatographed over silica gel (2.0 kg) packed and eluted with hexanes-EtOAc (3:1). Fractions containing the purified product were combined, clarified, then concentrated in vacuo to a thick oil. This was dissolved in $CH_2Cl_2$ (50 mL), diluted with hexanes (200 mL), then cold evaporated to a thick slurry. The resulting solid was collected on a filter, washed with hexanes (100 mL), then dried to constant weight in vacuo to give 18.9 g of product. A second crop of material was obtained by cold evaporating the two combined filtrates to give 0.5 g of product (total yield 38.5 g, 82%), mp(uncorrected) 85–86 degrees C. Proton NMR and IR spectra were consistent with the proposed structure.

| Elemental analysis: | C | H | N | S |
|---|---|---|---|---|
| Calc. | 51.23 | 5.56 | 7.03 | 24.13 |
| Obs. | 51.19 | 5.56 | 6.99 | 24.14 |

EXAMPLE 12

S-hexadecyl ethanethioate
Reaction sequence:

$$H_3CCl + HS(CH_2)_{15}CH_3 \longrightarrow CH_3CS(CH_2)_{15}CH_3$$

A mixture of acetyl chloride (1.0 L, 1.1. kg, 14 mol) and 1-hexadecanethiol (95%, 168 g, 0.62 mol) was stirred at reflux for 3 h, then volatile components were removed by evaporation in vacuo (60° C., 5 torr). The residue was recrystallized from warm (35° C.) hexanes (500 mL) by cooling at 4° C. for 18 h. The weight in vacuo to give 174.5 g (94%) of purified product; mp, 29 –31° C. (corrected).

| Elemental analysis: | C | H | S |
|---|---|---|---|
| Calc. | 71.93 | 12.07 | 10.67; |
| Found | 72.17 | 12.12 | 10.84. |

The NMR (500 MHz) and IR agreed with the proposed structure.

EXAMPLE 13

S-(4-Aminobutyl) hexadecanethioate hydrochloride
Reaction sequence:

a. Phthalimide-N(CH₂)₄Br + CH₃CH₂OCS₂⁻K⁺ ⟶

Phthalimide-N(CH₂)₄SCOCH₂CH₃
1 b. 1 $\xrightarrow{H_2NNH_2 * H_2O}$ $\xrightarrow{HCl}$ HCl * H₂N(CH₂)₄SH
2 c. 2 + CH₃(CH₂)₁₄CCl ⟶ CH₃(CH₂)₁₄CS(CH₂)₄NH₂ * HCl
3 a. (4-Phthalimidobutyl)xanthic acid, O-ethyl ester (1)

A mixture of N-(4-bromobutyl)phthalimide (138 g, 489 mmol) and O-ethylxanthic acid, potassium salt (97.7 g, 609 mmol) in DMF (400 mL) was stirred for 1 h then blended into stirred ice-H₂O (2 kg). The precipitated solid was collected by filtration, air-dried and doubly recrystallized from boiling EtOH (2×700 mL). The recovered solid was dried to constant weight in vacuo at 50° C. to give 114.8 g (73%) of material suitable for further transformation.

b. 4-Amino-1-butanethiol hydrochloride (2)

To a solution of (1) (105.8 g, 327.4 mmol) in CH₃CN (400 mL) was added H₂NNH₂ * H₂O (47.6 mL, 49.2 g, 980 mmol). The mixture was stirred for 0.5 h at 60° C. then evaporated in vacuo at 40° C. to a solid residue. This material was dissolved in H₂O (450 mL) and the pH of the solution was adjusted to 2–3 with concentrated HCl. The resulting suspension was stored for 1.0 h at 0° C., then the precipitate was removed by filtration. Additional concentrated HCl (200 mL) was added to the filtrate and the yellow solution was heated at reflux for 6.0 h, during which time the evolution of COS gradually slowed to a stop. The resulting solution was evaporated in vacuo at 60° C. to a semi-solid residue. This residue was dried by azeotropic distillation with toluene (3×100 mL) and then extracted into CH₂Cl₂ (900 mL). Evaporation of the clarified CH₂Cl₂ extract yielded 31.4 g (68%) of the hydrochloride salt as a very pale yellow semi-solid suitable for further transformation.

c. S-(4-Aminobutyl) hexadecanethioate hydrochloride (3)

A solution of (II) (31.4 g, 222 mmol) and palmitoyl chloride (60.9 g, 222 mmol) in dry CH₃CN (400 mL) was stirred at 70° C. for 2.0 h and then at 10° C. for 1.0 h. The precipitated solid was collected by filtration and air-dried. This material was recrystallized from boiling EtOH (400 mL) to give a white crystalline solid which was collected by filtration, washed with Et₂O (3×100 mL) and dried to constant weight in vacuo at 60° C. to give 52.0 g (62%) of purified product; mp, 138–141° C. (corrected).

| Elemental analysis: | C | H | Cl | N | S |
|---|---|---|---|---|---|
| Calc. | 63.20 | 11.14, | 9.33 | 3.69 | 8.44; |
| Found | 63.32 | 11.16 | 9.22 | 3.71 | 8.37. |

The NMR (500 MHz) and IR agreed with the proposed structure.

EXAMPLE 14

Methanaminium, N-methyl-N-[1-(hexadecylthio)ethylidene]-, bromide $$H_3CN(CH_3)_2 \overset{S}{\parallel} + CH_3(CH_2)_{15}Br \longrightarrow$$

$$CH_3(CH_2)_{15}S-\overset{N(CH_3)_2^+}{\underset{}{C}}-CH_3 \quad Br^-$$
1

To a stirring solution of N,N-dimethylthioacetamide (33.8 g, 0.33 mol) in acetonitrile (300 mL) was added 97%

1-bromohexadecane (103.1 g, 0.33 mol) and tetrahydrofuran (200 mL), to give a complete solution. The mixture was heated at reflux for 72 h. After cooling to 10° C., the suspension was suction filtered, and the filter cake was washed with Et$_2$O (500 mL). The white solid was dried in vacuo at room temperature for 6 h to give 68.2 g (51%) of target compound as a white solid; mp 80–92° C. (uncorrected). Proton NMR and IR spectra were consistent with the proposed structure.

| Elemental analysis: | C | H | N | S | Br |
|---|---|---|---|---|---|
| Calc. | 58.80 | 10.36 | 3.43 | 7.85 | 19.56 |
| Obs. | 58.56 | 10.43 | 3.41 | 7.76 | 19.60 | sp$^3$ Carbon Protecting Groups

The compounds of the invention can be prepared by any of a number of procedures known to those skilled in the art.

For example, the thioether compounds can be prepared by the treatment of a suitable alkyl halide with a thiol. The thioacetal and dithioacetal compounds can be prepared by the treatment of suitable aldehydes and ketones with a thiol. The compounds capable of undergoing heterolytic β-elimination can be prepared via nucleophilic addition of a thiol onto a suitable activated olefin in a Michael-type addition reaction.

The following non-limiting examples illustrate exemplary methods of preparing a few compounds of the invention.

EXAMPLE 15

1-Naphthalenesulfonamide,
5-(dimethylamino)-N-[2-[[(2-(methyl-sulfonyl)ethyl]thio]ethyl]

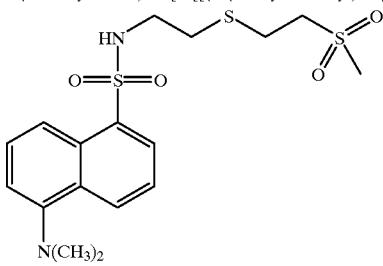

To a stirred suspension of 2-(methylsulfonyl)ethanethiol (17.5 g, 0.12 mol) and 5-(dimethylamino)-N-(2-bromoethyl)-1-naphthalenesulfonamide (43.8 g, 0.12 mol) in acetone (1.8 L) was added anhydrous potassium carbonate (19.6 g, 0.142 mol) at room temperature under argon. The reaction mixture was refluxed for 1 h, then additional potassium carbonate (58.5 g, 0.42 mol) and acetone (50 mL) were added followed by continued reflux for 1.5 h. The reaction mixture was cooled to room temperature, then poured into stirred water (8 L) and extracted with EtOAc (2×4 L). The combined EtOAc extracts were washed with water (1×4 L) then washed with brine (1×4 L) and dried over magnesium sulfate. The clear EtOAc extract was concentrated to give crude product. The crude product was chromatographed on silica gel (2.2 kg) with EtOAc:hexanes 1:1 (12 L) and 4:1 (8 L). Appropriate fractions were combined, filtered and concentrated to give 47.6 g (93.7% yield) of product as a viscous oil. Proton NMR and IR spectra were consistent with the proposed structure.

| Elemental analysis: | C | H | N | S |
|---|---|---|---|---|
| Calc. | 49.01 | 5.81 | 6.72 | 23.09 |
| Calc.* | 49.34 | 6.01 | 6.32 | 21.71 |
| Obs. | 49.52 | 5.98 | 6.41 | 21.96 |

*Calc. for C$_{17}$H$_{24}$N$_2$O$_4$S$_3$·0.3 EtOAc

EXAMPLE 16

Methyl 3-(Hexadecylthio)propanoate
Reaction Sequence:

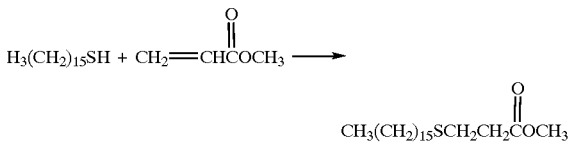

Hexadecyl mercaptan (95%, 180 g, 661 mmol) was added, dropwise over 0.5 h, to a stirred mixture of methyl acrylate (60.0 g, 697 mmol) and benzyltrimethylammonium hydroxide (40 wt. % in methanol, 400 mg, 1.0 mmol). The resulting warm (~60° C.) solution was stirred for one additional hour then volatiles were removed in vacuo at 90° C. The resulting oil was recrystallized from warm (~40° C.) hexanes (500 ml), cooled to −30° C., collected by filtration and dried to constant weight in vacuo at room temperature to give 222.3 g (98%) of purified product; mp, 38–39° C. (corrected).

| Elemental analysis: | C | H | S |
|---|---|---|---|
| Calc. | 69.71 | 11.70 | 9.30; |
| Found | 69.78 | 11.54 | 9.26. |

The $^1$H NMR and IR agree with the proposed structure.

EXAMPLE 17

4-[(Hexadecylthio)methyl]-N,N-dimethylbenzenamine
Reaction Sequence:

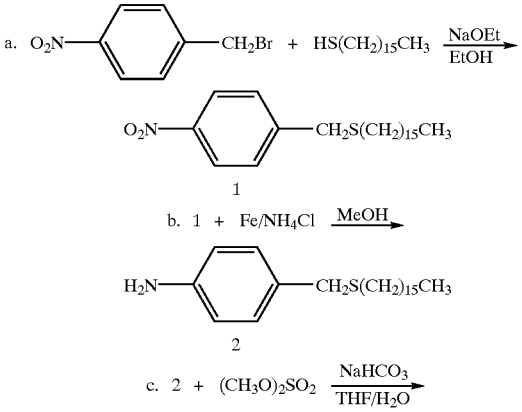

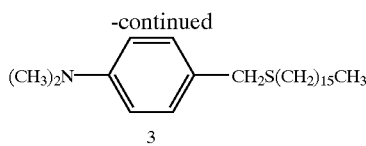

a. 4-[(Hexadecylthio)methyl]-1-nitrobenzene (1):

A solution of 4-nitrobenzyl bromide in ethanol (150.0 g, 0.694 mol in 1.5 L) was brought to reflux. Separately, a solution of 1-hexadecanethiol in ethanol (231 mL, 0.691 mol in 1.5 L) was treated with sodium ethoxide in ethanol (258 mL, 0.691 mol of a 21% solution) over ten minutes, stirred at room temperature for 15 minutes, then warmed to dissolve the precipitate. This was then added to the benzyl bromide solution over twenty minutes, stirred at room temperature for two hours, then allowed to sit undisturbed overnight. The crystallized thioether was collected and combined with the product from a 230 mmol run. This light yellow solid was dissolved in $CH_2Cl_2$ (3 L), washed with water (1 L), then dried ($Na_2SO_4$), filtered, and spin-evaporated to give 324.5 g of 1 (89.5% yield). The material was a single spot by TLC (19:1 hexanes/EtOAc), and was suitable for further transformation.

b. 4-[(Hexadecylthio)methyl]benzeneamine (2):

Ammonium chloride (152.9 g, 2.858 mol), 1 (225.0 g, 0.572 mol), water (2.8 L), methanol (3.8 L) were combined and mechanically stirred at 50° C., then powdered iron (95.9 g, 1.715 mol) was added portionwise over ten minutes. The suspension was vigorously stirred at reflux for 2.5 hours, then hot filtered through a celite pad. The pad was rinsed with water (3×700 mL) and $CH_2Cl_2$ (5×700 mL). The aqueous layer was extracted with $CH_2Cl_2$ (3×1 L), then concentrated to remove methanol and again extracted with $CH_2Cl_2$ (3×500 ml). The combined organics were washed with water (2×3 L), dried ($Na_2SO_4$), filtered, and spin-evaporated to give 198.1 g (95.3% yield) of 2 as a pale yellow solid. TLC (7:1 hexanes/EtOAc) indicated a single spot. This lot was combined with that of a 100 mmol run to give a total of 231 g of 2 (94.3% yield) which was suitable for further transformation.

c. 4-[(Hexadecylthio)methyl]-N,N-dimethylbenzeneamine (3):

A solution of sodium bicarbonate in water (168 g, 2.0 mol in 1.3 L) was added to a vigorously stirred solution of 2 in THF (181 g, 0.5 mol in 1.5 L), under argon, at 0° C. Dimethyl sulfate (165 mL, 1.75 mol) was added dropwise over 30 minutes, and stirring was continued for a total of 20 h. The ice bath was removed after the first hour. The reaction was followed by TLC (9:1 hexanes/EtOAc), and initially showed mono-methylated material at Rf=0.56. After 20 h, concentrated $NH_4OH$ (300 mL) was added and stirred for 15 minutes, then EtOAc and brine (1 L each) were added and the layers were separated. The aqueous portion was saturated with solid NaCl, extracted with EtOAc (5×500 mL), and discarded. The combined organics were washed with brine (500 mL), dried ($Na_2SO_4$), and spin-evaporated to a yellow oil. A similar reaction was done previously on 137.7 mmol of 2. The combined lots were dissolved in $CH_2Cl_2$, then eluted from a silica gel pad with $CH_2Cl_2$. The eluent was spin-evaporated to give 160.1 g of 3 as an oil, which was purified by chromatography (1.8 kg $SiO_2$ eluted with 39:1 hexanes/EtOAc) to give 91.1 g of 3. This material was recrystallized from ethanol containing 1% water, then dried in vacuo at room temperature to give 57.9 g (23.3% yield) of pure 3; m.p. 41–43° C.

| Elemental analysis: | C | H | N | S |
|---|---|---|---|---|
| Calc. | 76.66 | 11.58 | 3.57, | 8.19; |
| Found | 76.37 | 11.63 | 3.61 | 8.43. |

The $^1H$ NMR, $^{13}C$ NMR, and IR agree with the proposed structure.

EXAMPLE 18

1,3,5-Cycloheptatriene, 7-(hexadecylthio)-

Tropylium tetrafluoroborate (10.0 g, 0.056 mol) was ground and placed in a reaction flask with MeOH (100.0 mL). This suspension was stirred under argon for 10 min at room temperature, and then n-hexadecanethiol, (90%) (15.0 g, 0.052 mol) was added over 5 min. The reaction mixture (suspension) was stirred for 2 h. At this point, TLC showed only a small amount of unreacted thiol. To the reaction mixture was added $NaHCO_3$ (8 g, 0.095 mol) followed by stirring for 15 min. and filtration through a small pad of silica gel (~20 g) with elution by hexanes (200 mL). The solution was evaporated (bath temp ~30° C.) to give an oil which was purified by column chromatography with silica gel (100 g) eluting with hexanes to give 17.2 g (95%) as a colorless oil. Additional reactions were performed to give a total of 58.1 g of target compound. Proton NMR and IR spectra were consistent with the proposed structure.

| Elemental analysis: | C | H | S |
|---|---|---|---|
| Calc. | 79.24 | 11.56 | 9.20 |
| Obs. | 78.63 | 11.85 | 9.43 |

Metal Based Protecting Groups

The metal mercaptides of the present invention can be prepared by a number of methods known to those who are skilled in the art.

R—S—Met—$X_n$ can be made by reactions of the type:

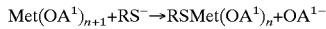

Met(OA$^1$)$_{n+1}$+RS$^-$→RSMet(OA$^1$)$_n$+OA$^{1-}$ e.g., for Ti and Zr.

R—S—Met(M)$_m$X$_n$ can be made by reactions of the type:

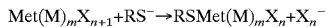

Met(M)$_m$X$_{n+1}$+RS$^-$→RSMet(M)$_m$X$_n$+X$_n^-$ e.g., for V and Bi.

Furthermore, metal mercaptides of the present invention can be made via the addition of the cosmetic thiol to a solution of salts of heavy metals. This can be accomplished by adding the thiol to an aqueous, hydroalcoholic or alcoholic solution of a salt of the metal. The formed mercaptides of the heavy metals may then precipitate. The precipitated mercaptide can then be filtered and washed with an aqueous, hydro-alcoholic or alcoholic solution containing some of the thiol to prevent hydrolysis [E. Reid, *Organic Chemistry of Bivalent Sulfur, Volume I*, 1958].

Non-metal and Metalloid Based Protecting Groups

Thiol derivatives of non-metals and metalloids can be prepared from their halides in the presence of a hydrogen halide acceptor hydrogen halide acceptor or by using a metal thiolate, such as lead, where Et represents an ethyl group, Pb is lead, and the other symbols are as defined above [M. E. Peach, "Thiols as Nucleophiles", in *The Chemistry of the Thiol Group*, 1974, John Wiley and Sons, pp. 747.]:

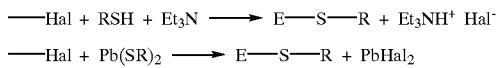

Energy Sensitive Protecting Groups

I. 2-Nitrobenzyl derivatives

The 2-nitrobenzyl derivatives can be prepared by reaction of the corresponding 2-nitrobenzyl halide with a thiol in the presence of a base:

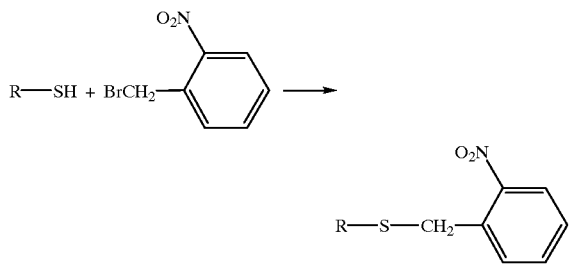

II. 2-Nitrobenzyloxycarbonyl Derivatives

The 2-nitrobenzyloxycarbonyl derivatives can be prepared by the reaction of phosgene with the corresponding alcohol, i.e., 2-nitrobenzyl alcohol, 6-nitroveratryl alcohol, 2-nitrobenzhydrol, and 2,2'-dinitrodiphenylmethanol. The resulting acyl chloride can then be reacted with a thiol to yield the corresponding 2-nitrobenzyloxycarbonyl derivative:

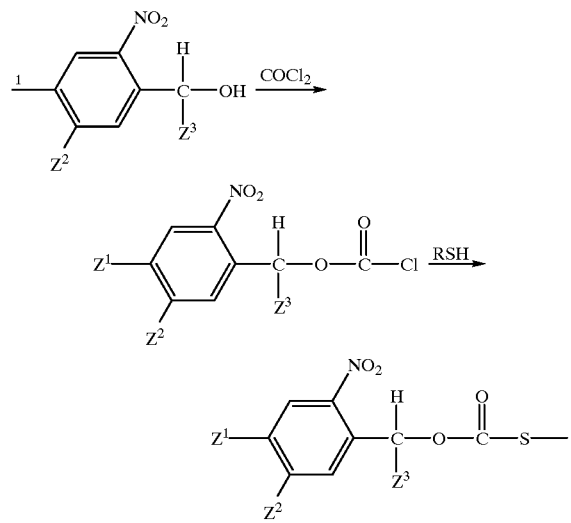

where $Z^1$ and $Z^2$ are H, or $OCH_3$ and $Z^3$ is H, $C_6H_5$ or o-$O_2N$—$C_6H_4$.

III. Benzyloxycarbonyl Derivatives

The 3,5-dimethoxybenzyloxycarbonyl group can be introduced by reacting 3,5-dimethoxybenzyl p-nitrophenyl carbonate with a thiol:

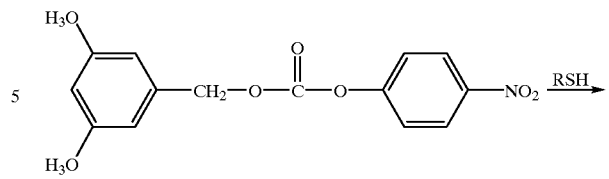

IV. α,α-Dimethylbenzyloxycarbonyl Derivatives

The α,α-dimethyl-3,5-dimethoxybenzyloxycarbonyl compounds can be prepared by the reaction of α,α-dimethyl-3,5-dimethoxybenzyloxycarbonyl azide with a thiol:

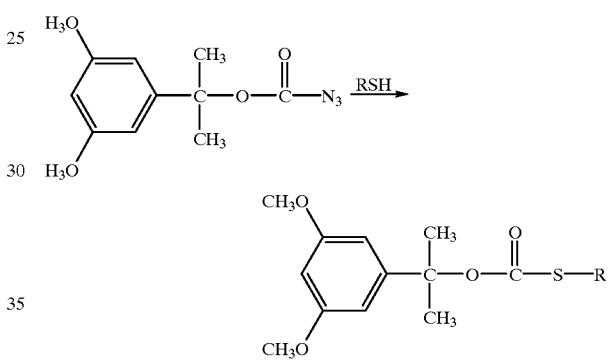

V. 3-Nitrophenyloxycarbonyl Derivatives

The 3-nitrophenyloxycarbonyl compound can be prepared by reaction of 3-nitrophenol with phosgene to yield 3-nitrophenyloxycarbonyl chloride. The latter can then be reacted with a thiol:

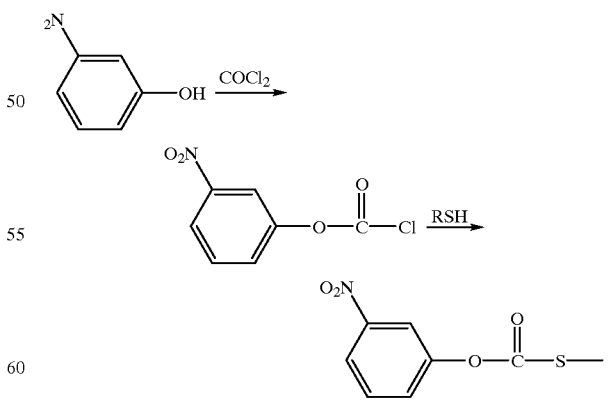

VI. Phenacyl Derivatives

The 4-methoxyphenacyl compound can be prepared by reaction of phenacyl bromide with a thiol:

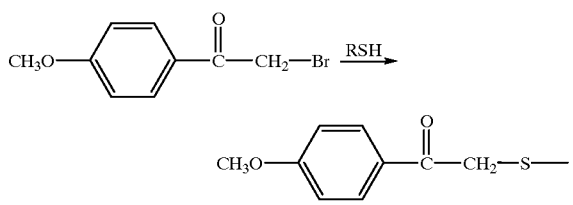

The α,α-methylphenacyl compound can be prepared by reaction of alpha-methylphenacyl bromide with a thiol:

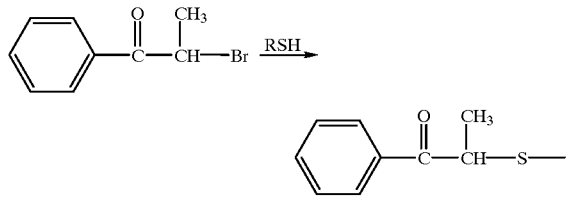

VII. tert-Butyloxycarbonyl Derivatives

The tert-butyloxycarbonyl compound can be prepared by reaction of tert-butyloxycarbonyl chloride with a thiol:

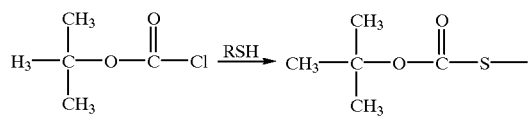

EXAMPLES OF PREFERRED MODIFIED COSMETICALLY ACTIVE AGENTS

In order that those skilled in the art will be better able to practice the invention, the following examples are given by way of illustration and not by way of limitation. The following are non-limiting examples of preferred cosmetically active functional group, R, and "hook" combinations for use in topical formulas:

EXAMPLE 19

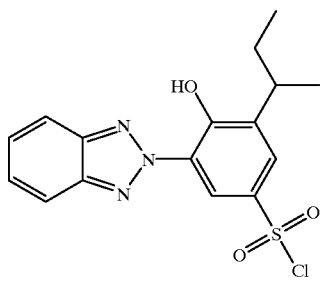

3-Benzotriazol-2-yl-5-sec-butyl-4-hydroxy-benzenesulfonyl chloride

To a stirred suspension of 3-benzotriazol-2-yl-5-sec-butyl-4-hydroxybenzenesulfonyl chloride (14.19 g, 0.0388 mol) and 2-bromoethylamine hydrobromide (8.44 g, 0.0412 mol) in acetonitrile (100 g) at 0–5° C. under nitrogen was added dropwise a solution of triethylamine (8.05 g, 0.0796 mol) in acetonitrile (60 g). When the addition was complete, the reaction mixture was stirred at room temperature for 20 hours. The reaction mixture was suction filtered and the filter cake was washed with acetonitrile (20 g). The filtrate was spin-evaporated and the residue was suspended in water (130 g). The suspension was suction filtered and the filter cake was dried to give 10 g of 3-benzotriazol-2-yl-N-(2-bromoethyl)-5-sec-butyl-4-hydroxy-benzenesulfonamide as a white powder.

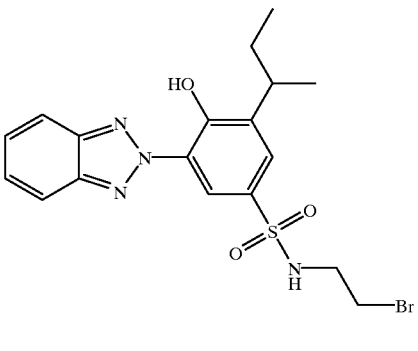

$^{13}$C NMR (90 MHz, [D$_6$]DMSO): δ=12.70 (CH$_3$), 20.74 (CH$_3$), 29.65 (CH$_2$), 32.96 (CH$_2$), 34.56 (CH), 45.27 (CH$_2$), 118.70 (aryl CH), 119.91 (aryl CH), 126.0 (aryl Cq), 126.63 (aryl CH), 129.22 (aryl CH), 132.51 (aryl Cq), 138.83 (aryl Cq), 143.73 (aryl Cq), 151.27 (aryl Cq).

EXAMPLE 20

2-[2-(3-Benzotriazol-2-yl-5-sec-butyl-4-hydroxy-benzenesulfonylamino)-ethylsulfanyl]-1-

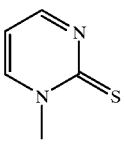

1-Methyl-1H-pyrimidine-2-thione

A stirred mixture of 1-methyl-1H-pyrimidine-2-thione (10.29 g, 0.0816 mol) and 3-benzotriazol-2-yl-N-(2-bromoethyl)-5-sec-butyl-4-hydroxy-benzenesulfonamide (31.29 g, 0.0069 mol) in 1-propanol (80 ml) was heated at reflux for 2 hours. The cooled mixture (0° C.) was filtered and the filtrate was spin-evaporated in vacuo to afford a solid residue (32 g). The residue was suspended in 1-propanol and filtered. The filter cake was dried in vacuo to give 4 g of 2-[2-(3-benzotriazol-2-yl-5-sec-butyl-4-hydroxy-benzenesulfonylamino)-ethylsulfanyl]-1-methyl-pyrimidin-1-ium bromide as a yellowish powder.

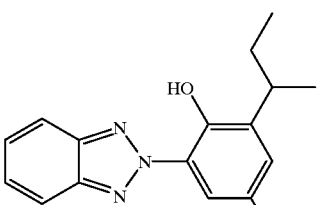
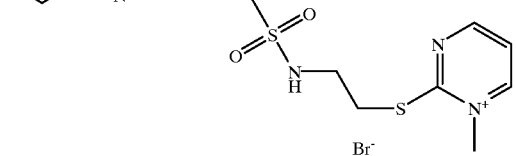

$^{13}$C NMR (90 MHz, [D$_6$]DMSO): δ=10.47 (CH$_3$), 18.49 (CH$_3$), 27.37 (CH$_2$), 30.58 (CH$_2$), 32.22 (CH), 38.36 (CH$_2$), 38.59 (NCH$_3$), 116.52 (aryl CH), 118.0 (aryl CH), 124.0 (aryl Cq), 126.99 (aryl CH), 129.99 (aryl CH), 136.71 (aryl Cq), 141.62 (aryl Cq), 149.18 (aryl Cq), 153.44 (aryl CH), 161.33 (aryl CH), 166.07 (aryl Cq).

EXAMPLE 21

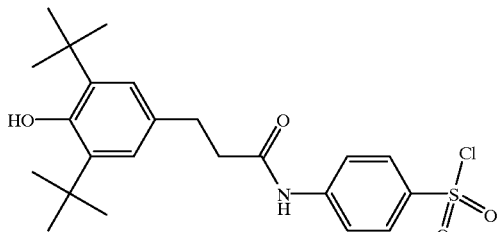

N-[4-(2-Bromoethylsulfamoyl)-phenyl]-3-(3,5-di-tert-butyl-4-hydroxy-phenyl)-propionamide 4-[3-(3,5-Di-tert-butyl-4-hydroxy-phenyl)-propionylamino]-benzenesulfonyl chloride To a stirred suspension of 4-[3-(3,5-di-tert-butyl-4-hydroxy-phenyl)-propionylamino]-benzenesulfonyl chloride (4.38 g, 0.0097 mol) and 2-bromoethylamine hydrobromide (2.11 g, 0.0103 mol) in THF (30 g) at 0–2° C. under nitrogen was added dropwise a solution of triethylamine (2.01 g, 0.0199 mol) in THF (9 g). When addition was complete, the reaction mixture was stirred at room temperature for 20 hours. The reaction mixture was filtered and the filtrate was spin evaporated in vacuo. The residue was chromatographed over silica (toluene/acetone 75:25) to give 2.7 g of N-[4-(2-bromoethylsulfamoyl)-phenyl]-3-(3,5-di-tert-butyl -4-hydroxy-phenyl)-propionamide as a white crystalline solid, mp 153–155° C.

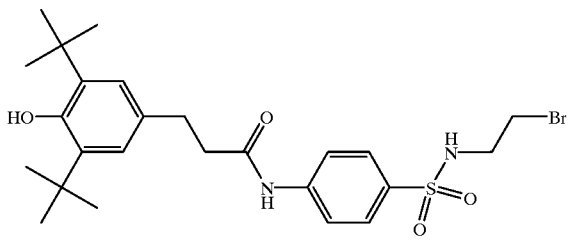

$^{13}$C NMR (90 MHz, [D$_6$]DMSO): δ=31.27 (t-butyl CH$_3$), 32.78 (CH$_2$), 35.3 (t-butyl Cq), 39.50 (CH$_2$), 45.21 (CH2), 119.57 (aryl CH), 125.1 (aryl CH), 128.50 (aryl CH), 129.75 (aryl Cq), 132.65 (aryl Cq), 134.87 (aryl Cq), 140 (aryl Cq), 143.75 (aryl Cq), 152.86 (aryl Cq), 172.40 (C=O).

EXAMPLE 22

2-(2- {4-[3-(3,5-Di-tert-butyl-4-hydroxy-phenyl)-propionylamino]-benzene-sulfonylamino}-ethylsulfanyl)-1-methyl-pyrimidin-1-ium bromide A stirred mixture of 1-methyl-1H-pyrimidine-2-thione (2.76 g, 0.0219 mol) and N-[4-(2-bromo-ethylsulfamoyl)-phenyl]-3-(3,5-di-tert-butyl-4-hydroxy-phenyl)-propionamide (9.98 g, 0.0185 mol) in 1-propanol (25 ml) was heated at reflux for 2.5 hours. The mixture was spin-evaporated in vacuo to give a solid residue. The residue was dissolved in ethyl acetate (200 g) and mixed with tert.-butyl-methyl ether (20 g) to give two liquid phases. The lower phase was concentrated in vacuo to give2-(2-{4-[3-(3,5-Di-tert-butyl-4-hydroxy-phenyl)-propionylamino]-benzenesulfonylamino} -ethylsulfanyl)-1-methyl-pyrimidin-1-ium bromide.

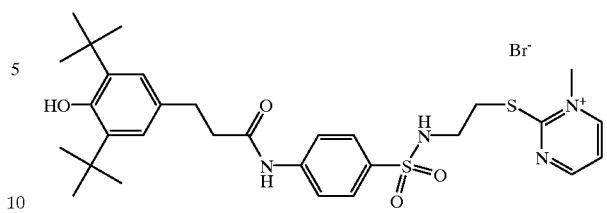

$^1$H NMR (350 MHz, [D$_6$]DMSO): δ=1.38 (s, 18H, t-butyl CH$_3$), 2.64 (m, 2H, CH$_2$), 2.83 (m, 2H, CH$_2$), 3.18 (m, 2H, CH$_2$), 3.50 (m, 2H, CH$_2$), 4.06 (s, 3H, N CH$_3$), 6.98 (s, 2H, aryl H), 7.74 (d, 2H, aryl H), 7.80 (d, 2H, aryl H), 7.91 (m, 1H, pyrimidine H), 9.23 (d, 1H, pyrimidine H), 9.33 (d, 1H, pyrimidine H), 10.43 (s, 1H, OH).

Methods of Using the Protected Thiol Compounds of the Present Invention

The method of use of the various protected thiol compounds is dependent on the product form utilized. The use would be as typically used for the product chosen.

The protected thiol compound of the present invention can be used in a variety of ways in hair care compositions. For example, in the most basic sense the cosmetic actives of the present invention can be applied directly to the hair in an alcohol/solvent/water solution comprising:

| | |
|---|---|
| Protected thiol cosmetic active of Examples 1–22 | 0.5 to 10% |
| Hydroalcoholic solvent | 0 to 95.00% |
| pH modifier, i.e., NaOH or citric acid | pH 3 to 10* |
| Water | Q.S. |

*Note, the pH will vary based on the particular "hook" compound of use and can be adjusted either just prior to treatment with hair or simultaneously with the treatment of hair.

After application, the hair is washed or rinsed to remove excess solvent. The resulting protected thiol cosmetic active will be delivered and bound to the hair permanently, e.g. benefit will last beyond 40 to 80 or more shampoos.

A simple non-limiting treatment composition using a protected thiol compound of the present invention comprises:

| | |
|---|---|
| The Modified UV Absorbers or Antioxidants of Examples 19–22 | 5.00% |
| Methanol | 90.00% |
| NaOH | to pH 8–10 |
| Water | Q.S. |

The preparation of this composition and treatment with hair for proof of performance is described as follows: The modified UV absorber or antioxidant is added to the methanol in a jar and stirred until thoroughly dissolved at 100° F. The water and NaOH is then added with stirring until the solution is thoroughly mixed. With a syringe, one gram of the resulting solution is applied per gram of the hair to be treated. The applied solution is then worked through the hair while wearing rubber gloves. The hair is then covered with plastic wrap and let sit for up to two hours. The hair is then rinsed thoroughly.

The protected thiol compounds can be achieved with any of the protected hooks described herein. Of course, the protected thiol compounds of the present inventions can be applied in differing matrices and formulas as described previously herein.

The protected thiol compounds may also be added to technologies currently well known in the art to treat substrates such as hair, teeth, finger nails, textiles, and animal fur. Nonlimiting examples of such compositions are described in the references below, each of which is incorporated herein by reference in its entirety:

Shampoos-U.S. Pat. No. RE 34,584 (Grote et al.) issued Apr. 12, 1994; U.S. Pat. No. 4,345,080 (Bolich) issued Aug. 17, 1982; U.S. Pat. No. 4,379,753 (Bolich) issued Apr. 12, 1983; and U.S. Pat. No. 4,705,681 (Maes et al.) issued Nov. 10, 1987.

Hair conditioners-U.S. Pat. No. 4,387,090 (Bolich) issued Jun. 7, 1983; U.S. Pat. No. 5,674,478 (Dodd et al.) issued Oct. 7, 1997; and U.S. Pat. No. 5,750,122 (Evans et al.) issued May 12, 1998.

Hair styling compositions-U.S. Pat. No. 5,166,276 (Hayama et al.) issued Nov. 24, 1992; U.S. Pat. No. 5,565,193 (Midha et al.) Oct. 15, 1996; and U.S. Pat. No. 5,658,557 (Bolich et al.) issued Aug. 19, 1997.

Hair coloring compositions-U.S. Pat. No. 4,197,865 (Jacquet et al.) issued Apr. 15, 1980, U.S. Pat. No. 4,125,367 (Bugaut et al.) issued Nov. 14, 1978, U.S. Pat. No. 5,114,429 (Junino et al.) issued May 19, 1992, and U.S. Pat. No. 5,279,620 (Junino et al.) issued Jan. 18, 1994.

Mascara compositions-Commonly assigned U.S. patent application Ser. Nos. 08/951,285 (Alwatarri et al.), filed Oct. 16, 1997, (Attorney's Docket 6345C); 08/757,538 (Bartholomey et al.), filed Nov. 27, 1996 (Attorney's Docket 6397); and 09/121,138 (Alwatarri et al.), filed Jul. 23, 1998 (Attorney's Docket 5654C2); and in PCT Application Nos. US96/04154, published Oct. 31, 1996; US97/19786, published May 7, 1998; and US97/21890, published Jun. 4, 1998.

Nail polish and nail polish subcoat compositions-U.S. Pat. No. 4,179,304 (Rossomando) issued Dec. 18, 1979, U.S. Pat. No. 5,538,717 (LaPoterie) issued Jul. 23, 1996, and U.S. Pat. No. 5,639,447 (Patel) issued Jun. 17, 1997, U.S. Pat. No. 5,567,428 (Hughes) issued Oct. 22, 1996.

Toothpaste compositions-U.S. Pat. No. 4,254,101(Denny) issued Mar. 3, 1981, and U.S. Pat. No. 4,314,990 (Denny et al.) issued Feb. 9, 1982, and PCT Application No. WO 96/15767 (Unilever PLC) published May 30, 1996.

Textile dye and treatment compositions

Other typical compositions are found in *Cosmetic and Toiletry Formulations,* 2nd Ed, Flick, E. W., Noyes Publications (N.J.), *Harry's Cosmeticology,* 7th Ed., Harry, R. G ., Wilkinson, J. B., and Moore R. J., Chemical Pub. Co. (NY) (1982); and *Cosmetics, Science and Technology,* 2nd Ed., Balsam, M. S. and Sagarin, E. S., Wiley-Interscience (NY) (1972) (3 volumes).

Other embodiments of the present invention comprise a system comprising a topical composition containing the protected thiol compound and an activating mechanism. For example the UV absorber composition:

EXAMPLE 23

EXAMPLE 23

| | |
|---|---|
| Modified UV absorber of Example 19 | 3.00% |
| Urea | 10.00% |
| Cocoamidopropyl Betaine | 0.80% |
| Isopropanol | 50.00% |
| Water | Q.S. | can be applied simultaneously with a 5% solution of thioglycolic acid. A preferred embodiment is a kit wherein the treatment solution and the thioglycolic acid are packaged in separate chambers of a dual chamber package and delivered simultaneously from the package.

What is claimed is:

1. A modified UV absorber of the formula (XVI)

wherein $R_1$ is $C_1$–$C_{12}$alkyl, $C_5$–$C_7$cycloalkyl or phenyl-$C_1$–$C_3$alkyl, $R_2$ is hydrogen or halogen, n is 0, 1 or 2 and $Q^-$ is a counterion.

2. A compound of the formula (XVI) according to claim 1, wherein $R_1$ is a $C_1$–$C_6$alkyl group; $R_2$ is hydrogen or chlorine, n is 1 or 2 and $Q^-$ is a halide.

3. A compound of the formula (XVI) according to claim 1, wherein $R_1$ is a $C_3$–$C_5$alkyl group; $R_2$ is hydrogen or chlorine, n is 1 and $Q^-$ is a halide.

4. The compound of the formula according to claim 1.

5. A composition for human and animal hair, which comprises a modified UV absorber of the formula (XVI) according to claim 1.

6. A method of stabilizing the hair of humans and animals against degradation, which comprises contacting said hair with a composition according to claim 5.

7. A method according to claim 6, whereby the color fastness of the hair is improved.

* * * * *

UNITED STATES PATENT AND TRADEMARK OFFICE
CERTIFICATE OF CORRECTION

PATENT NO.    : 6,495,125 B2
DATED         : December 17, 2002
INVENTOR(S)   : Robert Wayne Glenn, Jr. et al.

Page 1 of 2

It is certified that error appears in the above-identified patent and that said Letters Patent is hereby corrected as shown below:

Title page,
Item [75], Inventors, delete "Eric Block, Nishayuna, NY (US); Matthew David Shair, Boston, MA (US);".

Column 2,
Line 43, "pre-to reduction" should read -- pre-reduction --.

Column 4,
Line 22, "→ Ker" should read -- → 2 Ker --.

Column 9,
Line 45, " 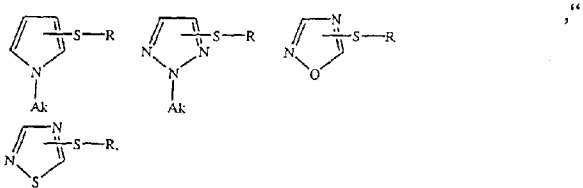 ,"

should read -- 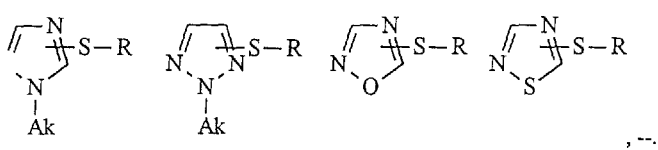 , --.

Column 36,
Line 32, "(iX)" should read -- (ix) --.

Column 38,
Line 19, "orphenyl" should read -- or phenyl --.
Line 66, "anti oxidants" should read -- antioxidants --.

Column 42,
Line 61, "Cymennan-" should read -- Cymerman- --.

Column 44,
Line 25, "HCI" should read -- HCl --.

Column 47,
Line 33, "HCI" should read -- HCl --.

UNITED STATES PATENT AND TRADEMARK OFFICE
CERTIFICATE OF CORRECTION

PATENT NO.   : 6,495,125 B2
DATED        : December 17, 2002
INVENTOR(S)  : Robert Wayne Glenn, Jr. et al.

It is certified that error appears in the above-identified patent and that said Letters Patent is hereby corrected as shown below:

Column 52,
Line 21,

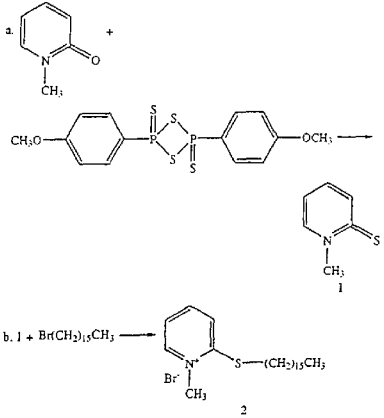

should read --

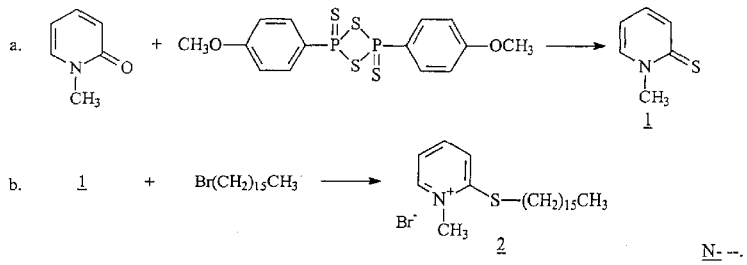

N- --.

Column 67,
Line 56, delete 1st occurrence of "EXAMPLE 23"

Signed and Sealed this

Eighteenth Day of November, 2003

JAMES E. ROGAN
*Director of the United States Patent and Trademark Office*